United States Patent
Ebetino et al.

(10) Patent No.: US 7,026,335 B2
(45) Date of Patent: Apr. 11, 2006

(54) MELANOCORTIN RECEPTOR LIGANDS

(75) Inventors: Frank Hallock Ebetino, Cincinnati, OH (US); Xuewei Liu, San Diego, CA (US); Mark Gregory Solinsky, Cincinnati, OH (US); John August Wos, Maineville, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 82 days.

(21) Appl. No.: 10/410,775

(22) Filed: Apr. 9, 2003

(65) Prior Publication Data

US 2003/0236230 A1 Dec. 25, 2003

Related U.S. Application Data

(60) Provisional application No. 60/376,585, filed on Apr. 30, 2002.

(51) Int. Cl.
*A61K 31/445* (2006.01)
*C07D 401/04* (2006.01)

(52) U.S. Cl. .................. 514/326; 546/208; 546/210

(58) Field of Classification Search ............... 514/326; 546/208, 210
See application file for complete search history.

(56) References Cited

U.S. PATENT DOCUMENTS

| | | | |
|---|---|---|---|
| 5,071,859 A * | 12/1991 | Knudsen et al. ............ 514/326 |
| 5,492,916 A | 2/1996 | Morriello et al. |
| 5,494,919 A | 2/1996 | Morriello et al. |
| 5,536,716 A | 7/1996 | Chen et al. |
| 5,721,250 A | 2/1998 | Morriello et al. |
| 5,721,251 A | 2/1998 | Chen et al. |
| 5,783,582 A | 7/1998 | Guo et al. |
| 5,804,578 A | 9/1998 | Chakravarty et al. |
| 5,877,182 A | 3/1999 | Nargund et al. |
| 5,880,125 A | 3/1999 | Nargund |
| 5,936,089 A | 8/1999 | Carpino et al. |
| 5,965,565 A | 10/1999 | Chen et al. |
| 6,294,534 B1 | 9/2001 | Nargund et al. |
| 6,350,760 B1 | 2/2002 | Bakshi et al. |
| 6,767,915 B1 | 7/2004 | Bakshi et al. |
| 2003/0092732 A1* | 5/2003 | Yu et al. .................... 514/326 |

FOREIGN PATENT DOCUMENTS

| WO | WO 94/13696 A1 | 6/1994 |
|---|---|---|
| WO | WO 94/19367 A1 | 9/1994 |
| WO | WO 96/02530 A1 | 2/1996 |
| WO | WO 96/13265 A1 | 5/1996 |
| WO | WO 96/38471 A1 | 12/1996 |
| WO | WO 98/10653 A1 | 3/1998 |
| WO | WO 99/55679 A1 | 11/1999 |
| WO | WO 99/58501 A1 | 11/1999 |
| WO | WO 99/64002 A1 | 12/1999 |
| WO | WO 00/74679 A1 | 12/2000 |
| WO | WO 01/70337 A1 | 9/2001 |
| WO | WO 01/70708 A1 | 9/2001 |
| WO | WO 01/91752 A1 | 12/2001 |
| WO | WO 02/00654 A1 | 1/2002 |
| WO | WO 02/15909 A1 | 2/2002 |
| WO | WO 02/059107 A1 | 8/2002 |
| WO | WO 02/059117 A1 | 8/2002 |
| WO | WO 02/068387 A2 | 9/2002 |
| WO | WO 02/068388 A2 | 9/2002 |
| WO | WO 02/070511 A1 | 9/2002 |
| WO | WO 03/013571 A1 | 2/2003 |
| WO | WO 03/031410 A1 | 4/2003 |

OTHER PUBLICATIONS

Heckel et al. "Preparation of benzimidazolyalaniamide . . ." CA 120:107744 (1994).*
Chen et al. "Preparation of a combinatorial library . . ." CA 134:295742 (2001).*
Yu et al. "Preparation of peptides . . . " CA 137:295252 (2002).*
Silverman "The organic chemistry of drug design and drug action" Academic Press, (1993) p. 357-358.*
Bundgaard "Design of prodrugs" Elsevier, p. 27, 31, 32 (1986).*
Lendaris et al. "reach through claims . . ." Intellectual property update, v.4, No. 5, (2004).*
Drustrup et al. "Prodrug forms for the sulfonamide groups." Int. J. Pharm. 37, 87-95 (1987).*

* cited by examiner

Primary Examiner—Celia Chang
(74) Attorney, Agent, or Firm—Richard S. Echler, Sr.

(57) ABSTRACT

The present invention relates to compounds which comprise a 4-substituted piperidine ring linked to a substituted or unsubstituted hydrocarbyl ring. The compounds, including all enatiomeric and diasteriomeric forms and pharmaceutically acceptable salts thereof, have the formula:

wherein preferably R is substituted aryl, W is a pendant unit having the formula:

-L-Q

L is a linking unit, Q is preferably a cyclic hydrocarbyl unit; $W^1$ is preferably a carbocyclic unit and $W^2$ is a heteroatom comprising unit.

9 Claims, No Drawings

MELANOCORTIN RECEPTOR LIGANDS

CROSS REFERENCE TO RELATED APPLICATIONS

This application claims priority under Title 35, United States Code 119(e) from Provisional Application Ser. No. 60/376,585, filed Apr. 30, 2002.

FIELD OF THE INVENTION

The present invention relates to melanocortin (MC) receptor ligands that have a 4-substituted piperidine ring, which provides for enhanced activity. These ligands preferably exhibit selectivity for the MC-3 and/or MC-4 receptors relative to the other melanocortin receptors (in particular the MC-1 receptor) and are suitable for use in pharmaceutical compositions and in treatment methods.

BACKGROUND OF THE INVENTION

Melanocortin peptides (melanocortins) are natural peptide hormones in animals and man that bind to and stimulate MC receptors. Examples of melanocortins are α-MSH (melanocyte stimulating hormone), β-MSH, γ-MSH, ACTH (adrenocorticotropic hormone) and their peptide fragments. MSH is mainly known for its ability to regulate peripheral pigmentation, whereas ACTH is known to induce steroidoneogenesis. The melanocortin peptides also mediate a number of other physiological effects. They are reported to affect motivation, learning, memory, behavior, inflammation, body temperature, pain perception, blood pressure, heart rate, vascular tone, natriuresis, brain blood flow, nerve growth and repair, placental development, aldosterone synthesis and release, thyroxin release, spermatogenesis, ovarian weight, prolactin and FSH secretion, uterine bleeding in women, sebum and pheromone secretion, sexual activity, penile erection, blood glucose levels, intrauterine fetal growth, food motivated behavior, as well as other events related to parturition.

Both the MC-4 and MC-3 receptors have been localized to the hypothalamus, a region of the brain believed to be involved in the modulation of feeding behavior. Compounds showing selectivity for the MC-3/MC-4 receptors have been shown to alter food intake following intracerebroventricular and peripheral injection in rodents. Specifically, agonists have been shown to reduce feeding, while antagonists have been shown to increase feeding. The role of the MC-4 and MC-3 receptors have been defined in the control of body weight regulation in mammals. It is believed that the MC-3 receptor influences feed efficiency and the partitioning of fuel stores into fat, whereas the MC-4 receptor regulates food intake and possibly enery expenditure. Thus, these receptor subtypes appear to reduce body weight through distinct and complementary pathways. Therefore compounds that stimulate both the MC-3 and MC-4 receptors may have a greater weight loss effect than those that are selective for either the MC-3 or MC-4 receptor.

Body weight disorders such as obesity, anorexia and cachexia are widely recognized as significant public health issues and there is a need for compounds and pharmaceutical compositions which can treat these disorders.

The Applicants have discovered a class of compounds that surprisingly have high affinity for the MC-4 and/or the MC-3 receptor subtypes, and that are typically selective for these MC receptors relative to the other melanocortin receptor subtypes, particularly the MC-1 subtype.

SUMMARY OF THE INVENTION

The present invention relates to the surprising discovery that certain 4,4-disubstituted piperidines are affective as melanocortin receptor ligands. The compounds, including all enatiomeric and diasteriomeric forms and pharmaceutically acceptable salts thereof, have the formula:

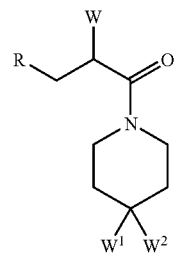

wherein R is a substituted or unsubstituted hydrocarbyl unit selected from the group consisting of:
  a) non-aromatic carbocyclic rings;
  b) aromatic carbocyclic rings;
  c) non-aromatic heterocyclic rings; and
  d) aromatic heterocyclic rings;
W is a pendant unit having the formula:

-L-Q wherein Q is hydrogen or a substituted or unsubstituted unit selected from:
  i) $C_1$–$C_{22}$ linear or branched alkyl;
  ii) $C_2$–$C_{22}$ linear or branched alkenyl;
  iii) $C_2$–$C_{22}$ linear or branched alkynyl;
  iv) $C_3$–$C_{13}$ aromatic heterocyclic rings;
  v) $C_3$–$C_8$ non-aromatic carbocyclic rings;
  vi) $C_6$–$C_{14}$ aromatic carbocyclic rings;
  vii) $C_1$–$C_7$ non-aromatic heterocyclic rings;
  viii) $C_3$–$C_{13}$ aromatic heterocyclic rings;
  xix) —$(CH_2)_m CO_2 R^8$;
  xx) —$(CH_2)_m C(O)N(R^8)_2$; and
  xxi) —$SO_2 R^9$;
  each $R^8$ is hydrogen; substituted or unsubstituted $C_1$–$C_6$ linear, branched, or cyclic alkyl; —OH; —$SO_2 R^9$, and mixtures thereof; $R^9$ is $C_1$–$C_4$ alkyl or phenyl; the index m is 0, 1, or 2;
L is a linking group having the formula:

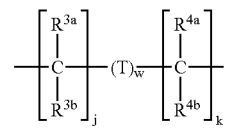

T is selected from the group consisting of:
  i) —$NR^6 S(O)_2$—;
  ii) —$S(O)_2 NR^6$—; and
  iii) mixtures thereof;
the index w is 0 or 1;
$R^{3a}$, $R^{3b}$, $R^{4a}$, and $R^{4b}$ are each independently:
  i) hydrogen;
  ii) $C_1$–$C_4$ linear, branched, and cyclic alkyl;
  iii) —$N(R^6)_2$;
  iv) —$NR^6 C(Y)R^6$;

v) $R^{3a}$ and $R^{3b}$ or $R^{4a}$, and $R^{4b}$ can be taken together to form a carbonyl unit; and
vi) mixtures thereof;
Y is —O—, —S—, =O, =S, =NR$^6$, =NOH, and mixtures thereof; the index j is from 0 to 3; the index k is from 0 to 3;
$W^1$ is a pendant unit having the formula:

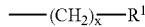

$R^1$ is:
i) hydrogen;
ii) $C_3$–$C_8$ substituted or unsubstituted non-aromatic carbocyclic rings;
iii) $C_6$–$C_{14}$ substituted or unsubstituted aromatic carbocyclic rings;
iv) $C_1$–$C_7$ substituted or unsubstituted non-aromatic heterocyclic rings; or
v) $C_3$–$C_{13}$ substituted or unsubstituted aromatic heterocyclic rings;
the index x is from 0 to 10;
W is a pendant unit having the formula:

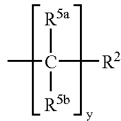

$R^2$ is:
i) hydrogen;
ii) $C_3$–$C_5$ non-aromatic carbocyclic rings;
iii) $C_6$–$C_{14}$ aromatic carbocyclic rings;
iv) $C_1$–$C_7$ non-aromatic heterocyclic rings;
v) $C_3$–$C_{13}$ aromatic heterocyclic rings;
vi) —C(Y)R$^6$;
vii) —C(Y)$_2$R$^6$;
viii) —C(Y)N(R$^6$)$_2$;
ix) —C(Y)NR$^6$N(R$^6$)$_2$;
x) —CN;
xi) —CNO;
xii) —[C(R$^7$)$_2$]C(R$^7$)$_2$;
xiii) —N(R$^6$)$_2$;
xiv) —NR$^6$CN;
xv) —NR$^6$C(Y)R$^6$;
xvi) —NR$^6$C(Y)N(R$^6$)$_2$;
xvii) —NHN(R$^6$)$_2$;
xviii) —NHOR$^6$;
xix) —NCS;
xx) —NO$_2$;
xxi) —OR$^6$;
xxii) —OCN;
xxiii) —OCF$_3$, —OCCl$_3$, —OCBr$_3$;
xxiv) —F, —Cl, —Br, —I, and mixtures thereof;
xxv) —SCN;
xxvi) —SO$_3$M;
xxvii) —OSO$_3$M;
xxviii) —SO$_2$N(R$^6$)$_2$;
xxix) —SO$_2$R$^6$;
xxx) —[C(R$^6$)$_2$]$_n$P(O)(OR$^6$)R$^6$;
xxxi) —[C(R$^6$)$_2$]$_n$P(O)(OR$^6$)$_2$;
xxxii) and mixtures thereof;

$R^{5a}$ and $R^{5b}$ are each hydrogen, or $R^{5a}$ and $R^{5b}$ are taken together to form a carbonyl unit;
Y is —O—, —S—, =O, =S, =NR$^6$, =NOH, and mixtures thereof; R$^6$ is hydrogen, $C_1$–$C_4$ linear, branched or cyclic alkyl, $C_2$–$C_4$ linear alkenyl, halogen, —OH, —NO$_2$, —CN, and mixtures thereof; M is hydrogen or a salt forming cation;
the index y is from 0 to 10.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to melanocortin (MC) receptor ligands. The melanocortin (MC) class of peptides mediates a wide range of physiological effects. Synthetic peptides and peptide mimetics, which modulate the interaction of natural MC ligands have varying degrees of selectivity and binding. The present invention is directed to ligands that are selective for the MC4 receptor, or that are selective for both the MC4 and MC3 receptor while minimizing the interaction at the MC1, MC2, and MC5 receptors.

For the purposes of the present invention the term "hydrocarbyl" is defined herein as any organic unit or moiety which is comprised of carbon atoms and hydrogen atoms. Included within the term hydrocarbyl are the heterocycles which are described herein below. Examples of various unsubstituted non-heterocyclic hydrocarbyl units include pentyl, 3-ethyloctanyl, 1,3-dimethylphenyl, cyclohexyl, cis-3-hexyl, 7,7-dimethylbicyclo[2.2.1]-heptan-1-yl, and naphth-2-yl.

Included within the definition of "hydrocarbyl" are the aromatic (aryl) and non-aromatic carbocyclic rings, non-limiting examples of which include cyclopropyl, cyclobutanyl, cyclopentanyl, cyclohexane, cyclohexenyl, cycloheptanyl, bicyclo-[0.1.1]-butanyl, bicyclo-[0.1.2]-pentanyl, bicyclo-[0.1.3]-hexanyl (thujanyl), bicyclo-[0.2.2]-hexanyl, bicyclo-[0.1.4]-heptanyl (caranyl), bicyclo-[2.2.1]-heptanyl (norboranyl), bicyclo-[0.2.4]-octanyl (caryophyllenyl), spiropentanyl, diclyclopentanespiranyl, decalinyl, phenyl, benzyl, naphthyl, indenyl, 2H-indenyl, azulenyl, phenanthryl, anthryl, fluorenyl, acenaphthylenyl, 1,2,3,4-tetrahydronaphthalenyl, and the like.

In addition, within the definition of "hydrocarbyl" is included the term "heterocycle." The term "heterocycle" includes both aromatic (heteroaryl) and non-aromatic heterocyclic rings non-limiting examples of which include: pyrrolyl, 2H-pyrrolyl, 3H-pyrrolyl, pyrazolyl, 2H-imidazolyl, 1,2,3-triazolyl, 1,2,4-triazolyl, isoxazolyl, oxazoyl, 1,2,4-oxadiazolyl, 2H-pyranyl, 4H-pyranyl, 2H-pyran-2-one-yl, pyridinyl, pyridazinyl, pyrimidinyl, pyrazinyl, piperazinyl, s-triazinyl, 4H-1,2-oxazinyl, 2H-1,3-oxazinyl, 1,4-oxazinyl, morpholinyl, azepinyl, oxepinyl, 4H-1,2-diazepinyl, indenyl 2H-indenyl, benzofuranyl, isobenzofuranyl, indolyl, 3H-indolyl, 1H-indolyl, benzoxazolyl, 2H-1-benzopyranyl, quinolinyl, isoquinolinyl, quinazolinyl, 2H-1,4-benzoxazinyl, pyrrolidinyl, pyrrolinyl, quinoxalinyl, furanyl, thiophenyl, benzimidazolyl, and the like each of which can be substituted or unsubstituted.

An example of a unit defined by the term "alkylenearyl" is a benzyl unit having the formula:

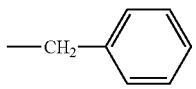

whereas an example of a unit defined by the term "alkyleneheteroaryl" is a 2-picolyl unit having the formula:

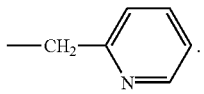

The terms "arylene" and "heteroarylene" relate to aryl and heteroaryl units which can serve as part of a linking group, for example, units having the formula:

 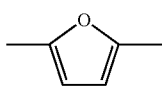

which represent an arylene and heteroarylene unit respectively.

The term "substituted" is used throughout the specification. The term "substituted" is defined herein as "encompassing moieties or units which can replace a hydrogen atom, two hydrogen atoms, or three hydrogen atoms of a hydrocarbyl moiety. Also substituted can include replacement of hydrogen atoms on two adjacent carbons to form a new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. An epoxide unit is an example of a substituted unit which requires replacement of a hydrogen atom on adjacent carbons. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of units which can serve as a replacement for hydrogen atoms when a hydrocarbyl unit is described as "substituted." Non-limiting examples include:
i) $-[C(R^6)_2]_p(CH=CH)_q R^6$; wherein p is from 0 to 12; q is from 0 to 12;
ii) $-C(Y)R^6$;
iii) $-C(Y)_2 R^6$;
iv) $-C(Y)CH=CH_2$;
v) $-C(Y)N(R^6)_2$;
vi) $-C(Y)NR^6 N(R^6)_2$;
vii) $-CN$;
viii) $-CNO$;
ix) $-CF_3$, $-CCl_3$, $-CBr_3$;
x) $-N(R^6)_2$;
xi) $-NR^6 CN$;
xii) $-NR^6 C(Y)R^6$;
xiii) $-NR^6 C(Y)N(R^6)_2$;
xiv) $-NHN(R^6)_2$;
xv) $-NHOR^6$;
xvi) $-NCS$;
xvii) $-NO_2$;
xviii) $-OR^6$;
xix) $-OCN$;
xx) $-OCF_3$, $-OCCl_3$, $-OCBr_3$;
xxi) $-F$, $-Cl$, $-Br$, $-I$, and mixtures thereof;
xxii) $-SCN$;
xxiii) $-SO_3 M$;
xxiv) $-OSO_3 M$;
xxv) $-SO_2 N(R^6)_2$;
xxvi) $-SO_2 R^6$;
xxvii) $-[C(R^7)_2]_n P(O)(OR^6)R^6$;
xxviii) $-[C(R^7)_2]_n P(O)(OR^6)_2$;
xxix) and mixtures thereof;

wherein $R^6$ is hydrogen, $C_1$–$C_4$ linear, branched, or cyclic alkyl, halogen, $-OH$, $-NO_2$, $-CN$, and mixtures thereof; $R^7$ is hydrogen or halogen, and mixtures thereof; M is hydrogen, or a salt forming cation; Y is $-O-$, $-S-$, $=O$, $=S$, $=NR^6$, $=NOH$, and mixtures thereof. Suitable salt forming cations include, sodium, lithium, potassium, calcium, magnesium, ammonium, and the like. Non-limiting examples of an alkylenearyl unit include benzyl, 2-phenylethyl, 3-phenylpropyl, 2-phenylpropyl.

The compounds of the present invention include all enatiomeric and diasteriomeric forms and pharmaceutically acceptable salts of compounds having the core scaffold represented by the formula:

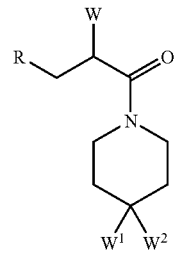

wherein R is a substituted or unsubstituted hydrocarbyl unit selected from the group consisting of:
a) non-aromatic carbocyclic rings;
b) aromatic carbocyclic rings;
c) non-aromatic heterocyclic rings;
d) aromatic heterocyclic rings.

A first aspect of R units relates to substituted and non-substituted aryl units wherein R units are substituted or unsubstituted phenyl, benzyl, naphthyl, and naphthalen-2-ylmethyl.

A first iteration of this aspect encompasses R units which are selected from the group consisting of phenyl, 4-fluorophenyl, 4-chlorophenyl, 4-hydroxyphenyl, and 4-methylphenyl. An example of this aspect which is particularly effective in enhancing MC-4 activity is 4-chlorophenyl, especially when combined with $W^1$ units comprising a carbocyclic ring, for example, cyclohexyl.

A second iteration of this aspect encompasses R units which are selected from the group consisting of 1-naphthyl, 2-naphthyl, naphthalen-1-ylmethyl, naphthalen-2-ylmethyl, and 1-hydroxynaphthalen-2-ylmethyl.

A second aspect of R units relates to substituted and non-substituted heteroaryl units wherein R units comprise substituted or unsubstituted quinolinyl, isoquinolinyl, tetrahydroquinolinyl, and tetrahydroisoquinolinyl.

A first iteration of this aspect encompasses R units which are 1,2,3,4-tetrahydroisoquinolinyl and 1,2,3,4-tetrahydroquinolinyl.

A second iteration of this aspect encompasses R units which are 6-hydroxy-1,2,3,4-tetrahydroisoquinolinyl and 6-hydroxy-1,2,3,4-tetrahydroquinolinyl.

Another aspect of R relates to phenyl rings comprising a $C_1$–$C_4$ alkyl unit, non-limiting examples of which include 4-methylphenyl, 2,4-dimethylphenyl, as well as mixed alkyl rings, inter alia, 2-methyl-4-isopropyl.

A yet further aspect of R relates to substituted or unsubstituted heteroaryl rings selected from the group consisting of thiophenyl, furanyl, oxazolyl, thiazolyl, pyrrolyl, and pyridinyl.

W is a pendant unit having the formula:

-L-Q wherein Q is hydrogen or a substituted or unsubstituted unit selected from:
  i) $C_1$–$C_{22}$ linear or branched alkyl;
  ii) $C_2$–$C_{22}$ linear or branched alkenyl;
  iii) $C_2$–$C_{22}$ linear or branched alkynyl;
  iv) $C_3$–$C_{13}$ aromatic heterocyclic rings;
  v) $C_3$–$C_9$ non-aromatic carbocyclic rings;
  vi) $C_6$–$C_{14}$ aromatic carbocyclic rings;
  vii) $C_1$–$C_7$ non-aromatic heterocyclic rings;
  viii) $C_3$–$C_{13}$ aromatic heterocyclic rings;
  xix) —$(CH_2)_mCO_2R^8$;
  xx) —$(CH_2)_mC(O)N(R^8)_2$; and
  xxi) —$SO_2R^9$;

each $R^8$ is hydrogen; substituted or unsubstituted $C_1$–$C_6$ linear, branched, or cyclic alkyl; —OH; —$SO_2R^9$, and mixtures thereof; $R^9$ is substituted or unsubstitute $C_1$–$C_4$ alkyl or phenyl; the index m is 0, 1, or 2. One $R^9$ iteration relates to units selected from the group consisting of methyl, ethyl, propyl, iso-propyl, and butyl. Another iteration includes haloalkyl, inter alia, trifluoromethyl.

Typically the number of rings which comprise Q are from 1 to 3. Aspects described herein include the substituted and unsubstituted mono-cyclic rings, inter alia, piperidine, pyrazine, pyrrolidine, imidazole, and the like, as well as fused-ring units, inter alia, quinoline, isoquinoline, indole, and the like. Examples of the various aspects of Q are described further herein below. All units which comprise Q can be substituted or unsubstituted by the units described herein above.

The first aspect of Q units relates to substituted or unsubstituted fused-ring heterocyclic units comprising 5 to 12 carbon atoms.

One iteration of this first aspect of Q units relates to substituted or unsubstituted fused ring heterocycles comprising one nitrogen atom, a first embodiment of which relates to quinoline or isoquinoline rings having the formula:

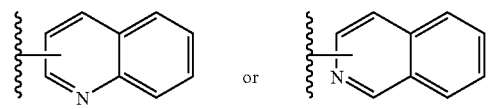

a second embodiment relates to units having the formula:

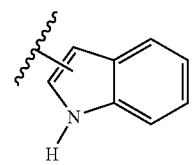

and a third embodiment relates to the tetrahydroquinoline and tetrahydroisoquinoline rings having the formula:

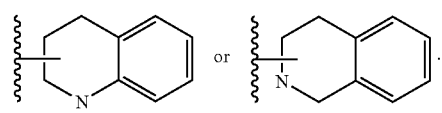

The second aspect of the present invention as it relates to Q units comprises nitrogen-atom containing six-member rings which can optionally further comprise a second nitrogen or other heteroatom, for example, the heteroaryl rings having the formulae:

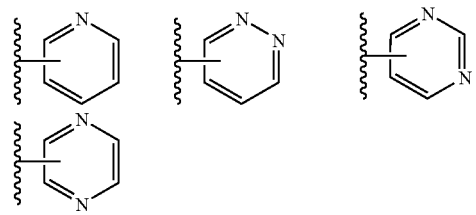

Other units included in this aspect include: morpholinyl, piperidinyl, triazinyl, and the like.

The third aspect of the Q units of the present invention relates to 5-member ring nitrogen atom containing heterocycles. A first iteration of the third aspect of Q relates to heterocycles selected from the group consisting of:
  i) thiazolyl, 2-methylthiazolyl, 4-mentylthiazolyl, 5-methylthiazolyl having the formula:

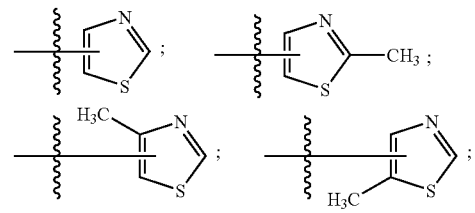

ii) 1,3,4-thiadiazolyl, 2-methyl-1,3,4-thiadiazolyl having the formula:

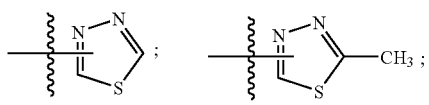

iii) 1,2,5-thiadiazolyl, 3-methyl-1,2,5-thiadiazolyl having the formula:

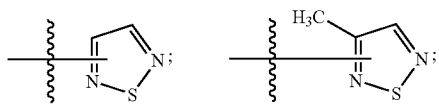

iv) oxazolyl, 2-methyloxazolyl, 4-methyloxazolyl, 5-methyloxazolyl having the formula:

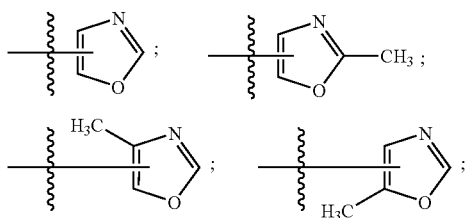

v) imidazolyl, 2-methylimidazolyl, 5-methylimidazolyl having the formula:

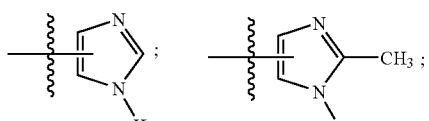

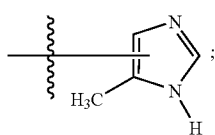

vi) 5-methyl-1,2,4-oxadiazolyl, 2-methyl-1,3,4-oxadiazolyl, 5-amino-1,2,4-oxadiazolyl, having the formula:

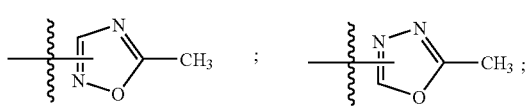

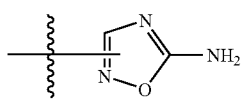

vii) 1,2-dihydro[1,2,4]triazol-3-one-1-yl, 2-methyl-1,2-dihydro[1,2,4]triazol-3-one-5-yl, having the formula:

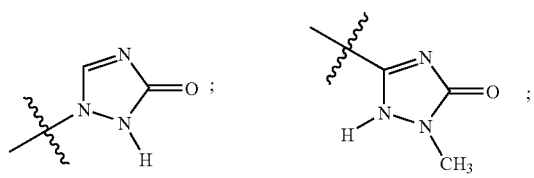

viii) oxazolidin-2-one-3-yl; 4,4-dimethyloxazolidin-2-one-3-yl; imidazolidin-2-one-1-yl; 1-methylimidazolidin-2-one-1-yl, having the formula:

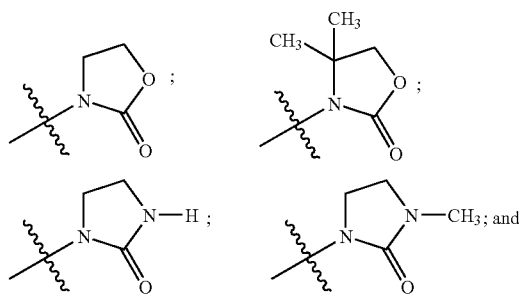

ix) 2-methyl-1,3,4-oxadiazolyl, 2-amino-1,3,4-oxadiazolyl, 2-(N,N-dimethylamino)-1,3,4-oxadiazolyl, having the formula:

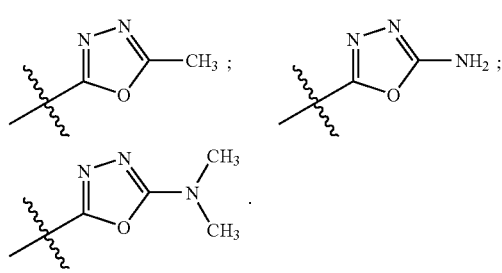

A second iteration of this aspect relates to R units which are selected from the group consisting of:

i) triazoles having the formula:

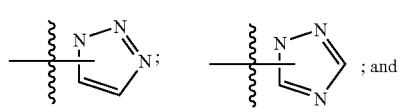

ii) tetrazole having the formula:

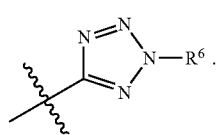

A yet other aspect of Q relates to units having the formula:
i) —$(CH_2)_m CO_2 R^8$; or
i) —$(CH_2)_m C(O)N(R^6)_2$;

each $R^8$ is hydrogen; substituted or unsubstituted $C_1$–$C_6$ linear, branched, or cyclic alkyl; —OH; —$SO_2 R^9$, and mixtures thereof; $R^9$ is $C_1$–$C_4$ alkyl or phenyl; the index m is 0, 1, or 2.

A first iteration of this aspect relates to Q units which are carboxylic acids.

A second iteration of this aspect relates to Q units which are amides, non-limiting examples of which include
i) $C(O)NHCH_3$;
ii) —$C(O)NHCH_2CH_3$;
ii) —$C(O)NHCH(CH_3)_2$;
iv) —$C(O)NHCH_2CH_2CH_3$;
v) —$C(O)NHCH_2CH_2CH_2CH_3$;
vi) —$C(O)NHCH_2CH(CH_3)_2$;
vii) —$C(O)NH_2$;
viii) —$C(O)NHCH_2CH=CHCH_3$;
xix) —$C(O)NHCH_2CH_2CH(CH_3)_2$; and
xx) —$C(O)NHCH_2C(CH_3)_3$.

A third iteration of this aspect relates to Q units which are substituted $C_1$–$C_6$ linear, branched, or cyclic alkyl; non-limiting examples of which include:
i) —$C(O)NHCH_2COH(CH_3)_2$;
ii) —$C(O)NHCH_2CNH_2(CH_3)_2$;
ii) —$C(O)NHCH_2CH(CH_3)NH_2$; and
iv) —$C(O)NHCH_2CH(CH_3)OH$;

L is a linking group having have the formula:

$$\left[\begin{array}{c} R^{3a} \\ | \\ -C- \\ | \\ R^{3b} \end{array}\right]_j -(T)_w- \left[\begin{array}{c} R^{4a} \\ | \\ -C- \\ | \\ R^{4b} \end{array}\right]_k$$

wherein T is selected from the group consisting of:
i) —$NR^6 S(O)_2$—;
ii) —$S(O)_2 NR^6$—; and
iii) mixtures thereof.

The index w is 0 or 1.

$R^{3a}$, $R^{3b}$, $R^{4a}$, and $R^{4b}$ are each independently:
i) hydrogen;
ii) $C_1$–$C_4$ linear, branched, and cyclic alkyl;
iii) —$N(R^6)_2$;
iv) —$NR^6 C(Y)R^6$;
v) $R^{3a}$ and $R^{3b}$ or $R^{4a}$ and $R^{4b}$ can be taken together to form a carbonyl unit; and
vi) mixtures thereof;

Y is —O—, —S—, =O, =S, =$NR^6$, =NOH, and mixtures thereof. $R^6$ is hydrogen, $C_1$–$C_4$ linear, branched or cyclic alkyl, halogen, —$NH_2$, —OH, —$NO_2$, —CN, and mixtures thereof;

The index j is from 0 to 3 and the index k is from 0 to 3.

A first aspect of L relates to linking groups wherein the index w is equal to 0 and the indices j and k are each equal to 1. This aspect relates to $R^{3a}$ and $R^{3b}$ and $R^{4a}$ and $R^{4b}$ units independently selected from:
i) hydrogen;
ii) methyl; and
iii) mixtures thereof;

wherein iterations of this aspect relate to linking groups which are alkylene units, non-limiting examples of which have the formula:

$$\begin{array}{c} H\ H \\ | \ | \\ -C-C- \\ | \ | \\ H\ H \end{array} \quad \begin{array}{c} H\ CH_3 \\ | \ | \\ -C-C- \\ | \ | \\ H\ H \end{array} \quad \begin{array}{c} CH_3\ H \\ | \ | \\ -C-C- \\ | \ | \\ H\ H \end{array}$$

$$\begin{array}{c} CH_3\ H \\ | \ | \\ -C-C- \\ | \ | \\ CH_3\ H \end{array} \quad \begin{array}{c} CH_3\ CH_3 \\ | \ | \\ -C-C- \\ | \ | \\ H\ CH_3 \end{array} \quad \begin{array}{c} H\ CH_3 \\ | \ | \\ -C-C- \\ | \ | \\ H\ CH_3 \end{array}$$

$$\begin{array}{c} CH_3\ H \\ | \ | \\ -C-C- \\ | \ | \\ CH_3\ CH_3 \end{array} \quad \begin{array}{c} CH_3\ CH_3 \\ | \ | \\ -C-C- \\ | \ | \\ CH_3\ CH_3 \end{array}.$$

Another aspect of linking groups relates to units comprising at least one unit having the formula:
i) —$N(R^6)_2$;
ii) —$NR^6 C(Y)R^6$; or
iii) $R^{3a}$ and $R^{3b}$ or $R^{4a}$, and $R^{4b}$ can be taken together to form a carbonyl unit;

non-limiting examples of iterations of which have the formula:

$$\begin{array}{c} H\ NH_2 \\ | \ | \\ -C-C- \\ | \ | \\ H\ H \end{array}, \quad \begin{array}{c} H\ NHCOCH_3 \\ | \ | \\ -C-C- \\ | \ | \\ H\ H \end{array},$$

$$\begin{array}{c} H\ NHCH_3 \\ | \ | \\ -C-C- \\ | \ | \\ H\ H \end{array}, \quad \begin{array}{c} O\ H \\ || \ | \\ -C-C- \\ \ | \\ H \end{array}, \quad \begin{array}{c} H\ H \\ | \ | \\ -C-C- \\ | \ | \\ NH_2\ NH_2 \end{array},$$

$$\begin{array}{c} H\ H \\ | \ | \\ -C-C- \\ | \ | \\ H\ NH \\ \ \ \ | \\ \ \ \ C \\ \ \ / \ \backslash \\ H_2 N\ \ \ NH \end{array} \quad \text{and} \quad \begin{array}{c} H\ NHOH \\ | \ | \\ -C-C- \\ | \ | \\ H\ H \end{array}.$$

Another aspect of linking units relates to L units which comprise units wherein the indices j and k are each equal to 0, the index w is 1 and T is a unit having the formula:

$$\begin{array}{c} O \\ || \\ -S-NH- \\ || \\ O \end{array} \quad \text{or} \quad \begin{array}{c} O \\ || \\ -NH-S- \\ || \\ O \end{array}$$

said units relating to Category I of compounds according to the present invention.

$W^1$ is a pendant unit having the formula:

—$(CH_2)_x$—$R^1$ $R^1$ is:
i) hydrogen;
ii) $C_3$–$C_8$ substituted or unsubstituted non-aromatic carbocyclic rings;

iii) $C_6$–$C_{14}$ substituted or unsubstituted aromatic carbocyclic rings;
iv) $C_1$–$C_7$ substituted or unsubstituted non-aromatic heterocyclic rings; or
v) $C_3$–$C_{13}$ substituted or unsubstituted aromatic heterocyclic rings;
the index x is from 0 to 10.

The first aspect of $W^1$ relates units having the formula: having the formula:

—$R^1$ wherein the index x is 0. The first embodiment of this aspect relates to $R^1$ units which are substituted or unsubstituted carbocyclic rings selected from the group consisting of cyclopropyl, cyclopentyl, cyclohexyl, 2-methylenecyclopentyl, and cycloheptyl.

A second embodiment of this aspect relates to $R^1$ units which are aromatic or non-aromatic heterocyclic rings selected from the group consisting of thiophen-2-yl, piperidin-4-yl, pyridin-2-yl, and morpholin-4-yl.

The second aspect of $W^1$ relates to units having the formula:

—$CH_2$—$R^1$ wherein the index x is 1. The first embodiment of this aspect relates to $R^1$ units which are substituted and unsubstituted carbocyclic rings selected from the group consisting of cyclopropyl, cyclopentyl, cyclohexyl, 2-methylenecyclopentyl, and cycloheptyl.

A second embodiment of this aspect relates to $R^1$ units which are aromatic or non-aromatic heterocyclic rings selected from the group consisting of thiophen-2-yl, piperidin-4-yl, pyridin-2-yl, and morpholin-4-yl.

$W^2$ is a pendant unit having the formula:

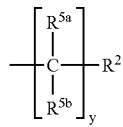

$R^2$ is:
i) hydrogen;
ii) $C_3$–$C_8$ non-aromatic carbocyclic rings;
iii) $C_6$–$C_{14}$ aromatic carbocyclic rings;
iv) $C_1$–$C_7$ non-aromatic heterocyclic rings;
v) $C_3$–$C_{13}$ aromatic heterocyclic rings;
vi) —C(Y)$R^6$;
vii) —C(Y)$_2R^6$;
viii) —C(Y)N($R^6$)$_2$;
ix) —C(Y)N$R^6$N($R^6$)$_2$;
x) —CN;
xi) —CNO;
xii) —[C($R^7$)$_2$]C($R^7$)$_2$;
xiii) —N($R^6$)$_2$;
xiv) —N$R^6$CN;
xv) —N$R^6$C(Y)$R^6$;
xvi) —N$R^6$C(Y)N($R^6$)$_2$;
xvii) —NHN($R^6$)$_2$;
xviii) —NHO$R^6$;
xix) —NCS;
xx) —NO$_2$;
xxi) —O$R^6$;
xxii) —OCN;
xxiii) —OCF$_3$, —OCCl$_3$, —OCBr$_3$;
xxiv) —F, —Cl, —Br, —I, and mixtures thereof;
xxv) —SCN;
xxvi) —SO$_3$M;
xxvii) —OSO$_3$M;
xxviii) —SO$_2$N($R^6$)$_2$;
xxix) —SO$_2R^6$;
xxx) —[C($R^6$)$_2$]$_n$P(O)(O$R^6$)$R_6$;
xxxi) —[C($R^6$)$_2$]$_n$P(O)(O$R^6$)$_2$;
xxxii) and mixtures thereof;

each pair of $R^{5a}$ and $R^{5b}$ are either both hydrogen, thereby forming a methylene unit —(CH$_2$)—, or $R^{5a}$ and $R^{5b}$ are taken together to form a carbonyl unit; Y is the same as above; $R^6$ is hydrogen, $C_1$–$C_4$ linear, branched or cyclic alkyl, $C_2$–$C_4$ linear alkenyl, halogen, —OH, —NO$_2$, —CN, and mixtures thereof; M is hydrogen or a salt forming cation.

The index y is from 0 to 10.

One aspect of the present invention relates to $W^2$ units which are short chain alkyl or alkenyl (lower hydrocarbyl) esters, $R^2$ having the formula:

—C(O)O$R^6$;

in one iteration $R^6$ is $C_1$–$C_4$ linear branched or cyclic alkyl or alkenyl. Non-limiting examples include —C(O)OCH$_3$; —C(O)OCH$_2$CH$_3$; —C(O)OCH$_2$CH$_2$CH$_3$; —C(O)OCH(CH$_3$)$_2$; —C(O)OCH$_2$CH$_2$CH$_2$CH$_3$; —C(O)OCH$_2$CH(CH$_3$)$_2$; —C(O)OCH$_2$CH═CHCH$_3$; —C(O)OCH$_2$CH$_2$CH(CH$_3$)$_2$; —C(O)OCH$_2$C(CH$_3$)$_3$; and the like.

Another aspect of the present invention relates to $R^2$ units which are short chain substituted or non-substituted amides having the formula:

—C(O)NH$R^6$ or —NHC(O)$R^6$ in one iteration $R^6$ is $C_1$–$C_4$ linear branched or cyclic alkyl or alkenyl. Non-limiting examples include —C(O)NHCH$_3$; —C(O)NHCH$_2$CH$_3$; —C(O)NHCH(CH$_3$)$_2$; —C(O)NHCH$_2$CH$_2$CH$_3$; —C(O)NHCH$_2$CH$_2$CH$_2$CH$_3$; —C(O)NHCH$_2$CH(CH$_3$)$_2$; —C(O)NH$_2$; —C(O)NHCH$_2$CH═CHCH$_3$; —C(O)NHCH$_2$CH$_2$CH(CH$_3$)$_2$; —C(O)NHCH$_2$C(CH$_3$)$_3$; —C(O)NHCH$_2$CH$_2$SCH$_3$; —C(O)NHCH$_2$CH$_2$OH; —NHC(O)CH$_3$; —NHC(O)CH$_2$CH$_3$; —NHC(O)—CH$_2$CH$_2$CH$_3$; and the like.

Another aspect of the present invention as it relates to $W^2$ units encompasses units having the formula:

—(CH$_2$)$_y$—$R^2$ wherein the index y is from 1 to 3.

A first iteration of this aspect relates to $R^2$ units which are heterocycles selected from the group consisting of:
i) thiazolyl, 2-methylthiazolyl, 4-mentylthiazolyl, 5-methylthiazolyl having the formula:

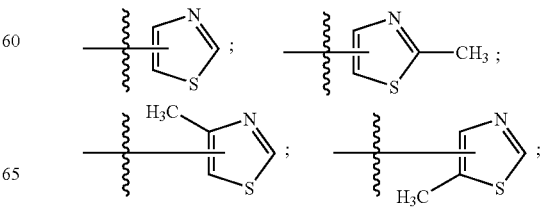

ii) 1,3,4-thiadiazolyl, 2-methyl-1,3,4-thiadiazolyl having the formula:

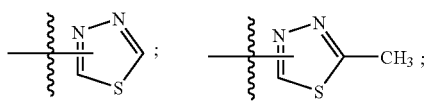

iii) 1,2,5-thiadiazolyl, 3-methyl-1,2,5-thiadiazolyl having the formula:

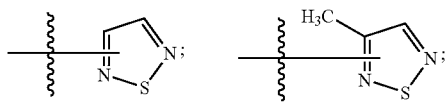

iv) oxazolyl, 2-methyloxazolyl, 4-methyloxazolyl, 5-methyloxazolyl having the formula:

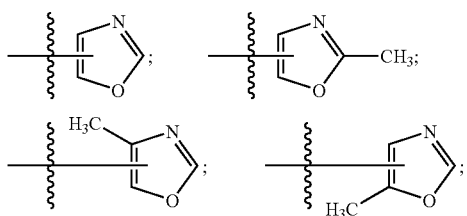

v) imidazolyl, 2-methylimidazolyl, 5-methylimidazolyl having the formula:

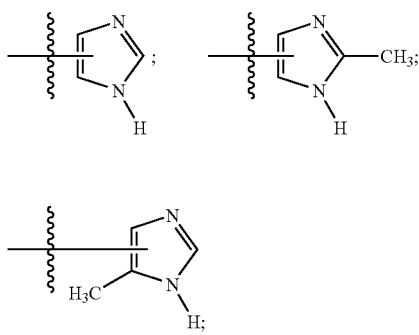

vi) 5-methyl-1,2,4-oxadiazolyl, 2-methyl-1,3,4-oxadiazolyl, 5-amino-1,2,4-oxadiazolyl, having the formula:

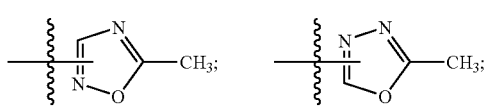

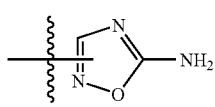

vii) 1,2-dihydro[1,2,4]triazol-3-one-1-yl, 2-methyl-1,2-dihydro[1,2,4]triazol-3-one-5-yl, having the formula:

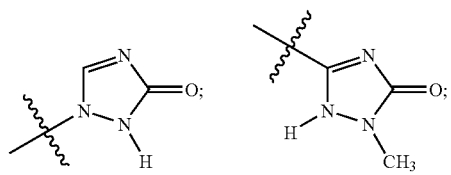

viii) oxazolidin-2-one-3-yl; 4,4-dimethyloxazolidin-2-one-3-yl; imidazolidin-2-one-1-yl; 1-methylimidazolidin-2-one-1-yl, having the formula:

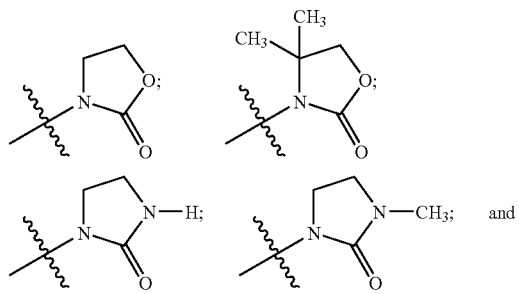

ix) 2-methyl-1,3,4-oxadiazolyl, 2-amino-1,3,4-oxadiazolyl, 2-(N,N-dimethylamino)-1,3,4-oxadiazolyl, having the formula:

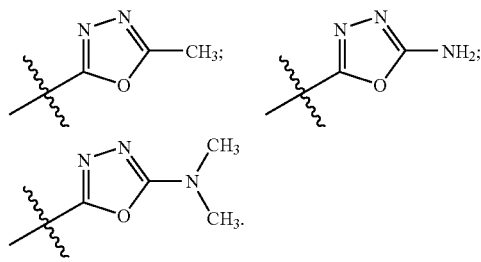

A second iteration of this aspect relates to $R^2$ units which are selected from the group consisting of:

i) triazoles having the formula:

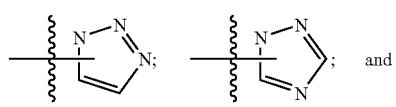

ii) tetrazole having the formula:

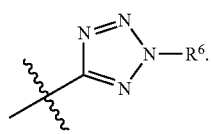

Non-limiting examples of scaffolds comprising the heterocycles of this aspect include:

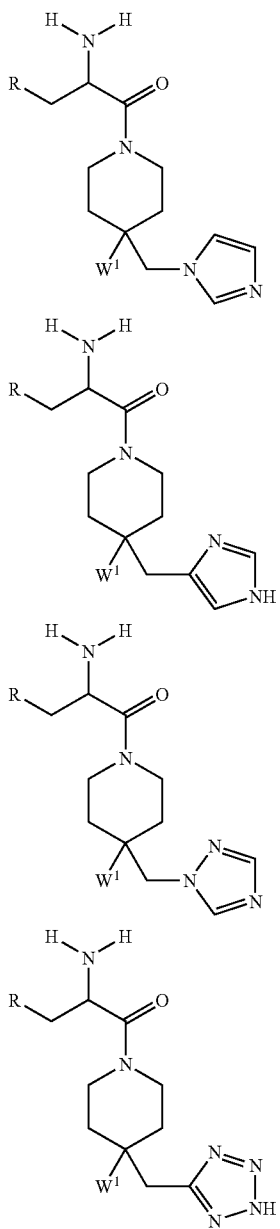

A further aspect of the present invention relates to $W^2$ units having the formula:

—(CH$_2$)$_y$—R$^2$ the index y is 1, 2, or 3 and $R^2$ is selected from the group consisting of:
a) —C(O)N(R$^7$)$_2$;
b) —C(O)NR$^7$N(R$^7$)$_2$;
c) —NR$^7$C(O)N(R$^7$)$_2$; and
d) —NR$^7$C(=NR$^7$)N(R$^7$)$_2$;

$R^4$ is hydrogen, methyl, and mixtures thereof; $R^7$ is hydrogen, methyl, —NO$_2$, —CN, and mixtures thereof.

Non-limiting examples of $W^2$ units comprising this aspect have the formula:
a) —(CH$_2$)$_y$NHC(O)NH$_2$;
b) —(CH$_2$)$_y$NHC(=NH)NH$_2$;
c) —(CH$_2$)$_y$NHC(=NCH$_3$)NHCN;
d) —(CH$_2$)$_y$NHC(=NNO$_2$)NHCN;
e) —(CH$_2$)$_y$NHC(=NCH$_3$)NHNO$_2$;
f) —(CH$_2$)$_y$NHC(=NCN)NHNO$_2$; and
g) —(CH$_2$)$_y$NHC(=NCN)NH$_2$;

wherein y is 1, 2, or 3. A first iteration includes $W^2$ units wherein y is equal to 3 and $R^2$ has the formula:

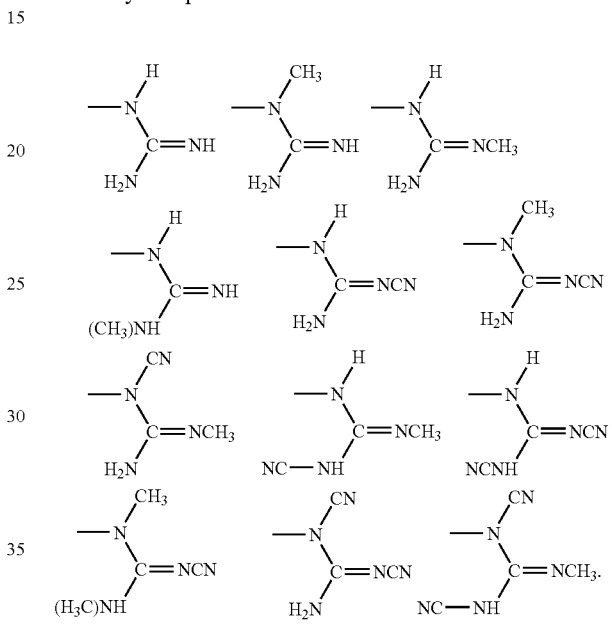

A further aspect of $R^2$ includes substituted or unsubstituted 6-member ring heterocycles selected from the group consisting of pyranyl, 1,4-dioxanyl, morpholinyl, pyridinyl, pyridazinyl, pyrimidinyl, pyrazinyl, piperidinyl, piperazinyl, triazinyl, 1,4-dithianyl, and thiomorpholinyl.

Preparation of Melanocortin Receptor Ligands

The following precursors can be used to prepare the melanocortin receptor ligands of the present invention.

A first precursor useful in preparing melanocortin receptor ligands relates to the hydroxy adduct: 4-cyclohexyl-4-hydroxymethyl-piperidine-1-carboxylic acid tert-butyl ester via the scheme outlined below.

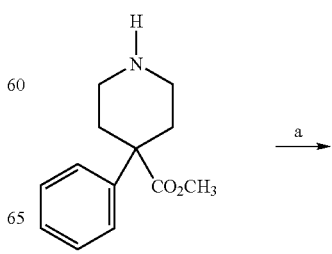

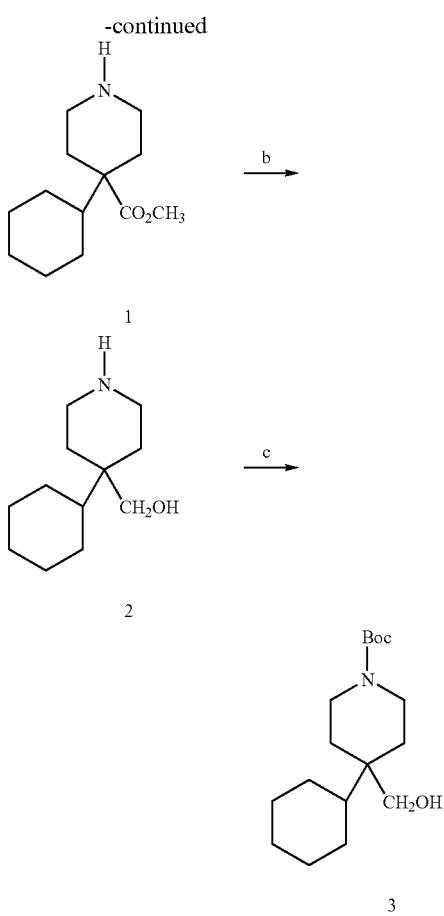

Reagents and conditions: (a) H₂: PtO₂; (b) LAH; (c) (Boc)₂O

Preparation of 4-cyclohexylpiperidine-4-carboxylic acid ethyl ester (1): To a solution of 4-phenylpiperidine-4-carboxylic acid ethyl ester (56 g, 248 mmol) in EtOH (700 mL) is added platinum (IV) oxide (10.2 g, 45 mmol) and concentrated hydrochloric acid. The Flask is purged with nitrogen and shaken on a Parr hydrogenation apparatus at 40 psig for 18 hours. The flask is removed and additional PtO₂ (2 g, 8.8 mmol) is added and hydrogenation is continued at 40 psig an additional 6 hours. The reaction solution is filtered to remove the catalyst and the filtrated is concentrated in vacuo to afford a residue which is partitioned between saturated NaHCO₃ and methylene chloride. The organic phase is removed and the aqueous phase washed several times with methylene chloride. The organic layers are combined, dried and concentrated under in vacuo to afford the desired product in nearly quantitative yield as a waxy solid. $^1$H NMR (300 MHz, CDCl₃) δ 0.90–1.45 (m, 6H), 1.25–1.32 (t, 3H), 1.55–1.85 (m, 7H), 2.15–2.28 (m, 2H), 2.98–2.80 (m, 2H), 3.18–3.27 (m, 2H), 4.10–4.25 (m, 2H), 7.10 (broad s, 1H); MS (ESI) m/z 240, (M+H⁺).

Preparation of (4-cyclohexylpiperidin-4-yl)-methanol (2): To a cooled (−5° C.) solution of lithium aluminum hydride (900 mL, 0.90 moles, 1.0M solution in THF) is added tetrahydrofuran (2000 mL) and 4-cyclohexyl-piperidine-4-carboxylic acid ethyl ester, 1, (59.5 g, 249 mmol). The resulting solution is stirred at between −5° C. and +3° C. for 1 hour and then allowed to warmed to room temperature and stir an additional sixty-six hours. The reaction is then re-cooled to 0° C. and carefully quenched with saturated ammonium chloride (100 mL). The reaction mixture is stirred for 10 minutes and then 87:10:3 ethyl acetate:methanol:triethylamine (500 mL) is added. The suspension is then stirred at room temperature for 20 minutes and filtered through a pad of Celite. The solids are re-suspended in 1:1 THF:EtOAc (2000 mL), stirred at room temperature for 1 hour and the suspension was again filtered through a pad of Celite. The filtrates are combined and concentrated in vacuo to afford 53.6 g of a mixture of the desired compound and 4-cyclohexyl-piperidine-4-carbaldehyde. The crude mixture is used directly in without further purification.

Preparation of 4-cyclohexyl-4-hydroxymethylpiperidine-1-carboxylic acid tert-butyl ester (3): Di-tert-butyl dicarbonate (79 g, 362 mmol) is added to a stirred solution of (4-cyclohexyl-piperidin-4-yl)-methanol, 2, (53.6 g) and triethylamine (180 mL) in MeOH (1600 mL) at 0° C. The resulting solution is allowed to warm to room temperature and is stirred an additional 4 hours. The solution concentrated in vacuo and purified via chromatography eluting with EtOAc/hexane 3:2, to afford 35.8 g (48% yield) of the desired product as a white solid. $^1$H NMR (300 MHz, CDCl₃) δ 1.00–1.32 (m, 5H), 1.35–1.60 (m, 14H), 1.65–1.88 (m, 5H), 3.15–3.30 (m, 2H), 3.48–3.65 (m, 2H), 3.63 (s, 2H); MS (ESI) m/z 298, (M+H⁺).

From intermediate compound 3, a series of other precursors useful in preparing melanocortin receptor ligands can be obtained. The mesylate 4 can be used to introduce a variety of 4-position-substituted piperidine, for example, triazole 5:

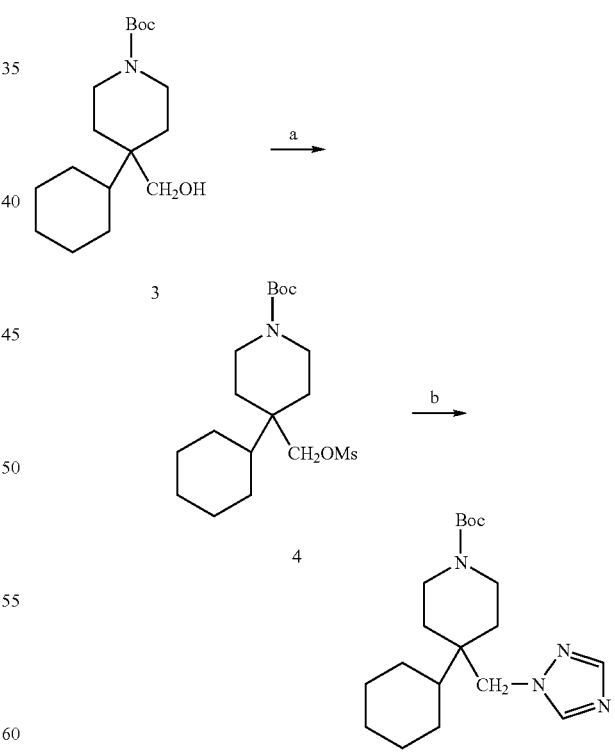

Reagents and conditions: (a) MsCl, Et₃N; (b) sodium triazole, DMF or azide 6 which can be used to introduce a variety of functional groups as further described herein below.

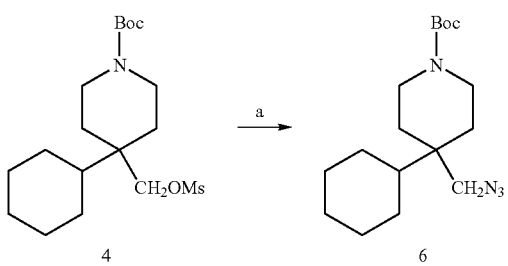

Reagents and conditions: (a) NaN₃, DMF

Preparation of 4-cyclohexyl-4-methanesulfonyloxymethylpiperidine-1-carboxylic acid tert-butyl ester (4): Methane sulfonyl chloride (1.8 mL, 23.0 mmol) is added to a stirred solution of 4-cyclohexyl-4-hydroxymethylpiperidine-1-carboxylic acid tert-butyl ester, 3, (3.42 g, 11.48 mmol) and triethylamine (4.8 mL, 2.8 mmol) in dichloromethane (30 mL) at 0° C. The reaction mixture is then allowed to warm to room temperature and stir for 1 hour. The reaction is quenched with a saturated solution of NaHCO₃ and the resulting mixture is extracted twice with dichloromethane (50 mL). The organic layers are combined, dried, filtered and concentrated in vacuo to yield the desired product in quantitative yield. The material is used for the next step without need for purification.

Preparation of 4-cyclohexyl-4-[1,2,4]triazol-1-ylmethyl-piperidine-1-carboxylic acid tert-butyl ester (5): To a solution of 4-cyclohexyl-4-methansulfonyloxymethyl-piperidine-1-carboxylic acid tert-butyl ester (39 g, 103.8 mmol) in N,N-dimethylformamide (200 mL) is added sodium triazole (38 g, 415.2 mmol). The resulting solution is heated to 100° C. for 24 hours then cooled to room temperature. The solvent is removed under reduce pressure and the crude product purified over silica (80:20 EtOAc:hexane) to afford 28.7 g (79.7% yield) of the desired compound as a colorless solid. ¹H NMR (CD₃OD) δ 0.95–1.90 (m, 15H), 1.46 (s, 9H), 3.45–3.55 (m, 4H), 4.34 (s, 2H), 7.99 (s, 1H), 8.48 (s, 1H). MS (ESI) m/z 349, (M+H⁺), 371(M+Na⁺)

Preparation of 4-cyclohexyl-4-azidomethylpiperidine-1-carboxylic acid tert-butyl ester (6): To a solution of 4-cyclohexyl-4-methanesulfonyloxymethyl-piperidine-1-carboxylic acid tert-butyl ester, 4, (2.42 g, 6.73 mmol) in DMF (25 mL) is added sodium azide (1.32 g, 20.2 mmol) and the mixture is heated and stirred at 100° C. over night. The reaction is cooled and then quenched with water. The resulting solution is extracted with EtOAc (30 mL), dried, filtered and concentrated in vacuo to afford the crude product as a brown oil which is purified via chromatography on silica gel eluting with hexane/EtOAc 3:1 to afford the desired product in 76% yield (1.91 g) as a colorless oil.

The intermediate aldehyde 7 can be used to prepare various W² units.

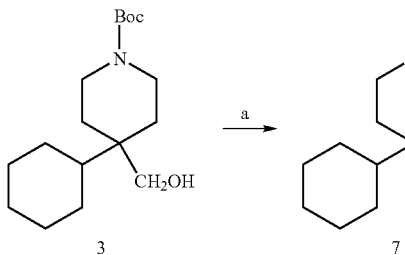

Reagans and conditions: (a) (CH₃CH₂CH₂)₄NRuO₄; 4 methylmorpholine N-oxide; 3 Å sieves rt, 1 hr.

Preparation of 4-cyclohexyl-4-formyl-piperidine-1-carboxylic acid tert-butyl ester (7): To a mixture of 4-cyclohexyl-4-hydroxymethyl-piperidine-1-carboxylic acid tert-butyl ester, 3, (1.0 g, 3.36 mmol), 4-methylmorpholine N-oxide (0.54 g, 4.64 mmol), and molecular sieves (0.5 g) in methylene chloride (20 mL) under argon atmosphere is added tetrapropylammonium perruthenate (35.5 mg) at room temperature. The mixture is stirred for 30 min to 1 hour after which the solution is filtered through a pad of silica and the solvent removed in vacuo to afford the desired product as a colorless oil, which is used without further purification. MS (ESI) m/z 318, (M+Na⁺).

The following are non-limiting examples of functional groups and functional group precursors which can be prepared from aldehyde 7.

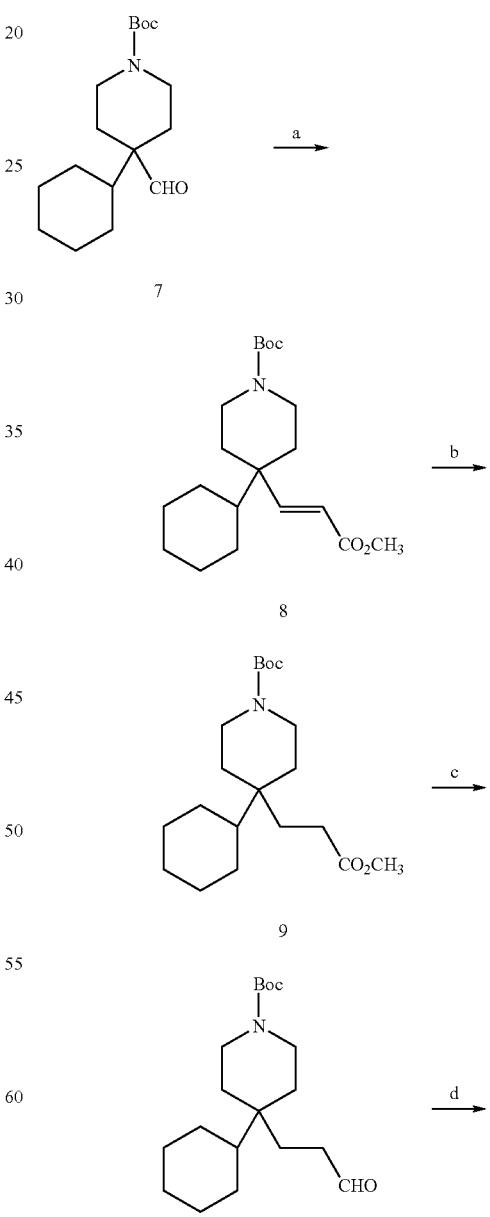

-continued

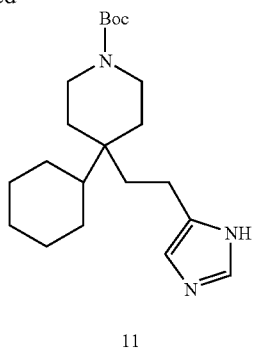

11

Reagents and conditions: (a) (CH₃O)₃P(O)CH₃CO₃CH₃, DBU, CH₃CN; rt, 1 hr. (b) H₂:Pd/C, MeOH; rt, 2 hr. (c) DIBAL, CH₂Cl₂; rt, 40 min. (d) TosMIC, NaCN, EtOH; rt, 3 hr.

Preparation of 4-cyclohexyl-4-(2-methoxycarbonyl-vinyl)-piperidine-1-carboxylic acid tert-butyl ester (8): To a solution of trimethyl phosphonoacetate (1.41 ml, 8.72 mmole), lithium chloride (477 mg, 11.3 mmole), and 1,8-diazabicyclo[4.3.0]non-7-ene (DBU) (1.55 ml, 11.3 mmole) in anhydrous acetonitrile (25 ml) is added 4-cyclohexyl-4-formyl-piperidine-1-carboxylic acid tert-butyl ester, 7, (2.58 mg, 8.72 mmole) under argon at room temperature. The mixture is stirred for one hour and the solvent then removed under reduced pressure. The crude product is purified over silica (methylene chloride:methanol=15:1, $R_f$=0.78) to afford 2.64 g (86% yield) of the desired compound.

Preparation of 4-cyclohexyl-4-(2-methoxycarbonyl-ethyl)-piperidine-1-carboxylic acid tert-butyl ester (9): To a solution of 4-cyclohexyl-4-(2-methoxycarbonyl-vinyl)-piperidine-1-carboxylic acid tert-butyl ester, 8, (2.64 g, 7.5 mmole) in methanol (30 ml) is added 10% palladium on carbon (120 mg) under argon. The mixture is purged with hydrogen and then stirred for two hours under a hydrogen atmosphere at atmospheric pressure. The reaction mixture is filtered through a short pad of Celite and the filtrate concentrated under reduced pressure. The crude product is purified over silica to afford 2.57 g (97% yield) of the desired compound.

Preparation of 4-cyclohexyl-4-(3-oxo-propyl)-piperidine-1-carboxylic acid tert-butyl ester (10): To a cooled (−78° C.) solution of 4-cyclohexyl-4-(2-methoxy-carbonylethyl)-piperidine-1-carboxylic acid tert-butyl ester, 9, (1.0 g, 2.833 mmol) in 40 ml of anhydrous methylene chloride is added diisobutylaluminum hydride (5.75 ml, 1 M, 5.75 mmol). The reaction is stirred at room temperature for 40 min before it is quenched by adding methanol (3 mL) and water (20 mL). The reaction mixture is warmed to room temperature and the organic layer separated, dried over sodium sulfate, filtered and concentrated in vacuo to afford 915 mg (>99% yield) of the desired compound as a colorless oil.

Preparation of 4-cyclohexyl-4-[2-(3H-imidazol-4-yl)-ethyl]-piperidine-1-carboxylic acid tert-butyl ester (11): A solution of 4-cyclohexyl-4-(3-oxo-propyl)-piperidine-1-carboxylic acid tert-butyl ester, 10, (300 mg, 0.93) in ethanol (10 ml) is treated with tosylmethyl isocyanide (tosMIC) (176 mg, 0.93 mmole) and sodium cyanide (6 mg) at room temperature for three hours. The solvent is removed under reduced pressure and ammonia in methanol (2M, 10 ml) added. The reaction is stirred in a sealed tube overnight. The reaction mixture is then concentrated under reduced pressure and the residue taken up in chloroform, washed with aqueous sodium bicarbonate, brine, then dried with sodium sulfate and concentrated to a red oil. The residue is purified over silica (methylene chloride:methanol=15:1, $R_f$=0.58) to afford 141 mg (42% yield) of the desired product.

The following scheme utilizes intermediate 3 for the preparation of other analogs intermediates and precursors.

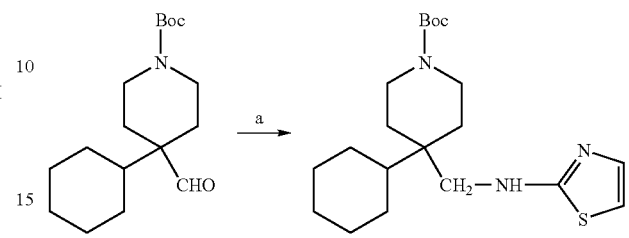

Reagents and conditions: (a) (i) 2-aminothiazole, toluene; reflux 18 hr; (ii) HB(AcO)₃, rt 3 hr.

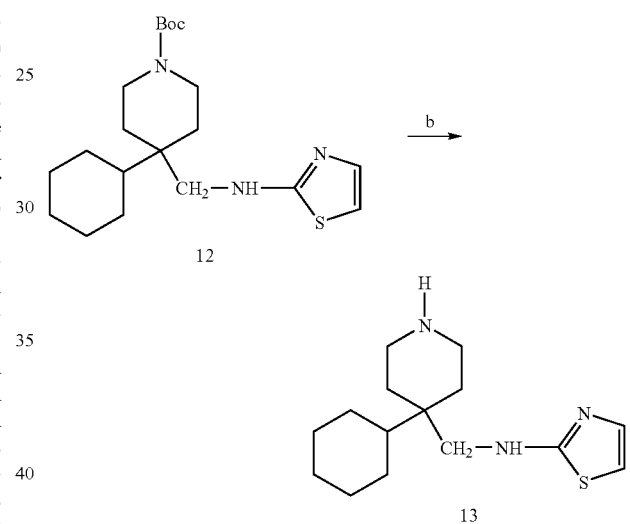

Reagents and Conditions: (b) TFA/CH₂Cl₂/H₂O; rt 1 hr.

Preparation of 4-cyclohexyl-4-(thiazol-2-ylaminomethyl)-piperidine-1-carboxylic acid tert-butyl ester (12): 4-Cyclohexyl-4-formyl-piperidine-1-carboxylic acid tert-butyl ester, 3, (296 mg, 1.0 mmol) and 2-aminothiazole (103 mg, 1.0 mmol) are dissolved in toluene (15 mL), and the mixture was refluxed using a Dean-Stark apparatus overnight. The solution is then cooled to room temperature and sodium triacetoxyborohydride added. The reaction is stirred at room temperature for three hours and then diluted with ethyl acetate. The reaction mixture is washed with aqueous sodium bicarbonate and brine. The solvent is removed under reduced pressure and the residue purified by preparative HPLC to afford 312 mg (82% yield) of the desired compound. MS (ESI) m/z 380 (M+H⁺)

Preparation of (4-cyclohexyl-piperidin-4-ylmethyl)-thiazol-2-yl-amine (13): A ready-to-use solution of trifluoroacetic acid:methylene chloride:water (1:1:0.1, 7 mL) is added to 4-cyclohexyl-4-(thiazol-2-ylaminomethyl)-piperidine-1-carboxylic acid tert-butyl ester, 12, (312 mg, 0.82 mmol), and the reaction mixture is stirred for 0.5–1.0 hour. The mixture is then concentrated under reduced pressure and partitioned between aqueous sodium bicarbonate and ethyl acetate. The organics are separated and the solvent removed under reduced pressure. The crude product is purified by preparative HPLC to afford 220 mg (96% yield) of the desired compound as the trifluoroacetic acid salt.

The following scheme utilizes intermediate 7 for the preparation of other intermediates and precursors.

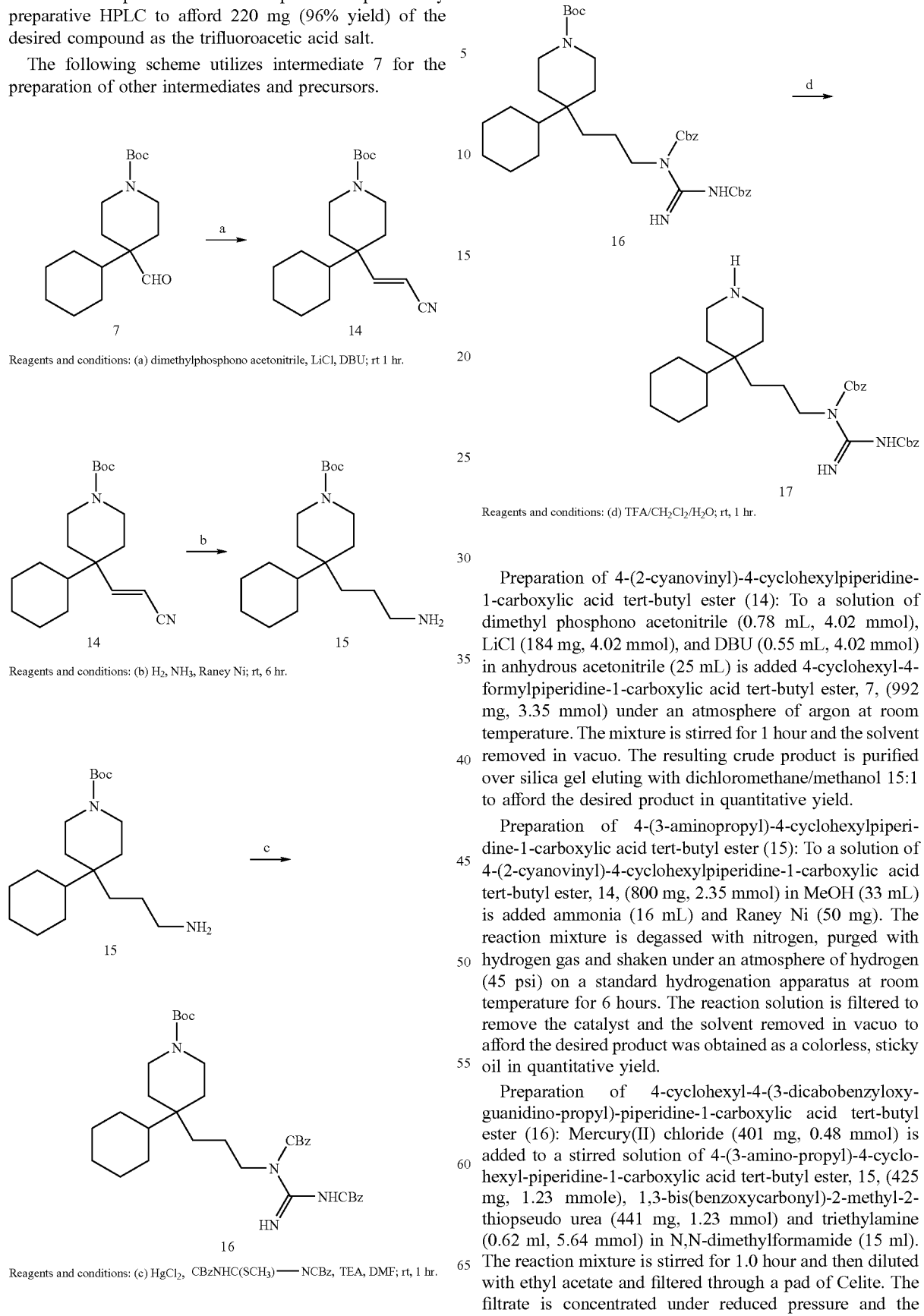

Preparation of 4-(2-cyanovinyl)-4-cyclohexylpiperidine-1-carboxylic acid tert-butyl ester (14): To a solution of dimethyl phosphono acetonitrile (0.78 mL, 4.02 mmol), LiCl (184 mg, 4.02 mmol), and DBU (0.55 mL, 4.02 mmol) in anhydrous acetonitrile (25 mL) is added 4-cyclohexyl-4-formylpiperidine-1-carboxylic acid tert-butyl ester, 7, (992 mg, 3.35 mmol) under an atmosphere of argon at room temperature. The mixture is stirred for 1 hour and the solvent removed in vacuo. The resulting crude product is purified over silica gel eluting with dichloromethane/methanol 15:1 to afford the desired product in quantitative yield.

Preparation of 4-(3-aminopropyl)-4-cyclohexylpiperidine-1-carboxylic acid tert-butyl ester (15): To a solution of 4-(2-cyanovinyl)-4-cyclohexylpiperidine-1-carboxylic acid tert-butyl ester, 14, (800 mg, 2.35 mmol) in MeOH (33 mL) is added ammonia (16 mL) and Raney Ni (50 mg). The reaction mixture is degassed with nitrogen, purged with hydrogen gas and shaken under an atmosphere of hydrogen (45 psi) on a standard hydrogenation apparatus at room temperature for 6 hours. The reaction solution is filtered to remove the catalyst and the solvent removed in vacuo to afford the desired product was obtained as a colorless, sticky oil in quantitative yield.

Preparation of 4-cyclohexyl-4-(3-dicabobenzyloxy-guanidino-propyl)-piperidine-1-carboxylic acid tert-butyl ester (16): Mercury(II) chloride (401 mg, 0.48 mmol) is added to a stirred solution of 4-(3-amino-propyl)-4-cyclohexyl-piperidine-1-carboxylic acid tert-butyl ester, 15, (425 mg, 1.23 mmole), 1,3-bis(benzoxycarbonyl)-2-methyl-2-thiopseudo urea (441 mg, 1.23 mmol) and triethylamine (0.62 ml, 5.64 mmol) in N,N-dimethylformamide (15 ml). The reaction mixture is stirred for 1.0 hour and then diluted with ethyl acetate and filtered through a pad of Celite. The filtrate is concentrated under reduced pressure and the residue purified over silica (methylene chloride/acetone, 3:1) to afford 629 mg (78% yield) of the desired compound as a colorless solid.

Preparation of N-[3-(4-cyclohexyl-piperidin-4-yl)-propyl]-dicarbobenzyloxy-guanidine (17): A ready-to-use solution of trifluoroacetic acid:methylene chloride:water (1:1:0.1, 11 ml) is added to 4-cyclohexyl-4-(3-dicarbobenzyloxy-guanidino-propyl)-piperidine-1-carboxylic acid tert-butyl ester, 16, (300 mg, 0.46 mmole), and the reaction mixture is stirred for 0.5–1.0 hour. The mixture is then concentrated under reduced pressure and partitioned between aqueous sodium bicarbonate and ethyl acetate. The organics are separated and concentrated under reduced pressure. The crude product is purified by preparative HPLC to afford 254 mg (>99% yield) of the desired compound.

The first aspect of Category I melanocortin receptor ligands according to the present invention comprises the 4-cyclohexylpiperidines having the general scaffold with the formula:

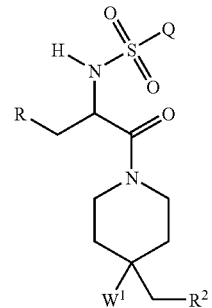

wherein $W^1$ comprises a carbocyclic ring, R, $R^2$, and Q are defined herein below in Table I.

TABLE I

| No. | R | $R^2$ | $W^1$ | Q |
|---|---|---|---|---|
| 1 | 4-chlorophenyl | [1,2,4]triazol-1-yl | cyclohexyl | methyl |
| 2 | 4-chlorophenyl | [1,2,4]triazol-1-yl | cyclohexyl | ethyl |
| 3 | 4-chlorophenyl | [1,2,4]triazol-1-yl | cyclohexyl | propyl |
| 4 | 4-chlorophenyl | [1,2,4]triazol-1-yl | cyclohexyl | iso-propyl |
| 5 | 4-chlorophenyl | [1,2,4]triazol-1-yl | cyclohexyl | butyl |
| 6 | 4-chlorophenyl | [1,2,4]triazol-1-yl | cyclohexyl | iso-butyl |
| 7 | 4-chlorophenyl | [1,2,4]triazol-1-yl | cyclohexyl | tert-butyl |
| 8 | 4-chlorophenyl | [1,2,4]triazol-1-yl | cyclohexyl | trifluoromethyl |
| 9 | 4-chlorophenyl | [1,2,4]triazol-1-yl | cyclohexyl | phenyl |
| 10 | 4-chlorophenyl | [1,2,4]triazol-1-yl | cyclohexyl | naphthalen-2-yl |
| 11 | 4-chlorophenyl | 2H-tetrazol-5-yl | cyclohexyl | methyl |
| 12 | 4-chlorophenyl | 2H-tetrazol-5-yl | cyclohexyl | ethyl |
| 13 | 4-chlorophenyl | 2H-tetrazol-5-yl | cyclohexyl | propyl |
| 14 | 4-chlorophenyl | 2H-tetrazol-5-yl | cyclohexyl | iso-propyl |
| 15 | 4-chlorophenyl | 2H-tetrazol-5-yl | cyclohexyl | butyl |
| 16 | 4-chlorophenyl | 2H-tetrazol-5-yl | cyclohexyl | iso-butyl |
| 17 | 4-chlorophenyl | 2H-tetrazol-5-yl | cyclohexyl | tert-butyl |
| 18 | 4-chlorophenyl | 2H-tetrazol-5-yl | cyclohexyl | trifluoromethyl |
| 19 | 4-chlorophenyl | 2H-tetrazol-5-yl | cyclohexyl | phenyl |
| 20 | 4-chlorophenyl | 2H-tetrazol-5-yl | cyclohexyl | 4-methylphenyl |
| 21 | 4-chlorophenyl | —NHC(=NH)$NH_2$ | cyclohexyl | methyl |
| 22 | 4-chlorophenyl | —NHC(=NH)$NH_2$ | cyclohexyl | ethyl |
| 23 | 4-chlorophenyl | —NHC(=NH)$NH_2$ | cyclohexyl | propyl |
| 24 | 4-chlorophenyl | —NHC(=NH)$NH_2$ | cyclohexyl | iso-propyl |
| 25 | 4-chlorophenyl | —NHC(=NH)$NH_2$ | cyclohexyl | butyl |
| 26 | 4-chlorophenyl | —NHC(=NH)$NH_2$ | cyclohexyl | iso-butyl |
| 27 | 4-chlorophenyl | —NHC(=NH)$NH_2$ | cyclohexyl | tert-butyl |
| 28 | 4-chlorophenyl | —NHC(=NH)$NH_2$ | cyclohexyl | trifluoromethyl |
| 29 | 4-chlorophenyl | —NHC(=NH)$NH_2$ | cyclohexyl | phenyl |
| 30 | 4-chlorophenyl | —NHC(=NH)$NH_2$ | cyclohexyl | naphthanen-2-yl |
| 31 | 4-chlorophenyl | —NHC(O)$NH_2$ | cyclohexyl | methyl |
| 32 | 4-chlorophenyl | —NHC(O)$NH_2$ | cyclohexyl | ethyl |
| 33 | 4-chlorophenyl | —NHC(O)$NH_2$ | cyclohexyl | propyl |
| 34 | 4-chlorophenyl | —NHC(O)$NH_2$ | cyclohexyl | iso-propyl |
| 35 | 4-chlorophenyl | —NHC(O)$NH_2$ | cyclohexyl | butyl |
| 36 | 4-chlorophenyl | —NHC(O)$NH_2$ | cyclohexyl | iso-butyl |
| 37 | 4-chlorophenyl | —NHC(O)$NH_2$ | cyclohexyl | tert-butyl |
| 38 | 4-chlorophenyl | —NHC(O)$NH_2$ | cyclohexyl | trifluoromethyl |
| 39 | 4-chlorophenyl | —NHC(O)$NH_2$ | cyclohexyl | phenyl |
| 40 | 4-chlorophenyl | —NHC(O)$NH_2$ | cyclohexyl | naphthanen-2-yl |
| 41 | 4-chlorophenyl | —NHC(=$NCH_3$)$NH_2$ | cyclohexyl | methyl |
| 42 | 4-chlorophenyl | —NHC(=$NCH_3$)$NH_2$ | cyclohexyl | ethyl |
| 43 | 4-chlorophenyl | —NHC(=$NCH_3$)$NH_2$ | cyclohexyl | propyl |
| 44 | 4-chlorophenyl | —NHC(=$NCH_3$)$NH_2$ | cyclohexyl | iso-propyl |
| 45 | 4-chlorophenyl | —NHC(=$NCH_3$)$NH_2$ | cyclohexyl | butyl |
| 46 | 4-chlorophenyl | —NHC(=$NCH_3$)$NH_2$ | cyclohexyl | iso-butyl |
| 47 | 4-chlorophenyl | —NHC(=$NCH_3$)$NH_2$ | cyclohexyl | tert-butyl |
| 48 | 4-chlorophenyl | —NHC(=$NCH_3$)$NH_2$ | cyclohexyl | trifluoromethyl |
| 49 | 4-chlorophenyl | —NHC(=$NCH_3$)$NH_2$ | cyclohexyl | phenyl |
| 50 | 4-chlorophenyl | —NHC(=$NCH_3$)$NH_2$ | cyclohexyl | naphthanen-2-yl |
| 51 | 4-chlorophenyl | —NHC(=NCN)$NHNO_2$ | cyclohexyl | methyl |
| 52 | 4-chlorophenyl | —NHC(=NCN)$NHNO_2$ | cyclohexyl | ethyl |

TABLE I-continued

| No. | R | R² | W¹ | Q |
|---|---|---|---|---|
| 53 | 4-chlorophenyl | —NHC(=NCN)NHNO₂ | cyclohexyl | propyl |
| 54 | 4-chlorophenyl | —NHC(=NCN)NHNO₂ | cyclohexyl | iso-propyl |
| 55 | 4-chlorophenyl | —NHC(=NCN)NHNO₂ | cyclohexyl | butyl |
| 56 | 4-chlorophenyl | —NHC(=NCN)NHNO₂ | cyclohexyl | iso-butyl |
| 57 | 4-chlorophenyl | —NHC(=NCN)NHNO₂ | cyclohexyl | tert-butyl |
| 58 | 4-chlorophenyl | —NHC(=NCN)NHNO₂ | cyclohexyl | trifluoromethyl |
| 59 | 4-chlorophenyl | —NHC(=NCN)NHNO₂ | cyclohexyl | phenyl |
| 60 | 4-chlorophenyl | —NHC(=NCN)NHNO₂ | cyclohexyl | naphthanen-2-yl |

The following is a scheme for preparing melanocortin receptor ligands of the first aspect of Category I. For illustrative purposes only, and not by way of limitation, this example utilizes R equal to 4-chlorophenyl, R² equal to [1,2,4]triazole-1-yl, W¹ equal to cyclohexyl, and Q equal to methyl.

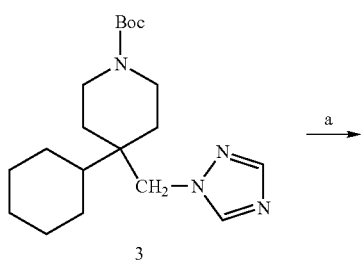

3

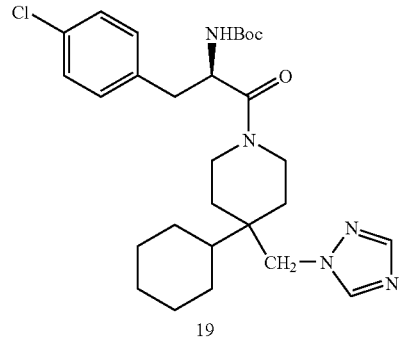

19

Reagents and conditions (b) HOBt, NMM, EDCI, DMF; rt, 6 hr.

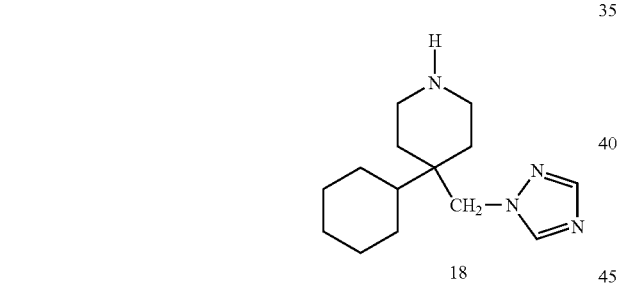

18

Reagents and conditions: (a) TFA/CH₂Cl₂/H₂O; rt 1 hr.

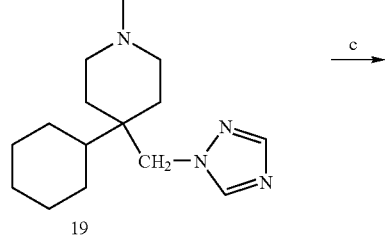

19

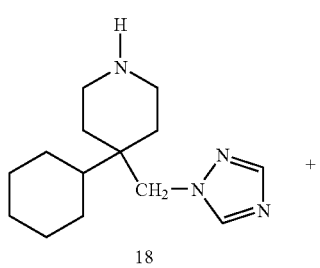

18
+

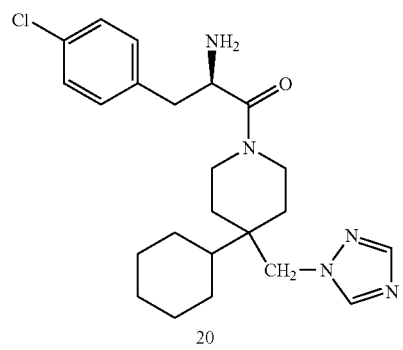

20

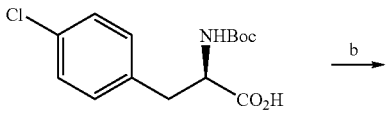

Reagents and conditions (b) TFA/CH₂Cl₂/H₂O; rt 1 hr.

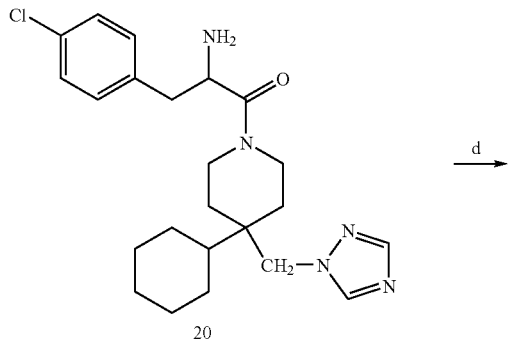

20

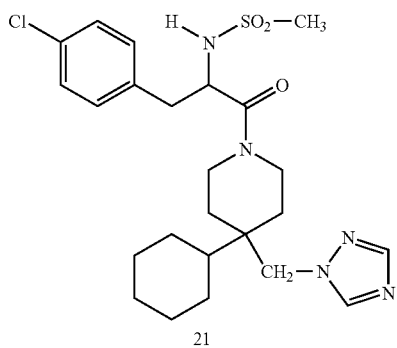

21

Reagents and conditions: (d) CH₃SO₂Cl, TEA, THF; 0° C. to rt, 18 hr.

EXAMPLE 1

N-[1-(R)-(4-Chlorobenzyl)-2-(4-cyclohexyl-4-[1,2,4]triazole-1-ylmethyl-piperidin-1-yl)-2-oxo-ethyl]-methanesulfonamide (21)

Preparation of 4-cyclohexyl-4-[1,2,4]triazole-1-ylmethylpiperidine (18): To a solution of trifluoroacetic acid/dichloromethane/water (1:1:0.1, 10 mL) is added 4-cyclohexyl-4-[1,2,4]triazole-1-ylmethyl-piperidine-1-carboxylic acid tert-butyl ester, 3, (3.5 g, 10 mmol) which was obtained in the procedure herein above and the reaction mixture is allowed to stir for 30 to 60 minutes. The reaction solution is then concentrated in vacuo and partitioned between aqueous NaHCO₃ and EtOAc. The organic phase is concentrated in vacuo and the crude product purified by HPLC over silica gel to afford the desired product.

Preparation of [1-(R)-(4-chlorobenzyl)-2-(4-cyclohexyl-4-[1,2,4]triazole-1-ylmethyl-piperidin-1-yl)-2-oxo-ethyl] carbamic acid tert-butyl ester (19): To a solution of 4-cyclohexyl-4-[1,2,4]triazole-1-ylmethylpiperidine, 18, (2.16 g, 8.74 mmol), (R)-2-N-(tert-butoxy-carbonyl)-amino-3-(4-chloro)phenyl-propanoic acid [Boc-D-Ph(p-Cl)—OH](2.65 g, 9.18 mmol), 1-hydroxy-benzotriazole (2.36 g, 17.5 mmol), N-methylmorpholine (35.0 mmol, 3.83 mL) in DMF (30 mL) is added in portions 1-(3-dimethylaminopropyl)-3-ethylcarbodiimide hydrochloride (2.16 g, 11.4 mmol). The reaction is allowed to stir for 6 hours after which it is quenched by adding aqueous NH₄Cl. The reaction mixture is extracted with EtOAc and the combined layers are dried, concentrated in vacuo, and the resulting crude product purified over silica gel to afford the desired product.

Preparation of 2-(R)-amino-3-(4-chlorophenyl)-1-(4-cyclohexyl-4-[[1,2,4]triazole-1-ylmethyl-piperidin-1-yl)propan-1-one (20): A solution of trifluoroacetic acid/dichloromethane/water (1:1:0.1, 5 ml) is added to (1-(R)-(4-chlorobenzyl)-2-(4-cyclohexyl-4-[1,2,4]triazole-1-ylmethyl-piperidin-1-yl)-2-oxo-ethyl]carbamic acid tert-butyl ester, 19, (3.5 g, 6.65 mmol) and the reaction mixture is allowed to stir for 30 to 60 minutes. The reaction solution is then concentrated in vacuo and partitioned between aqueous NaHCO₃ and EtOAc. The organic phase is concentrated in vacuo and the crude product purified via HPLC over silica gel to afford the desired product.

Preparation of N-[1-(R)-(4-chlorobenzyl)-2-(4-cyclohexyl-4-[1,2,4]triazol-1-ylmethyl-piperidin-1-yl)-2-oxo-ethyl]-methanesulfonamide (21): To a solution of 2-(R)-amino-3-(4-chlorophenyl)-1-(4-cyclohexyl-4-[1,2,4]triazol-1-ylmethyl-piperidin-1-yl)-propan-1-one, 20, (400 mg, 0.93 mmol) in tetrahydrofuran (10 mL) at 0° C. is added triethylamine (0.78 mL, 5.58 mmol) and methanesulfonyl chloride (0.09 mL, 1.11 mmol). The resulting suspension is allowed to stir at room temperature overnight and the solvent removed under reduced pressure. The crude product is purified by preparative HPLC to afford 314.5 mg (54% yield) of the desired compound as the trifluoroacetic acid salt. $^1$H NMR (300 MHz, CD₃OD) δ 0.80–1.92 (m, 15H), 2.78–3.08 (m, 5H), 3.30–3.90 (m, 4H), 4.25–4.40 (m, 2H), 4.65–4.75 (m, 1H), 7.25–7.40 (m, 4H), 8.00–8.08 (m, 1H), 8.52 (s, 1H).

$^{13}$C NMR (75 MHz, CD₃OD) ppm 27.75, 27.79, 27.85, 27.96, 28.55, 31.08, 31.76, 39.31, 39.41, 40.16, 40.49, 41.89, 42.96, 43.82, 52.61, 53.28, 54.62, 55.29, 130.08, 130.22, 132.81, 132.92, 134.40, 134.58, 136.86, 137.04, 146.62, 151.80, 151.94, 172.50. (rotamers present); $^{19}$F NMR (282 MHz, CD₃OD) ppm 85.60, 92.52. MS (ESI) m/z 508, (M+H⁺). Anal. Calcd. for $C_{24}H_{34}N_5O_3ClS$ 0.30 TFA: C, 54.49; H, 6.37; N, 2.91. Found: C, 54.46; H, 5.93; N, 11.97.

Other W¹ units which can suitably replace cyclohexyl include, cyclopropyl, cyclopropylmethyl, cyclopentyl, cyclopentanone-2-yl, and cycloheptanyl.

Non-limiting examples of other analogs of Category I which can be prepared by this process include:

N-[1-(R)-(4-chlorobenzyl)-2-(4-cyclohexyl-4-[1,2,4]triazole-1-ylmethyl-piperidin-1-yl)-2-oxo-ethyl]-ethanesulfonamide;

N-[1-(R)-(4-chlorobenzyl)-2-(4-cyclohexyl-4-[1,2,4]triazole-1-ylmethyl-piperidin-1-yl)-2-oxo-ethyl]-propanesulfonamide;

N-[1-(R)-(4-chlorobenzyl)-2-(4-cyclohexyl-4-[1,2,4]triazole-1-ylmethyl-piperidin-1-yl)-2-oxo-ethyl]-isopropanesulfonamide;

N-[1-(R)-(4-chlorobenzyl)-2-(4-cyclohexyl-4-[1,2,4]triazole-1-ylmethyl-piperidin-1-yl)-2-oxo-ethyl]-trifluoromethanesulfonamide;

N-[1-(R)-(4-chlorobenzyl)-2-(4-cyclohexyl-4-[1,2,4]triazole-1-ylmethyl -piperidin-1-yl)-2-oxo-ethyl]-phenylsulfonamide N-[1-(R)-(4-chlorobenzyl)-2-(4-cyclohexyl-4-[1,2,4]triazole-1-ylmethyl-piperidin-1-yl)-2-oxo-ethyl]-(4-methylphenyl)sulfonamide; and N-[1-(R)-(4-chlorobenzyl)-2-(4-cyclohexyl-4-[1,2,4]triazole-1-ylmethyl-piperidin-1-yl)-2-oxo-ethyl]-naphthalen-2-ylsulfonamide.

The second aspect of Category I melanocortin receptor ligands according to the present invention comprises the 4-cyclohexylpiperidines having the general scaffold with the formula:

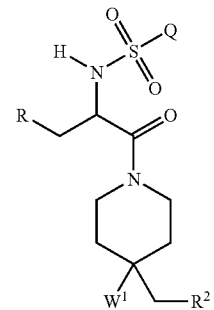

wherein $W^1$ comprises a heterocyclic ring, R, $R^2$, and Q are defined herein below in Table II.

TABLE II

| No. | R | $R^2$ | $W^1$ | Q |
|---|---|---|---|---|
| 61 | 4-chlorophenyl | [1,2,4]triazol-1-yl | piperidin-1-yl | methyl |
| 62 | 4-chlorophenyl | [1,2,4]triazol-1-yl | piperidin-1-yl | ethyl |
| 63 | 4-chlorophenyl | [1,2,4]triazol-1-yl | piperidin-1-yl | propyl |
| 64 | 4-chlorophenyl | [1,2,4]triazol-1-yl | piperidin-1-yl | iso-propyl |
| 65 | 4-chlorophenyl | [1,2,4]triazol-1-yl | piperidin-1-yl | butyl |
| 66 | 4-chlorophenyl | [1,2,4]triazol-1-yl | piperidin-1-yl | iso-butyl |
| 67 | 4-chlorophenyl | [1,2,4]triazol-1-yl | piperidin-1-yl | tert-butyl |
| 68 | 4-chlorophenyl | [1,2,4]triazol-1-yl | piperidin-1-yl | trifluoromethyl |
| 69 | 4-chlorophenyl | [1,2,4]triazol-1-yl | piperidin-1-yl | phenyl |
| 70 | 4-chlorophenyl | [1,2,4]triazol-1-yl | piperidin-1-yl | 4-methylphenyl |
| 71 | 4-chlorophenyl | 2H-tetrazol-5-yl | piperidin-1-yl | methyl |
| 72 | 4-chlorophenyl | 2H-tetrazol-5-yl | piperidin-1-yl | ethyl |
| 73 | 4-chlorophenyl | 2H-tetrazol-5-yl | piperidin-1-yl | propyl |
| 74 | 4-chlorophenyl | 2H-tetrazol-5-yl | piperidin-1-yl | iso-propyl |
| 75 | 4-chlorophenyl | 2H-tetrazol-5-yl | piperidin-1-yl | butyl |
| 76 | 4-chlorophenyl | 2H-tetrazol-5-yl | piperidin-1-yl | iso-butyl |
| 77 | 4-chlorophenyl | 2H-tetrazol-5-yl | piperidin-1-yl | tert-butyl |
| 78 | 4-chlorophenyl | 2H-tetrazol-5-yl | piperidin-1-yl | trifluoromethyl |
| 79 | 4-chlorophenyl | 2H-tetrazol-5-yl | piperidin-1-yl | phenyl |
| 80 | 4-chlorophenyl | 2H-tetrazol-5-yl | piperidin-1-yl | 4-methylphenyl |
| 81 | 4-chlorophenyl | —NHC(=NH)NH$_2$ | piperidin-1-yl | methyl |
| 82 | 4-chlorophenyl | —NHC(=NH)NH$_2$ | piperidin-1-yl | ethyl |
| 83 | 4-chlorophenyl | —NHC(=NH)NH$_2$ | piperidin-1-yl | propyl |
| 84 | 4-chlorophenyl | —NHC(=NH)NH$_2$ | piperidin-1-yl | iso-propyl |
| 85 | 4-chlorophenyl | —NHC(=NH)NH$_2$ | piperidin-1-yl | butyl |
| 86 | 4-chlorophenyl | —NHC(=NH)NH$_2$ | piperidin-1-yl | iso-butyl |
| 87 | 4-chlorophenyl | —NHC(=NH)NH$_2$ | piperidin-1-yl | tert-butyl |
| 88 | 4-chlorophenyl | —NHC(=NH)NH$_2$ | piperidin-1-yl | trifluoromethyl |
| 89 | 4-chlorophenyl | —NHC(=NH)NH$_2$ | piperidin-1-yl | phenyl |
| 90 | 4-chlorophenyl | —NHC(=NH)NH$_2$ | piperidin-1-yl | naphthanen-2-yl |
| 91 | 4-chlorophenyl | —NHC(O)NH$_2$ | piperidin-1-yl | methyl |
| 92 | 4-chlorophenyl | —NHC(O)NH$_2$ | piperidin-1-yl | ethyl |
| 93 | 4-chlorophenyl | —NHC(O)NH$_2$ | piperidin-1-yl | propyl |
| 94 | 4-chlorophenyl | —NHC(O)NH$_2$ | piperidin-1-yl | iso-propyl |
| 95 | 4-chlorophenyl | —NHC(O)NH$_2$ | piperidin-1-yl | butyl |
| 96 | 4-chlorophenyl | —NHC(O)NH$_2$ | piperidin-1-yl | iso-butyl |
| 97 | 4-chlorophenyl | —NHC(O)NH$_2$ | piperidin-1-yl | tert-butyl |
| 98 | 4-chlorophenyl | —NHC(O)NH$_2$ | piperidin-1-yl | trifluoromethyl |
| 99 | 4-chlorophenyl | —NHC(O)NH$_2$ | piperidin-1-yl | phenyl |
| 100 | 4-chlorophenyl | —NHC(O)NH$_2$ | piperidin-1-yl | naphthanen-2-yl |
| 101 | 4-chlorophenyl | —NHC(=NCH$_3$)NH$_2$ | piperidin-1-yl | methyl |
| 102 | 4-chlorophenyl | —NHC(=NCH$_3$)NH$_2$ | piperidin-1-yl | ethyl |
| 103 | 4-chlorophenyl | —NHC(=NCH$_3$)NH$_2$ | piperidin-1-yl | propyl |
| 104 | 4-chlorophenyl | —NHC(=NCH$_3$)NH$_2$ | piperidin-1-yl | iso-propyl |
| 105 | 4-chlorophenyl | —NHC(=NCH$_3$)NH$_2$ | piperidin-1-yl | butyl |
| 106 | 4-chlorophenyl | —NHC(=NCH$_3$)NH$_2$ | piperidin-1-yl | iso-butyl |
| 107 | 4-chlorophenyl | —NHC(=NCH$_3$)NH$_2$ | piperidin-1-yl | tert-butyl |
| 108 | 4-chlorophenyl | —NHC(=NCH$_3$)NH$_2$ | piperidin-1-yl | trifluoromethyl |
| 109 | 4-chlorophenyl | —NHC(=NCH$_3$)NH$_2$ | piperidin-1-yl | phenyl |
| 110 | 4-chlorophenyl | —NHC(=NCH$_3$)NH$_2$ | piperidin-1-yl | naphthanen-2-yl |
| 111 | 4-chlorophenyl | —NHC(=NCN)NHNO$_2$ | piperidin-1-yl | methyl |

TABLE II-continued

| No. | R | R² | W¹ | Q |
|-----|---|-----|-----|---|
| 112 | 4-chlorophenyl | —NHC(=NCN)NHNO₂ | piperidin-1-yl | ethyl |
| 113 | 4-chlorophenyl | —NHC(=NCN)NHNO₂ | piperidin-1-yl | propyl |
| 114 | 4-chlorophenyl | —NHC(=NCN)NHNO₂ | piperidin-1-yl | iso-propyl |
| 115 | 4-chlorophenyl | —NHC(=NCN)NHNO₂ | piperidin-1-yl | butyl |
| 116 | 4-chlorophenyl | —NHC(=NCN)NHNO₂ | piperidin-1-yl | iso-butyl |
| 117 | 4-chlorophenyl | —NHC(=NCN)NHNO₂ | piperidin-1-yl | tert-butyl |
| 118 | 4-chlorophenyl | —NHC(=NCN)NHNO₂ | piperidin-1-yl | trifluoromethyl |
| 119 | 4-chlorophenyl | —NHC(=NCN)NHNO₂ | piperidin-1-yl | phenyl |
| 120 | 4-chlorophenyl | —NHC(=NCN)NHNO₂ | piperidin-1-yl | naphthanen-2-yl |

The following is a scheme for preparing melanocortin receptor ligands of the first aspect of Category I. For illustrative purposes only, and not by way of limitation, this example utilizes R equal to 4-chlorophenyl, R² equal to [1,2,4]triazole-1-yl, W¹ equal to piperidin-4-yl, and Q equal to methyl.

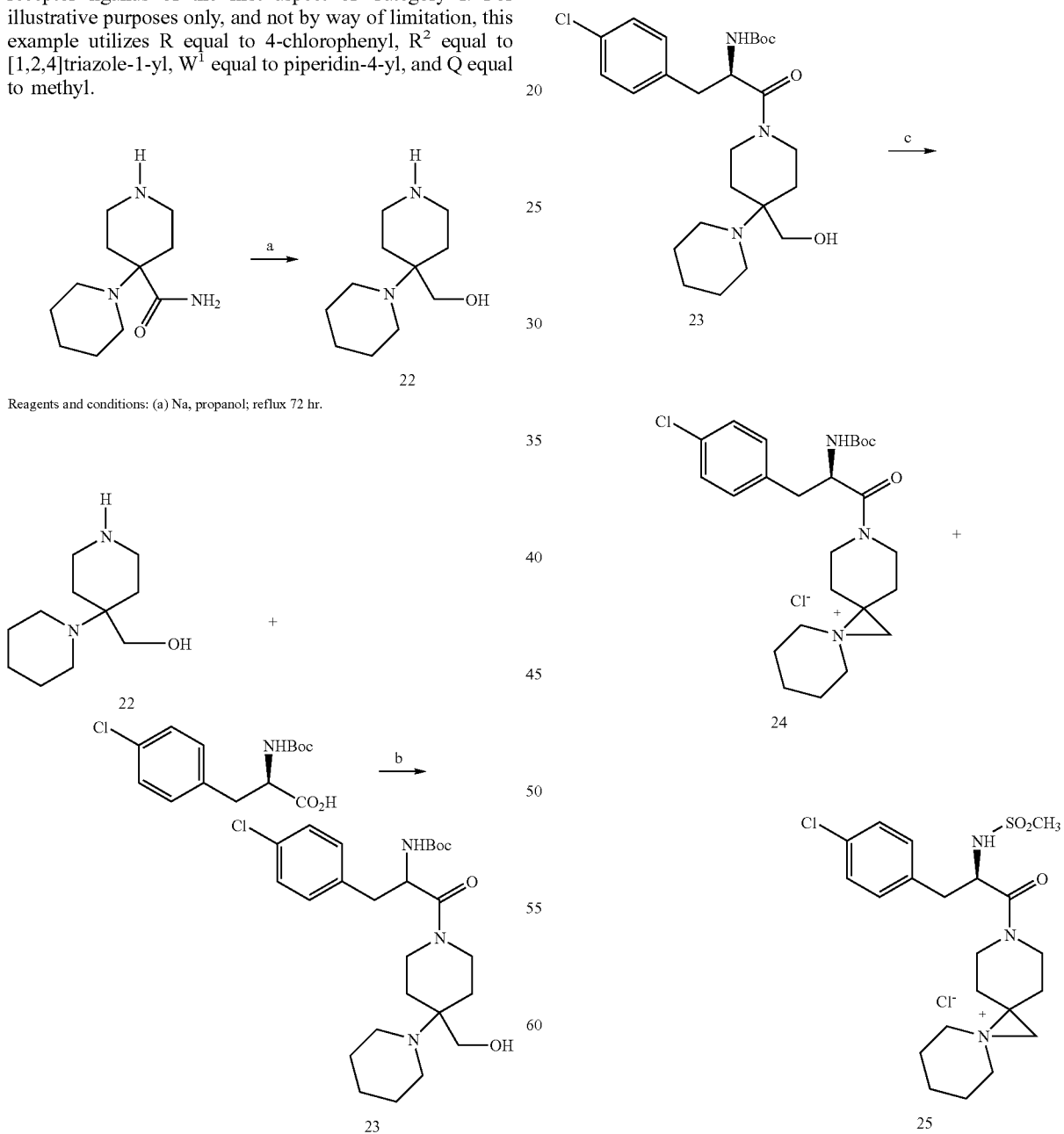

Reagents and conditions: (a) Na, propanol; reflux 72 hr.

Reagents and conditions: (b) HOBt, NMM, EDCI, DMF, DIPEA; 0° C. to rt, 18 hr.

Reagents and conditions: (c) CH₃SO₂Cl, TEA, CH₂Cl₂; 0° C. to rt, 18 hr.

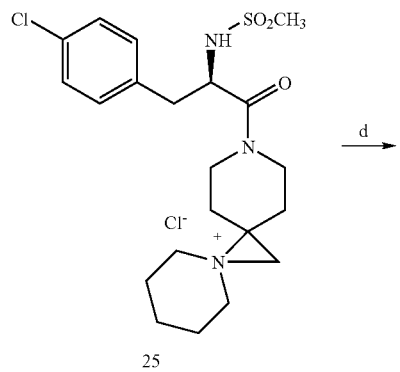

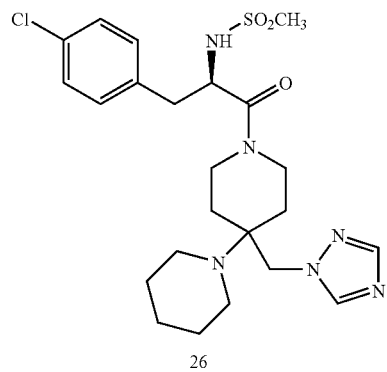

Reagents and conditions: (d) sodium [1,2,4]triazole, DMF; 55° C., 18 hr.

EXAMPLE 2

N-[1-(R)-(4-Chlorobenzyl)-2-oxo-2-(4'-[1,2,4]triazole-1-ylmethyl-[1,4']bipiperidinyl-1'-yl)-ethyl]-methanesulfonamide (26)

Preparation of [1,4']bipiperidinyl-4'-ylmethanol (22): In a three neck round-bottom flask equipped with a stirring bar, reflux condenser, and rubber septa is placed [1,4']bipiperidinyl-4'-carboxylic acid amide (5.01 g, 23.7 mmol) in 140 mL of anhydrous 1-propanol and the solution is heated to reflux. Sodium metal (~9.276 g, 403.4 mmol) rinsed in hexane to remove mineral oil) is added in portions. Once the sodium metal completely dissolves, the mixture is allowed to stir over the weekend. The reaction mixture is cooled to room temperature and the solvent removed under reduced pressure. Distilled water is added and the solution extracted with chloroform. The organic layer is collected, dried over sodium sulfate, filtered, and the solvent removed under reduced pressure to afford 4.4 g of the desired product which is used without further purification. $^1$H NMR (CD$_3$OD, 300 MHz) δ 1.48–1.60 (m, 8H), 1.72–1.80 (m, 2H), 2.61–2.71 (m, 6H), 2.92–3.01 (m, 2H), 3.37 (s, 1H), 3.56 (s, 2H). MS (ESI) m/z 199 (M+H$^+$).

Preparation of [1-(R)-(4-chlorobenzyl)-2-(4'-hydroxymethyl-[1,4']-bipiperidinyl-1'-yl)-2-oxo-ethyl]-carbamic acid tert-butyl ester (23): To a round bottom flask equipped with a stirring bar is charged [1,4']bipiperidinyl-4'-yl-methanol, 22, (2.2 g, 11.1 mmol, 1.0 eq.) 2-(R)-tert-butoxycarbonylamino-3-(4-chlorophenyl)-propionic acid (3.648 g, 12.2 mmol), 1-hydroxybenzotriazole (2.552 g, 18.9 mmol), 1-(3-dimethylaminopropyl)-3-ethylcarbodiimide (3.71 g, 18.9 mmol) in anhydrous N,N-dimethylformamide (80 mL). The mixture is cooled to 0° C. and N,N-diisopropyl-ethylamine (4.1 mL, 37.7 mmol) is added. The ice bath is removed and the reaction mixture allowed to stir overnight. The mixture is concentrated under reduced pressure and purified by preparative HPLC to afford 2.83 g (43% yield) of the desired compound as the trifluoroacetic acid salt. $^1$H NMR (CD$_3$OD, 300 MHz) δ 0.85–2.13 (m, 19H), 2.65–3.82 (m, 8H), 3.90–4.10 (m, 3H), 4.48 (m, 1H), 4.76 (m, 1H), 7.22–7.48 (m, 4H). MS (ESI) m/z 480 (M+H$^+$).

Preparation of 3-[3-(4-Chloro-phenyl)-2-R-methanesulfonylamino-propionyl]-3-aza-7-azonia-dispiro[5.0.5.1]tridecane chloride (25): To a cooled (0° C.) solution of [1-(R)-(4-chloro-benzyl)-2-(4'-hydroxymethyl-[1,4']bipiperidinyl-1'-yl)-2-oxo-ethyl]-carbamic acid tert-butyl ester, 23, (500 mg, 0.84 mmol, 1.0 eq.) in dichloromethane (15 mL) is added triethylamine (0.24 mL, 1.7 mmol) and methanesulfonyl chloride (0.13 mL, 1.7 mmol). The ice bath is removed and the solution allowed to warm to room temperature and continue stirring overnight. The next morning water is added and the reaction mixture extracted with dichloromethane. The organic layer is collected, dried over sodium sulfate, filtered and the solvent was removed under reduced pressure. The resulting crude product is a mixture of the desired product and 3-[2-(R)-tert-butoxy-carbonylamino-3-(4-chloro-phenyl)-propionyl]-3-aza-7-azonia-dispiro[5.0.5.1]tridecane chloride, 24. The crude products are separated by preparative HPLC to afford 121.6 mg (30% yield) of the desired product and 231.9 mg (56% yield) of the major by product, 24. Desired product: $^1$H NMR (CD$_3$OD, 300 MHz) δ 1.48–2.18 (m, 10H), 2.72–3.63 (m, 13H), 3.97 (m, 1H), 4.48 (m, 1H), 4.70 (m, 1H), 7.28–7.42 (m, 4H). MS (ESI) m/z 475 (M+H$^+$). By-product, 24: $^1$H NMR (CD$_3$OD, 300 MHz) δ 1.32–2.15 (m, 19H), 2.86–3.72 (m, 10H), 3.95 (m, 1H), 4.78 (m, 1H), 4.78 (m, 1H), 7.23–7.48 (m, 4H). MS (ESI) m/z 498 (M+H$^+$).

Preparation of N-[1-(R)-(4-chloro-benzyl)-2-oxo-2-(4'-[1,2,4]triazol-1-ylmethyl-[1,4']bipiperidinyl-1'-yl)-ethyl]-methanesulfonamide (26): To a solution of 3-[3-(4-chlorophenyl)-2-R-methanesulfonylamino-propionyl]-3-aza-7-azonia-dispiro[5.0.5.1]tridecane chloride, 25, (121.6 mg, 0.26 mmol) in anhydrous N,N-dimethylformamide (15 mL) is added 1,2,4-triazole, sodium derivative (91.0 mg, 1.0 mmol). The solution is heated to 55° C. and allowed to stir overnight. The next morning the solution is cooled to room temperature, the solvent removed under reduced pressure and the crude material purified by preparative HPLC to afford 81.9 mg (43% yield) of the desired compound as the bis-trifluoroacetic acid salt. $^{1}$H NMR (CD$_{3}$OD, 300 MHz) δ 1.17–2.35 (m, 10H), 2.79–4.00 (m, 1H), 4.20 (m, 1H), 4.47–4.74 (m, 2H), 5.00 (m, 2H), 7.25–7.46 (m, 4H), 8.19 (s, 1H), 8.68 (m, 1H). MS (ESI) m/z 509 (M+H$^{+}$). $^{13}$C NMR (CD$_{3}$OD, 300 MHz) δ 15.50, 22.88, 25.16, 25.34, 29.10, 29.82, 38.64, 39.18, 39.68, 41.55, 41.63, 42.19, 42.53, 54.39, 54,60, 66.89, 68,54, 129.69, 129.88, 132.37, 132.69, 132.80, 133.97, 134.09, 136.58, 136.75, 147.44, 153.07, 153.53, 153.66, 162.35, 162.60, 171.95.

Other units which are suitable for W$^{1}$ under aspect 2 of Category II analogs include: phenyl, pyridin-4-yl, piperidin-4-yl, morpholin-4-yl, pyrazin-1-yl, pyran-4-yl, and the like.

The third aspect of Category I melanocortin receptor ligands according to the present invention comprises the 4-cyclohexylpiperidines having the general scaffold with the formula:

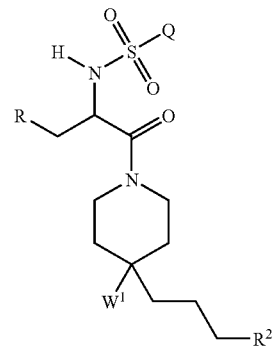

wherein W$^{1}$ comprises a heterocyclic ring, R, R$^{2}$, and Q are defined herein below in Table III.

TABLE III

| No. | R | R$^{2}$ | W$^{1}$ | Q |
|---|---|---|---|---|
| 121 | 4-chlorophenyl | [1,2,4]triazol-1-yl | cyclohexyl | methyl |
| 122 | 4-chlorophenyl | [1,2,4]triazol-1-yl | cyclohexyl | ethyl |
| 123 | 4-chlorophenyl | [1,2,4]triazol-1-yl | cyclohexyl | propyl |
| 124 | 4-chlorophenyl | [1,2,4]triazol-1-yl | cyclohexyl | iso-propyl |
| 125 | 4-chlorophenyl | [1,2,4]triazol-1-yl | cyclohexyl | butyl |
| 126 | 4-chlorophenyl | [1,2,4]triazol-1-yl | cyclohexyl | iso-butyl |
| 127 | 4-chlorophenyl | [1,2,4]triazol-1-yl | cyclohexyl | tert-butyl |
| 128 | 4-chlorophenyl | [1,2,4]triazol-1-yl | cyclohexyl | trifluoromethyl |
| 129 | 4-chlorophenyl | [1,2,4]triazol-1-yl | cyclohexyl | phenyl |
| 130 | 4-chlorophenyl | [1,2,4]triazol-1-yl | cyclohexyl | 4-methylphenyl |
| 131 | 4-chlorophenyl | 2H-tetrazol-5-yl | cyclohexyl | methyl |
| 132 | 4-chlorophenyl | 2H-tetrazol-5-yl | cyclohexyl | ethyl |
| 133 | 4-chlorophenyl | 2H-tetrazol-5-yl | cyclohexyl | propyl |
| 134 | 4-chlorophenyl | 2H-tetrazol-5-yl | cyclohexyl | iso-propyl |
| 135 | 4-chlorophenyl | 2H-tetrazol-5-yl | cyclohexyl | butyl |
| 136 | 4-chlorophenyl | 2H-tetrazol-5-yl | cyclohexyl | iso-butyl |
| 137 | 4-chlorophenyl | 2H-tetrazol-5-yl | cyclohexyl | tert-butyl |
| 138 | 4-chlorophenyl | 2H-tetrazol-5-yl | cyclohexyl | trifluoromethyl |
| 139 | 4-chlorophenyl | 2H-tetrazol-5-yl | cyclohexyl | phenyl |
| 140 | 4-chlorophenyl | 2H-tetrazol-5-yl | cyclohexyl | 4-methylphenyl |
| 141 | 4-chlorophenyl | —NHC(=NH)NH$_{2}$ | cyclohexyl | methyl |
| 142 | 4-chlorophenyl | —NHC(=NH)NH$_{2}$ | cyclohexyl | ethyl |
| 143 | 4-chlorophenyl | —NHC(=NH)NH$_{2}$ | cyclohexyl | propyl |
| 144 | 4-chlorophenyl | —NHC(=NH)NH$_{2}$ | cyclohexyl | iso-propyl |
| 145 | 4-chlorophenyl | —NHC(=NH)NH$_{2}$ | cyclohexyl | butyl |
| 146 | 4-chlorophenyl | —NHC(=NH)NH$_{2}$ | cyclohexyl | iso-butyl |
| 147 | 4-chlorophenyl | —NHC(=NH)NH$_{2}$ | cyclohexyl | tert-butyl |
| 148 | 4-chlorophenyl | —NHC(=NH)NH$_{2}$ | cyclohexyl | trifluoromethyl |
| 149 | 4-chlorophenyl | —NHC(=NH)NH$_{2}$ | cyclohexyl | phenyl |
| 150 | 4-chlorophenyl | —NHC(=NH)NH$_{2}$ | cyclohexyl | naphthanen-2-yl |
| 151 | 4-chlorophenyl | —NHC(O)NH$_{2}$ | cyclohexyl | methyl |
| 152 | 4-chlorophenyl | —NHC(O)NH$_{2}$ | cyclohexyl | ethyl |
| 153 | 4-chlorophenyl | —NHC(O)NH$_{2}$ | cyclohexyl | propyl |
| 154 | 4-chlorophenyl | —NHC(O)NH$_{2}$ | cyclohexyl | iso-propyl |
| 155 | 4-chlorophenyl | —NHC(O)NH$_{2}$ | cyclohexyl | butyl |
| 156 | 4-chlorophenyl | —NHC(O)NH$_{2}$ | cyclohexyl | iso-butyl |
| 157 | 4-chlorophenyl | —NHC(O)NH$_{2}$ | cyclohexyl | tert-butyl |
| 158 | 4-chlorophenyl | —NHC(O)NH$_{2}$ | cyclohexyl | trifluoromethyl |
| 159 | 4-chlorophenyl | —NHC(O)NH$_{2}$ | cyclohexyl | phenyl |
| 160 | 4-chlorophenyl | —NHC(O)NH$_{2}$ | cyclohexyl | naphthanen-2-yl |
| 161 | 4-chlorophenyl | —NHC(=NCH$_{3}$)NH$_{2}$ | cyclohexyl | methyl |

TABLE III-continued

| No. | R | R² | W¹ | Q |
|---|---|---|---|---|
| 162 | 4-chlorophenyl | —NHC(=NCH₃)NH₂ | cyclohexyl | ethyl |
| 163 | 4-chlorophenyl | —NHC(=NCH₃)NH₂ | cyclohexyl | propyl |
| 164 | 4-chlorophenyl | —NHC(=NCH₃)NH₂ | cyclohexyl | iso-propyl |
| 165 | 4-chlorophenyl | —NHC(=NCH₃)NH₂ | cyclohexyl | butyl |
| 166 | 4-chlorophenyl | —NHC(=NCH₃)NH₂ | cyclohexyl | iso-butyl |
| 167 | 4-chlorophenyl | —NHC(=NCH₃)NH₂ | cyclohexyl | tert-butyl |
| 168 | 4-chlorophenyl | —NHC(=NCH₃)NH₂ | cyclohexyl | trifluoromethyl |
| 169 | 4-chlorophenyl | —NHC(=NCH₃)NH₂ | cyclohexyl | phenyl |
| 170 | 4-chlorophenyl | —NHC(=NCH₃)NH₂ | cyclohexyl | naphthanen-2-yl |
| 171 | 4-chlorophenyl | —NHC(=NCN)NHNO₂ | cyclohexyl | methyl |
| 172 | 4-chlorophenyl | —NHC(=NCN)NHNO₂ | cyclohexyl | ethyl |
| 173 | 4-chlorophenyl | —NHC(=NCN)NHNO₂ | cyclohexyl | propyl |
| 174 | 4-chlorophenyl | —NHC(=NCN)NHNO₂ | cyclohexyl | iso-propyl |
| 175 | 4-chlorophenyl | —NHC(=NCN)NHNO₂ | cyclohexyl | butyl |
| 176 | 4-chlorophenyl | —NHC(=NCN)NHNO₂ | cyclohexyl | iso-butyl |
| 177 | 4-chlorophenyl | —NHC(=NCN)NHNO₂ | cyclohexyl | tert-butyl |
| 178 | 4-chlorophenyl | —NHC(=NCN)NHNO₂ | cyclohexyl | trifluoromethyl |
| 179 | 4-chlorophenyl | —NHC(=NCN)NHNO₂ | cyclohexyl | phenyl |
| 180 | 4-chlorophenyl | —NHC(=NCN)NHNO₂ | cyclohexyl | naphthanen-2-yl |

The following is a scheme for preparing melanocortin receptor ligands of the third aspect of Category I. For illustrative purposes only, and not by way of limitation, this example utilizes R equal to 4-chlorophenyl, R² equal to guanidinyl, W¹ equal to cyclohexyl, and Q equal to methyl. The procedure herein below begins with intermediate, 17.

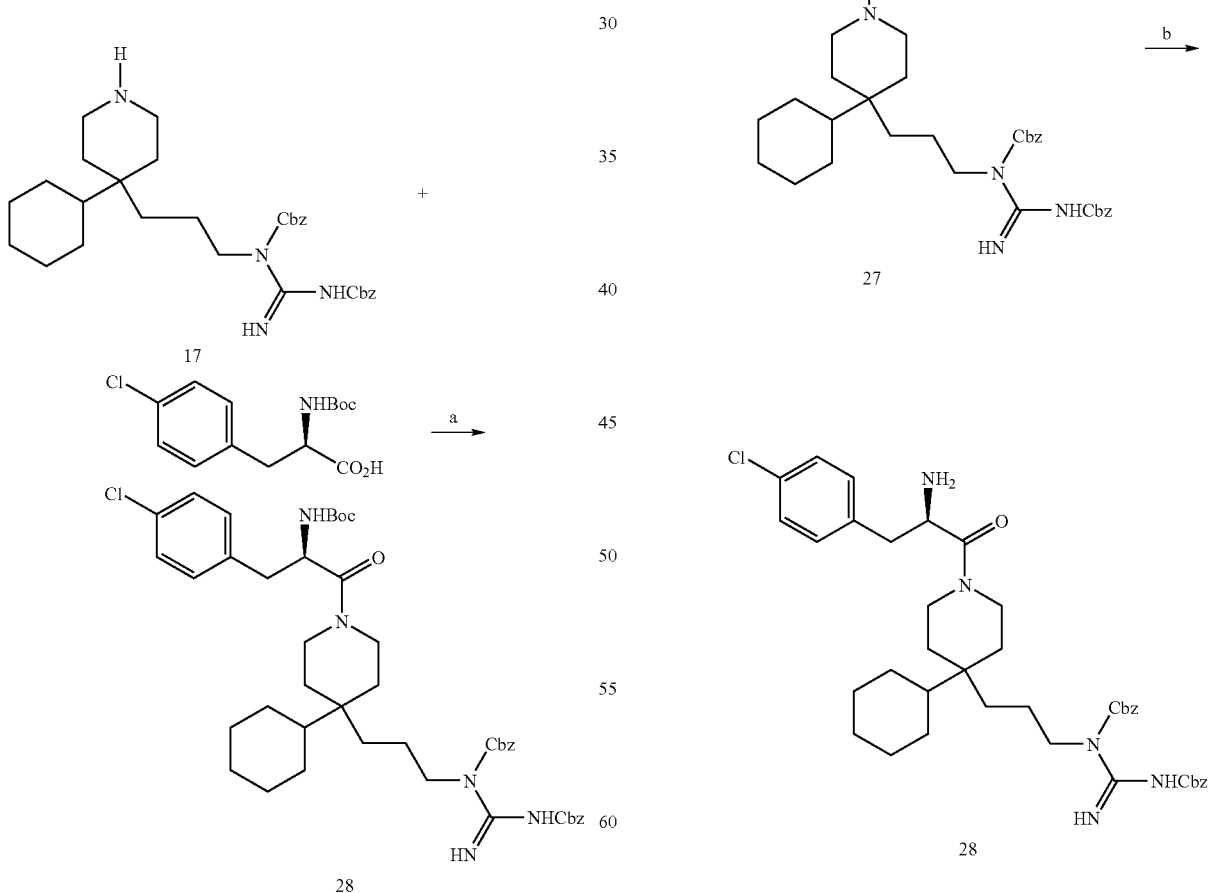

Reagents and conditions (a) HOBt, NMM, EDCI, DMF; rt 6 hr.

Reagents and conditions (b) TFA/CH₂Cl₂/H₂O; rt 1 hr.

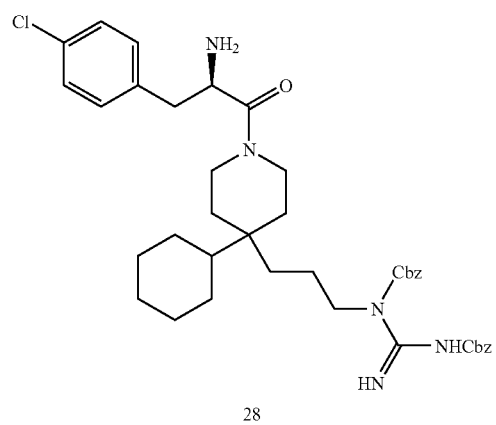

28

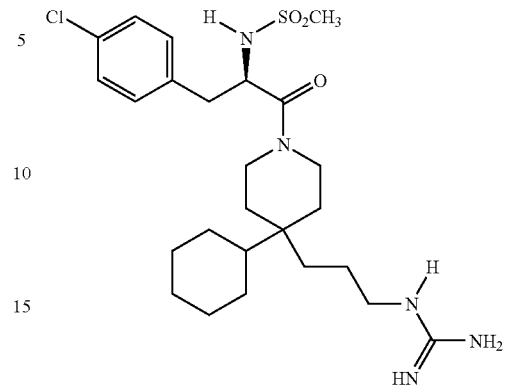

30

Reagents and conditions (d) H₂, 10% Pd/C, MeOH; rt, 6 hr.

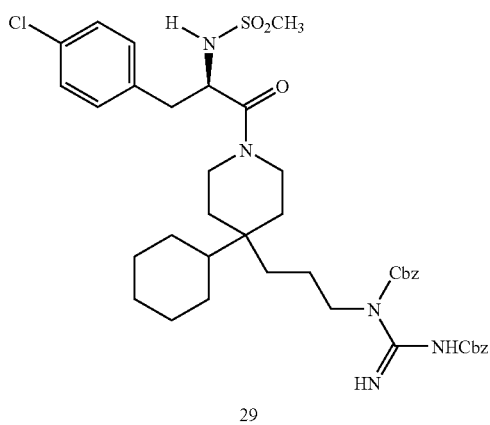

29

Reagents and conditions (c) CH₃SO₂Cl, TEA, THF; 0° C. to rt, 6 hr.

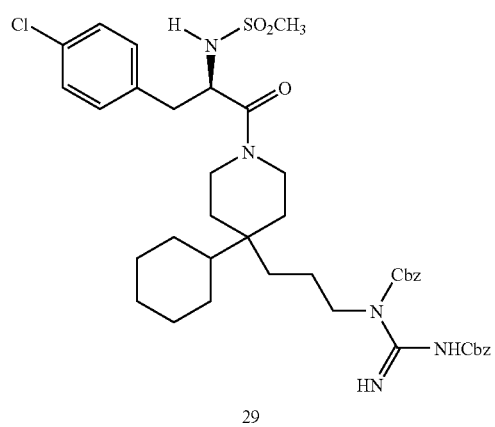

29

EXAMPLE 3

N-[1-(R)-(4-Chlorobenzyl)-2-(4-cyclohexyl-4-guanidinylpropyl-piperidin-1-yl)-2-oxo-ethyl]-methanesulfonamide (30)

Preparation of {1-(R)-(4-chlorobenzyl)-2-[4-cyclohexyl-4-(4-N',N"-dicarbobenzyloxypropyl)-piperidin-1-yl]-2-oxo-ethyl} carbamic acid tert-butyl ester (27): To a solution of N-[3-(4-cyclohexyl-piperidin-4-yl)-propyl]-dicarbobenzyloxy-guanidine, 17, (4.67 g, 8.74 mmol), (R)-2-N-(tert-butoxy-carbonyl)-amino-3-(4-chloro)phenyl-propanoic acid [Boc-D-Ph(p-Cl)—OH] (2.65 g, 9.18 mmol), 1-hydroxy-benzotriazole (2.36 g, 17.5 mmol), N-methylmorpholine (35.0 mmol, 3.83 mL) in DMF (30 mL) is added in portions 1-(3-dimethylaminopropyl)-3-ethylcarbodiimide hydrochloride (2.16 g, 11.4 mmol). The reaction is allowed to stir for 6 hours after which it is quenched by adding aqueous NH₄Cl. The reaction mixture is extracted with EtOAc and the combined layers are dried, concentrated in vacuo, and the resulting crude product purified over silica gel to afford the desired product.

Preparation of 2-(R)-amino-3-(4-chlorophenyl)-1-[4-cyclohexyl-4-(N',N"-dicarbobenzyloxygunnidinylpropyl)-piperidin-1-yl]-propan-1-one (28): A solution of trifluoroacetic acid/dichloromethane/water (1:1:0.1, 5 mL) is added to {1-(R)-(4-chloro-benzyl)-2-[4-cyclohexyl-4-(4-N',N"-dicarbobenzyloxyguanidinylpropyl)-piperidin-1-yl]-2-oxo-ethyl} carbamic acid tert-butyl ester, 27, (5.43 g, 6.65 mmol) and the reaction mixture is allowed to stir for 30 to 60 minutes. The reaction solution is then concentrated in vacuo and partitioned between aqueous NaHCO₃ and EtOAc. The organic phase is concentrated in vacuo and the crude product purified via HPLC over silica gel to afford the desired product.

Preparation of N-{1-(R)-(4-chlorobenzyl)-2-[4-cyclohexyl-4-(N',N"-dicarbobenzyloxyguanidinylpropyl]-piperidin-1-yl)-2-oxo-ethyl}-methane-sulfonamide (29): To a solution of 2-(R)-amino-3-(4-chlorophenyl)-1-(4-cyclohexyl-4-[1,2,4]triazol-1-ylmethyl-piperidin-1-yl)-propan-1-one, 28, (666 mg, 0.93 mmol) in tetrahydrofuran (10 mL) at 0° C. is added triethylamine (0.78 mL, 5.58 mmol) and methanesulfonyl chloride (0.09 mL, 1.11 mmol). The resulting suspension is allowed to stir at room temperature overnight and the solvent removed under reduced pressure. The crude product is purified by preparative HPLC to afford the desired compound.

Preparation of N-[1-(R)-(4-Chlorobenzyl)-2-(4-cyclohexyl-4-guanidinylpropyl-piperidin-1-yl)-2-oxo-ethyl]-methanesulfonamide(30): To a solution of N-{1-(R)-(4-chlorobenzyl)-2-[4-cyclohexyl -4-(N',N''-dicarbobenzyloxyguanidinylpropyl]-piperidin-1-yl)-2-oxo-ethyl}-methane-sulfonamide, 29, (100 mg) in methanol (3 mL) is added 10% palladium on carbon (12 mg) under argon. The mixture is purged with a hydrogen flow and then stirred for two hours under a hydrogen atmosphere at atmospheric pressure. The reaction mixture is then filtered through a short pad of Celite, and the filtrate concentrated under reduced pressure. The crude product is purified by preparative HPLC to afford desired compound as the trifluoroacetic acid salt.

The following precursors can be used to prepare the melanocortin receptor ligands which comprise Category II of the present invention. These precursors can be combined with the precursors which are utilized in preparing the 4,4-disubstituted piperidine scaffolds which comprise Category I described herein above.

A first precursor useful in preparing melanocortin receptor ligands relates to the 3-(4-chlorophenyl)propionic acid derivatives available via the scheme outlined below.

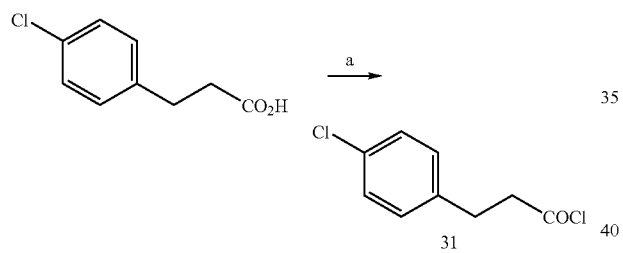

Reagents and conditions: (a) SOCl$_2$, benzene; reflux, 24 hr.

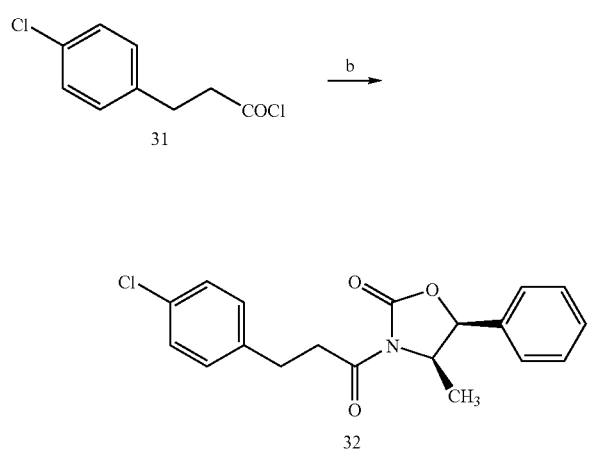

Reagents and conditions: (b) 4-methyl-5-phenyl-oxazolidin-2-one, n-BuLi, THF; -78° C. to rt, 2 hr.

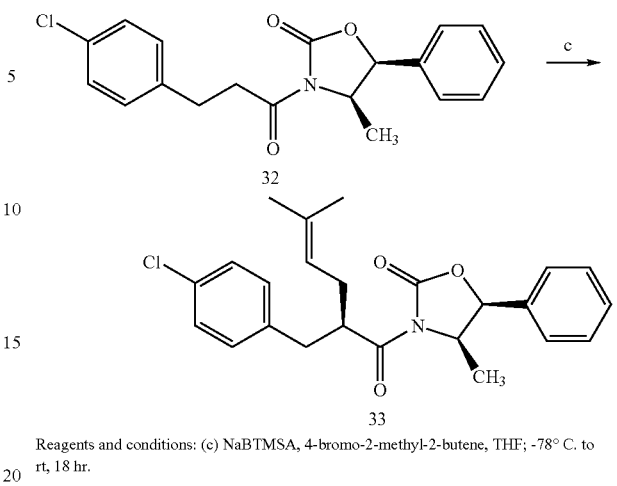

Reagents and conditions: (c) NaBTMSA, 4-bromo-2-methyl-2-butene, THF; -78° C. to rt, 18 hr.

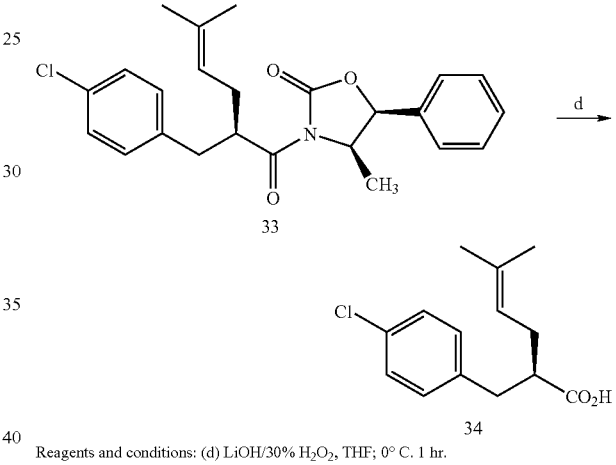

Reagents and conditions: (d) LiOH/30% H$_2$O$_2$, THF; 0° C. 1 hr.

Preparation of 3-(4-chlorophenyl) propionyl chloride (31): To a solution of 3-(4-chloro-phenyl)-propionic acid (1.5 g, 8.15 mmol) in benzene (50 mL) is added thionyl chloride (1.18 mL, 16.3 mmol). The resulting solution is heated to reflux for twenty-four hours and then cooled to room temperature. The solvents are removed under reduced pressure to afford 1.45 g (88% yield) of the desired compound as a colorless oil. The crude product is used without further purification. $^1$H NMR (CDCl$_3$, 300 MHz) δ 3.01 (t, J=7.2 Hz, 2H), 3.22 (t, J=6.9 Hz, 2H), 7.12–7.20 (m, 2H), 7.26–7.35 (m, 2H).

Preparation of 3-[3-(4-chloro-phenyl)-propionyl]-4-(R)-methyl-5-(S)-phenyl-oxazolidin-2-one (32): To a cooled (-78° C.) solution of 4-(R)-methyl-5-(S)-phenyl-oxazolidin-2-one, 31, (600 mg, 3.39 mmol) in anhydrous tetrahydrofuran (20 mL) is added n-butyl lithium (2.5 mL, 1.6M solution in hexanes, 4.07 mmol). The resulting solution is stirred at -78° C. for ninety minutes and then 3-(4-chlorophenyl)-propionyl chloride (894 mg, 4.41 mmol) is slowly added. The solution is warmed to room temperature for thirty minutes and then the solvents removed under reduced pressure. The crude product is purified over silica (20:80 ethyl acetate:hexanes, R$_f$~0.3) to afford 1.07 g (92% yield) of the desired compound as a colorless solid. $^1$H NMR (CDCl$_3$ 300 MHz) δ 0.91 (d, J=6.6 Hz, 3H), 3.01 (t, J=7.8 Hz, 2H), 3.18–3.40 (m, 2H), 4.77 (m, 1H), 5.67 (d, J=7.2 Hz, 1H), 7.18–7.48 (m, 9H). MS (ESI) m/z 344 (M+H$^+$)

Preparation of 3-[2-(S)-(4-chloro-benzyl)-5-methyl-hex-4-enoyl]-4-(R)-methy-5-(S)-phenyl-oxazolidin-2-one (33): To a cooled (−78° C.) solution of 3-[3-(4-chloro-phenyl)-propionyl]-4-(R)-methyl-5-(S)-phenyl-oxazolidin-2-one, 32, (500 mg, 1.46 mmol) in THF (15 mL) is added sodium bis(trimethylsilyl)-amide (1.75 mL, 1.0M solution in THF, 1.75 mmol). The resulting solution is stirred at −78° C. then 4-bromo-2-methyl-2-butene (0.20 mL, 1.75 mmol) is slowly added. The resulting solution is stirred at room temperature overnight, and the solvent removed under reduced pressure. The crude product is purified by preparative HPLC to afford 213 mg (36% yield) of the desired compound as a colorless oil. $^1$H NMR (CDCl$_3$ 300 MHz) δ 0.83 (d, J=6.6 Hz, 3H), 1.62 (s, 3H), 1.70 (s, 3H), 2.20–2.55 (m, 2H), 2.77–3.10 (m, 2H), 4.20–4.35 (m, 1H), 4.55–4.68 (m, 1H), 5.15–5.25 (m, 1H), 5.38 (d, J=7.2 Hz, 1H), 7.15–7.45 (m, 9H). MS (ESI) m/z 412 (M+H$^+$)

Preparation of (S)-2-(4-Chloro-benzyl)-5-methyl-hex-4-enoic acid (34): To a cooled solution of 3-[2-S-(4-chloro-benzyl)-5-methyl-hex-4-enoyl]-4-R-methy-5-S-phenyl-oxazolidin-2-one, 33, (1 mmol) in THF (5 mL) is added a mixture of LiOH/30% H$_2$O$_2$ (1.5 mmol of each) at 0° C. The reaction is stirred for 1 hr, then queched with 1N HCl (pH~2). The solvent is removed, and the product purified over silica to provide the desired product as a white solid.

Using the above procedures and modifications thereof, the following precursors 35–40 can also be suitably prepared.

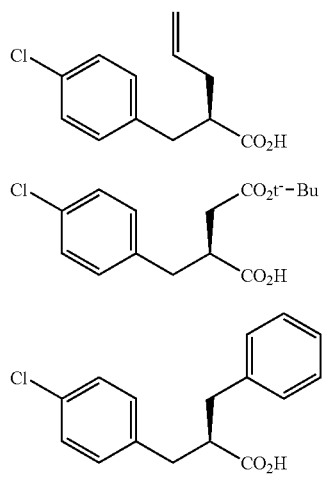

35

36

37

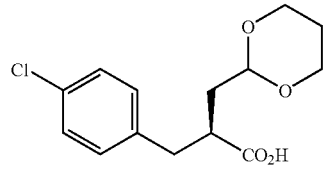

38

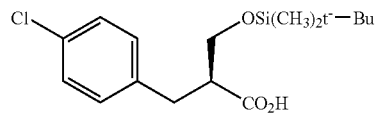

39

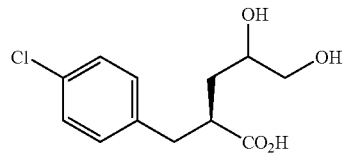

40

The first aspect of Category II melanocortin receptor ligands according to the present invention comprises the 4-cyclohexylpiperidines having the general scaffold with the formula:

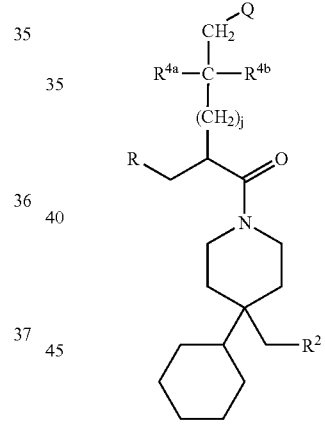

wherein R, R$^2$, R$^{4a}$, R$^{4b}$, Q, and the index j are defined herein below in Table IV.

TABLE IV

| No. | R | R$^2$ | R$^{4a}$ | R$^{4b}$ | j | Q |
|---|---|---|---|---|---|---|
| 181 | 4-fluorophenyl | [1,2,4]triazol-1-yl | H | H | 1 | phenyl |
| 182 | 4-fluorophenyl | [1,2,4]triazol-1-yl | H | —CH$_3$ | 1 | phenyl |
| 183 | 4-fluorophenyl | [1,2,4]triazol-1-yl | H | —NH$_2$ | 1 | phenyl |
| 184 | 4-fluorophenyl | [1,2,4]triazol-1-yl | H | —NHCH$_3$ | 1 | phenyl |
| 185 | 4-fluorophenyl | [1,2,4]triazol-1-yl | H | —NHC(O)CH$_3$ | 1 | phenyl |
| 186 | 4-fluorophenyl | [1,2,4]triazol-1-yl | —CH$_3$ | H | 1 | phenyl |
| 187 | 4-fluorophenyl | [1,2,4]triazol-1-yl | —CH$_3$ | —CH$_3$ | 1 | phenyl |
| 188 | 4-fluorophenyl | [1,2,4]triazol-1-yl | —CH$_3$ | —NH$_2$ | 1 | phenyl |
| 189 | 4-fluorophenyl | [1,2,4]triazol-1-yl | —CH$_3$ | —NHCH$_3$ | 1 | phenyl |
| 190 | 4-fluorophenyl | [1,2,4]triazol-1-yl | —CH$_3$ | —NHC(O)CH$_3$ | 1 | phenyl |
| 191 | 4-fluorophenyl | [1,2,4]triazol-1-yl | H | H | 1 | 4-OH-phenyl |

TABLE IV-continued

| No. | R | $R^2$ | $R^{4a}$ | $R^{4b}$ | j | Q |
|---|---|---|---|---|---|---|
| 192 | 4-fluorophenyl | [1,2,4]triazol-1-yl | H | —CH₃ | 1 | 4-OH-phenyl |
| 193 | 4-fluorophenyl | [1,2,4]triazol-1-yl | H | —NH₂ | 1 | 4-OH-phenyl |
| 194 | 4-fluorophenyl | [1,2,4]triazol-1-yl | H | —NHCH₃ | 1 | 4-OH-phenyl |
| 195 | 4-fluorophenyl | [1,2,4]triazol-1-yl | H | —NHC(O)CH₃ | 1 | 4-OH-phenyl |
| 196 | 4-fluorophenyl | [1,2,4]triazol-1-yl | —CH₃ | H | 1 | 4-OH-phenyl |
| 197 | 4-fluorophenyl | [1,2,4]triazol-1-yl | —CH₃ | —CH₃ | 1 | 4-OH-phenyl |
| 198 | 4-fluorophenyl | [1,2,4]triazol-1-yl | —CH₃ | —NH₂ | 1 | 4-OH-phenyl |
| 199 | 4-fluorophenyl | [1,2,4]triazol-1-yl | —CH₃ | —NHCH₃ | 1 | 4-OH-phenyl |
| 200 | 4-fluorophenyl | [1,2,4]triazol-1-yl | —CH₃ | —NHC(O)CH₃ | 1 | 4-OH-phenyl |
| 201 | 4-chlorophenyl | [1,2,4]triazol-1-yl | H | H | 1 | phenyl |
| 202 | 4-chlorophenyl | [1,2,4]triazol-1-yl | H | —CH₃ | 1 | phenyl |
| 203 | 4-chlorophenyl | [1,2,4]triazol-1-yl | H | —NH₂ | 1 | phenyl |
| 204 | 4-chlorophenyl | [1,2,4]triazol-1-yl | H | —NHCH₃ | 1 | phenyl |
| 205 | 4-chlorophenyl | [1,2,4]triazol-1-yl | H | —NHC(O)CH₃ | 1 | phenyl |
| 206 | 4-chlorophenyl | [1,2,4]triazol-1-yl | —CH₃ | H | 1 | phenyl |
| 207 | 4-chlorophenyl | [1,2,4]triazol-1-yl | —CH₃ | —CH₃ | 1 | phenyl |
| 208 | 4-chlorophenyl | [1,2,4]triazol-1-yl | —CH₃ | —NH₂ | 1 | phenyl |
| 209 | 4-chlorophenyl | [1,2,4]triazol-1-yl | —CH₃ | —NHCH₃ | 1 | phenyl |
| 210 | 4-chlorophenyl | [1,2,4]triazol-1-yl | —CH₃ | —NHC(O)CH₃ | 1 | phenyl |
| 211 | 4-chlorophenyl | [1,2,4]triazol-1-yl | H | H | 1 | 4-OH-phenyl |
| 212 | 4-chlorophenyl | [1,2,4]triazol-1-yl | H | —CH₃ | 1 | 4-OH-phenyl |
| 213 | 4-chlorophenyl | [1,2,4]triazol-1-yl | H | —NH₂ | 1 | 4-OH-phenyl |
| 214 | 4-chlorophenyl | [1,2,4]triazol-1-yl | H | —NHCH₃ | 1 | 4-OH-phenyl |
| 215 | 4-chlorophenyl | [1,2,4]triazol-1-yl | H | —NHC(O)CH₃ | 1 | 4-OH-phenyl |
| 216 | 4-chlorophenyl | [1,2,4]triazol-1-yl | —CH₃ | H | 1 | 4-OH-phenyl |
| 217 | 4-chlorophenyl | [1,2,4]triazol-1-yl | —CH₃ | —CH₃ | 1 | 4-OH-phenyl |
| 218 | 4-chlorophenyl | [1,2,4]triazol-1-yl | —CH₃ | —NH₂ | 1 | 4-OH-phenyl |
| 219 | 4-chlorophenyl | [1,2,4]triazol-1-yl | —CH₃ | —NHCH₃ | 1 | 4-OH-phenyl |
| 220 | 4-chlorophenyl | [1,2,4]triazol-1-yl | —CH₃ | —NHC(O)CH₃ | 1 | 4-OH-phenyl |
| 221 | 4-fluorophenyl | imidazol-1-yl | H | H | 1 | phenyl |
| 222 | 4-fluorophenyl | imidazol-1-yl | H | —CH₃ | 1 | phenyl |
| 223 | 4-fluorophenyl | imidazol-1-yl | H | —NH₂ | 1 | phenyl |
| 224 | 4-fluorophenyl | imidazol-1-yl | H | —NHCH₃ | 1 | phenyl |
| 225 | 4-fluorophenyl | imidazol-1-yl | H | —NHC(O)CH₃ | 1 | phenyl |
| 226 | 4-fluorophenyl | imidazol-1-yl | —CH₃ | H | 1 | phenyl |
| 227 | 4-fluorophenyl | imidazol-1-yl | —CH₃ | —CH₃ | 1 | phenyl |
| 228 | 4-fluorophenyl | imidazol-1-yl | —CH₃ | —NH₂ | 1 | phenyl |
| 229 | 4-fluorophenyl | imidazol-1-yl | —CH₃ | —NHCH₃ | 1 | phenyl |
| 230 | 4-fluorophenyl | imidazol-1-yl | —CH₃ | —NHC(O)CH₃ | 1 | phenyl |
| 231 | 4-fluorophenyl | imidazol-1-yl | H | H | 1 | 4-OH-phenyl |
| 232 | 4-fluorophenyl | imidazol-1-yl | H | —CH₃ | 1 | 4-OH-phenyl |
| 233 | 4-fluorophenyl | imidazol-1-yl | H | —NH₂ | 1 | 4-OH-phenyl |
| 234 | 4-fluorophenyl | imidazol-1-yl | H | —NHCH₃ | 1 | 4-OH-phenyl |
| 235 | 4-fluorophenyl | imidazol-1-yl | H | —NHC(O)CH₃ | 1 | 4-OH-phenyl |
| 236 | 4-fluorophenyl | imidazol-1-yl | —CH₃ | H | 1 | 4-OH-phenyl |
| 237 | 4-fluorophenyl | imidazol-1-yl | —CH₃ | —CH₃ | 1 | 4-OH-phenyl |
| 238 | 4-fluorophenyl | imidazol-1-yl | —CH₃ | —NH₂ | 1 | 4-OH-phenyl |
| 239 | 4-fluorophenyl | imidazol-1-yl | —CH₃ | —NHCH₃ | 1 | 4-OH-phenyl |
| 240 | 4-fluorophenyl | imidazol-1-yl | —CH₃ | —NHC(O)CH₃ | 1 | 4-OH-phenyl |
| 241 | 4-chlorophenyl | imidazol-1-yl | H | H | 1 | phenyl |
| 242 | 4-chlorophenyl | imidazol-1-yl | H | —CH₃ | 1 | phenyl |
| 243 | 4-chlorophenyl | imidazol-1-yl | H | —NH₂ | 1 | phenyl |
| 244 | 4-chlorophenyl | imidazol-1-yl | H | —NHCH₃ | 1 | phenyl |
| 245 | 4-chlorophenyl | imidazol-1-yl | H | —NHC(O)CH₃ | 1 | phenyl |
| 246 | 4-chlorophenyl | imidazol-1-yl | —CH₃ | H | 1 | phenyl |
| 247 | 4-chlorophenyl | imidazol-1-yl | —CH₃ | —CH₃ | 1 | phenyl |
| 248 | 4-chlorophenyl | imidazol-1-yl | —CH₃ | —NH₂ | 1 | phenyl |
| 249 | 4-chlorophenyl | imidazol-1-yl | —CH₃ | —NHCH₃ | 1 | phenyl |
| 250 | 4-chlorophenyl | imidazol-1-yl | —CH₃ | —NHC(O)CH₃ | 1 | phenyl |
| 251 | 4-chlorophenyl | imidazol-1-yl | H | H | 1 | 4-OH-phenyl |
| 252 | 4-chlorophenyl | imidazol-1-yl | H | —CH₃ | 1 | 4-OH-phenyl |
| 253 | 4-chlorophenyl | imidazol-1-yl | H | —NH₂ | 1 | 4-OH-phenyl |
| 254 | 4-chlorophenyl | imidazol-1-yl | H | —NHCH₃ | 1 | 4-OH-phenyl |
| 255 | 4-chlorophenyl | imidazol-1-yl | H | —NHC(O)CH₃ | 1 | 4-OH-phenyl |
| 256 | 4-chlorophenyl | imidazol-1-yl | —CH₃ | H | 1 | 4-OH-phenyl |
| 257 | 4-chlorophenyl | imidazol-1-yl | —CH₃ | —CH₃ | 1 | 4-OH-phenyl |
| 258 | 4-chlorophenyl | imidazol-1-yl | —CH₃ | —NH₂ | 1 | 4-OH-phenyl |
| 259 | 4-chlorophenyl | imidazol-1-yl | —CH₃ | —NHCH₃ | 1 | 4-OH-phenyl |
| 260 | 4-chlorophenyl | imidazol-1-yl | —CH₃ | —NHC(O)CH₃ | 1 | 4-OH-phenyl |

The following is a scheme for preparing melanocortin receptor ligands of the first aspect of Category II. For illustrative purposes only, and not by way of limitation, this example utilizes R equal to 4-fluorophenyl, $R^2$ equal to [1,2,4]triazole-1-yl, $W^1$ equal to cyclohexyl, and Q equal to 4-hydroxyphenyl. The procedure herein below utilizes intermediate 18 for the convergent step wherein the 4,4-substituted piperidine is reacted with the balance of the final compound scaffold.

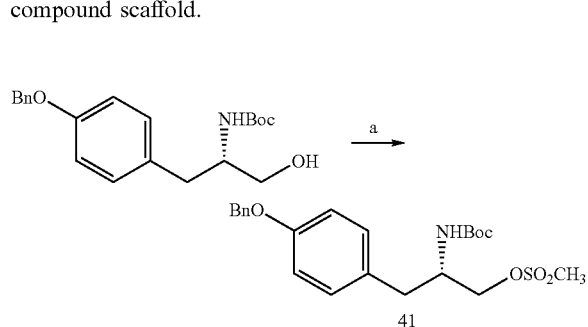

Reagents and conditions: (a) CH₃SO₂Cl, TEA, CH₂Cl₂; 0° C. to rt 3 hr.

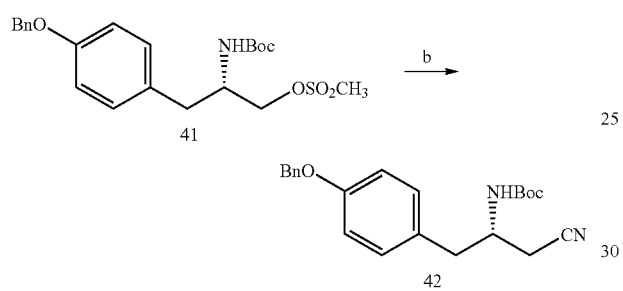

Reagents and conditions: (b) NaCN, DMF, 60° C. 18 hr.

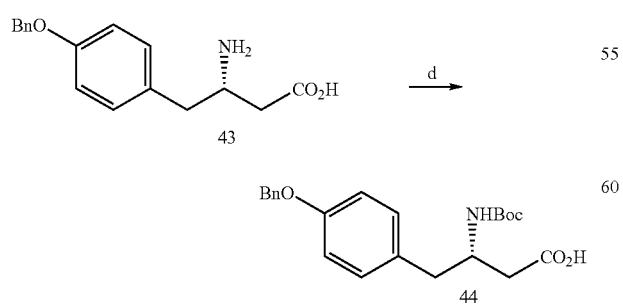

Reagents and conditions: (c) NaOH, MeOH/H₂O; ii) H₂O₂, H₂O; 95° C.

Reagents and conditions: (d) (Boc)₂O, TEA, dioxane/H₂O; 0° C. 18 hr.

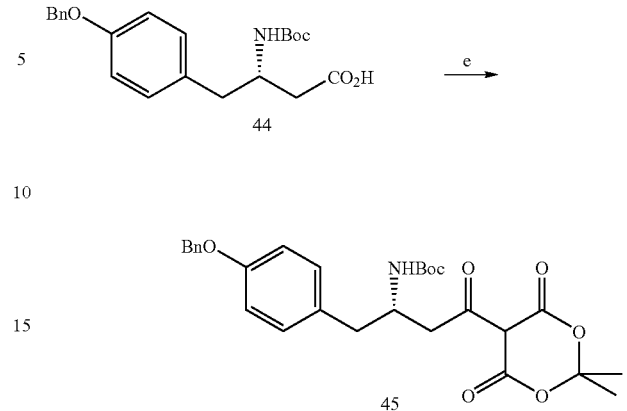

Reagents and conditions: (e) 2,2-dimethyl,-1,3-dioxan-4,6-dione, EDCl, DMAP, CH₂Cl₂; -1° C. to rt 18 hr.

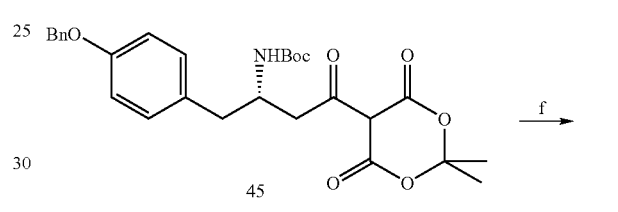

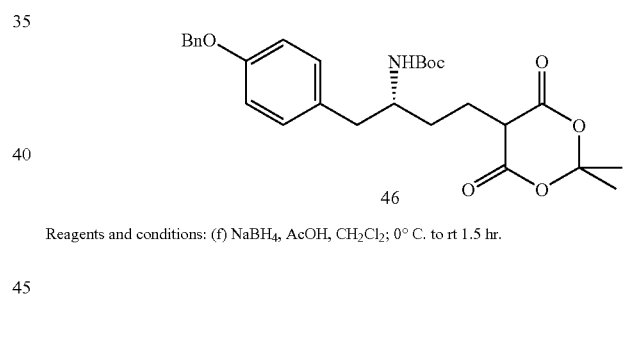

Reagents and conditions: (f) NaBH₄, AcOH, CH₂Cl₂; 0° C. to rt 1.5 hr.

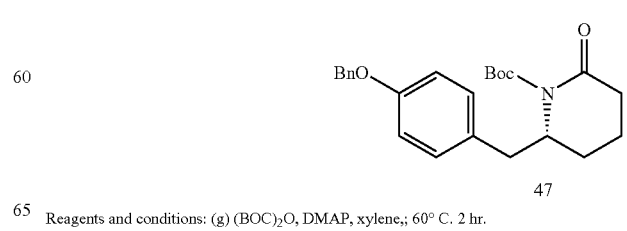

Reagents and conditions: (g) (BOC)₂O, DMAP, xylene,; 60° C. 2 hr.

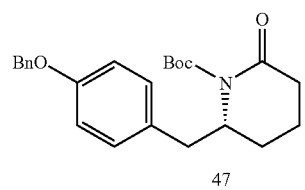
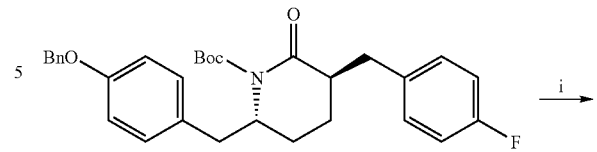
Reagents and conditions: (h) 1) NaBTMSAglyme, THF; ii) 4-fluorobenyl bromide; -70° C. to 0° C. then -70° C. 1 hr.
Reagents and conditions: (i) LiOH H$_2$O$_2$, THF, DMAP, CH$_2$Cl$_2$; -3° C. to rt 18 hr.
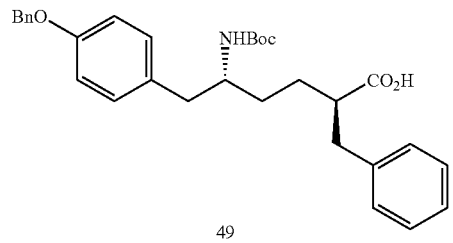
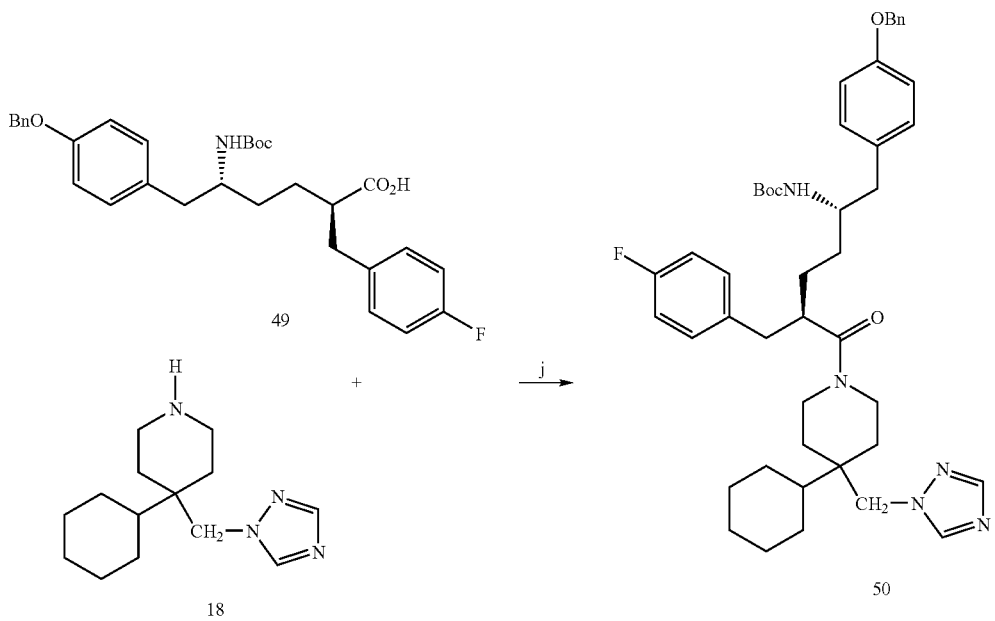
Reagents and conditions: (j) HOBt, NMM, EDCI, DMF, DIPEA; 0° C. to rt, 18 hr

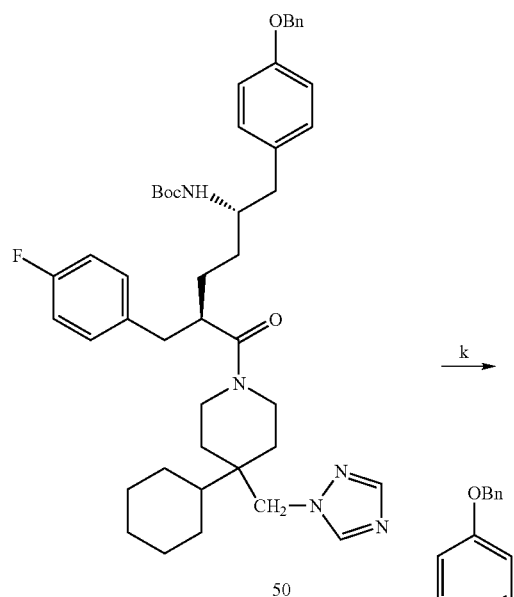
50
Reagents and conditions: (k) TFA/CH$_2$Cl$_2$/H$_2$O rt 1 hr
51
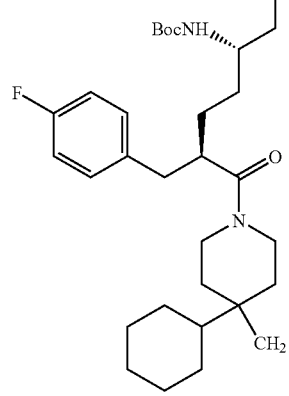
51
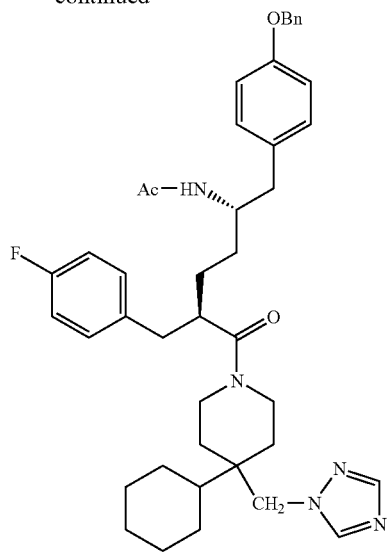
52
Reagents and conditions: (l) Ac$_2$O, MeOH TEA; 0° C. to rt, 1 hr.
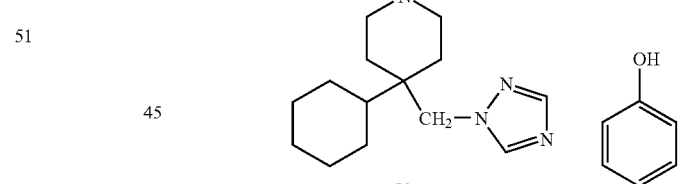
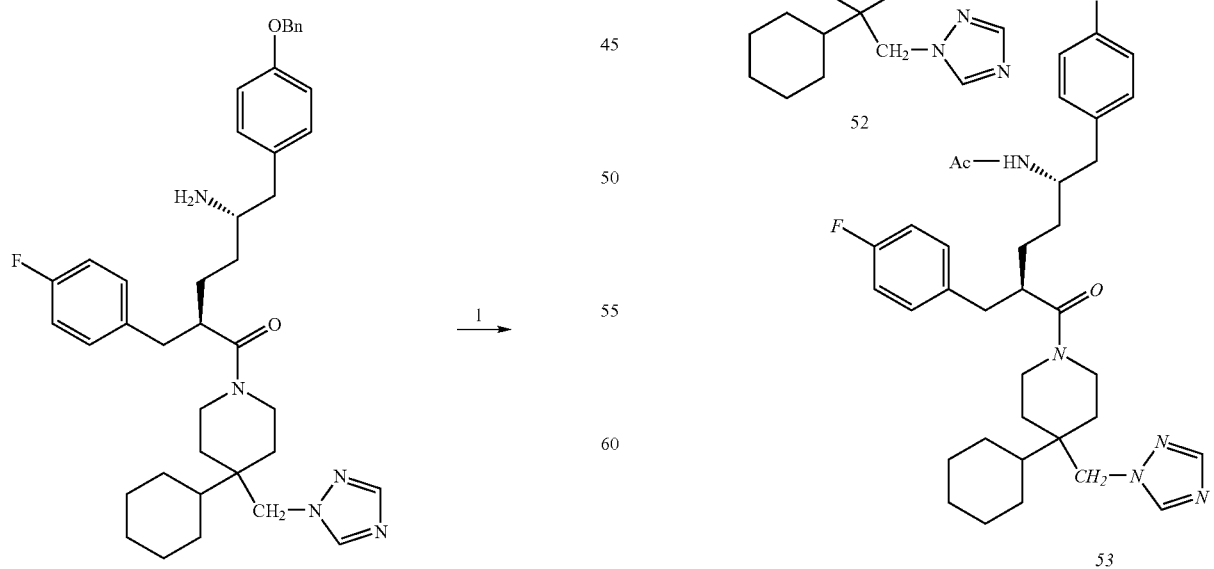
53
Reagents and conditions: (m) H$_2$, Pd/C, EtOH; rt, 2 hr.

EXAMPLE 4

N-[5-(4-cyclohexyl-4-[1,2,4]triazol-1-ylmethyl-piperidin-1-yl)-4-R-(4-fluoro-benzyl)-1-S-(4-hydroxy-benzyl)-5-oxo-pentyl]-acetamide (53)

Preparation of methanesulfonic acid 3-(4-benzyloxy-phenyl)-2-S-tert-butoxycarbonylamino-propyl ester (41): To a cooled (0° C.) solution of [2-(4-benzyloxy-phenyl)-1-S-hydroxymethyl-ethyl]-carbamic acid tert-butyl ester (102.3 g, 286.2 mmol), triethylamine (126 mL, 90.4 mmol) in methylene chloride (2000 mL) is added methanesulfonic anhydride (55.4 g, 31.8 mmol) in three portions over one hour. After the addition is complete, the resulting solution is stirred at 0° C. for thirty minutes and then allowed to warm to room temperature over ninety minutes. The solution is again cooled to 0° C. and quenched with ice-cold 1N aqueous hydrochloric acid (1996 mL) and then stirred vigorously at 0° C. for fifteen minutes. The aqueous layer is removed and extracted with methylene chloride (500 mL). The combined organics are washed with brine (500 mL), dried over anhydrous magnesium sulfate, filtered and concentrated under reduced pressure to provide a thick slurry which is diluted with hexanes (300 mL). The resulting solid that forms is collected by filtration, washed with hexanes (50 mL) and dried to constant weight in vacuo to afford 119.6 g (96% yield) of the desired compound which is used without further purification.

Preparation of [1-(4-benzyloxy-benzyl)-2-cyano-ethyl]-carbamic acid tert-butyl ester (42): To a solution of methanesulfonic acid 3-(4-benzyloxy-phenyl)-2-S-tert-butoxycarbonylamino-propyl ester, 41, (119.5 g, 274.5 mmol), in N,N-dimethylformamide (1020 mL) is added sodium cyanide (30.0 g, 612 mmol). The resulting suspension is heated to 60° C. for eighteen hours and then cooled to room temperature. The reaction is diluted with water (4400 mL) and extracted with ethyl acetate (3×2400 mL). The combined organic extracts are washed successively with water (2×2000 mL) and saturated aqueous sodium chloride (2000 mL). The organics layers are separated, dried over anhydrous magnesium sulfate, filtered and concentrated under reduced pressure. The crude product is purified over silica (2:3 ethyl acetate:hexanes) to afford 75.1 g (77.7% yield) of the desired compound as a solid.

Preparation of 3-S-amino-4-(4-benzyloxy-phenyl)-butyric acid (43): To a suspension of [1-(4-benzyloxy-benzyl)-2-cyano-ethyl]-carbamic acid tert-butyl ester, 42, (52.0 g, 142 mmol) in methanol (1500 mL) is heated to 45° C. and then water (156 mL and 50% aqueous sodium hydroxide (312 mL 5960 mmol) is added. The resulting solution is heated to 75° C. for five hours and then cooled to room temperature. The methanol is removed under reduced pressure and the residue diluted with water (1200 mL) and subsequently heated to 90° C. Hydrogen peroxide (87 mL, 50 wt. % solution in water, 1500 mmol) is then added over forty minutes and the resulting solution heated at 95° C. for an additional eighteen hours. Additional hydrogen peroxide (40 mL 690 mmol) is added and the mixture heated to reflux for five hours followed by cooling to 40° C. The reaction mixture is poured over ice (8000 mL) and then acidified to pH 2.1 with ice-cold 2 M sulfuric acid. The resulting suspension is vigorously stirred for fifteen minutes and the resulting solid collected by filtration. The solid is washed with water (2×500 mL) and dried to constant weight in vacuo. The crude product is used without further purification.

Preparation of 4-(4-benzyloxyphenyl)-3-S-tert-butoxycarbonylamino-butyric acid (44): To a solution of 3-S-amino-4-(4-benzyloxy-phenyl)-butyric acid, 43, (40.47 g, 142 mmol) in 1,4-dioxane (1500 mL) is added triethylamine (108.8 mL, 780.6 mmol) water (1500 mL) and sodium hydrogen carbonate (23.6 g, 281 mmol). The resulting suspension was stirred at room temperature for two hours to give a complete solution. The solution is then cooled to 0° C. and a solution of di-tert-butyl dicarbonate (53.3 g, 244 mmol) in 1,4-dioxane (300 mL) is added dropwise over thirty minutes. After the addition is complete the solution is stirred at 0° C. for one hour and then allowed to warm to room temperature for eighteen hours. The organic solvent is removed under reduced pressure and the aqueous layer partitioned between water (1000 mL) and ethyl acetate (1000 mL). The mixture is cooled to 0° C. and then acidified to pH 2.1 by the slow addition of aqueous 1M potassium hydrogen sulfate (~760 mL). The aqueous layer is removed and extracted with ethyl acetate (2×500 mL). The combined organic layers are washed with saturated aqueous sodium chloride (2×750 mL), dried over anhydrous magnesium sulfate, filtered and concentrated under reduced pressure to a residue which is then triterated with ether (400 mL). The mixture is diluted with hexanes (400 mL) and concentrated under reduced pressure to a thick slurry. The resulting solid is collected by filtration, rinsed with hexanes (2×100 mL) and dried to a constant weight in vacuo to give 49.2 g (90% yield) of the desired compound which is used without further purification.

Preparation of [1-S-(4-benzyloxy-benzyl)-3-(2,2-dimethyl-4,6-dioxo-[1,3]dioxan-5-yl)-3-oxo-propyl]-carbamic acid tert-butyl ester (45): To a cooled (−1° C.) solution of 4-(4-benzyloxyphenyl)-3-S-tert-butoxycarbonylamino-butyric acid, 44, (96.4 g, 251 mmol) in methylene chloride (2500 mL) is added 4-dimethylaminopyridine (45.8 g, 375 mmol), 2,2-dimethyl-1,3-dioxan-4,6-dione (39.9 g, 277 mmol) and 1-[3-(dimethylamino)propyl]-3-ethylcarbodiimide hydrochloride (72.5 g, 378 mmol). The resulting solution is stirred at −1° C. for ninety minutes and then warmed to room temperature overnight. The reaction is diluted with methylene chloride (1000 mL), cooled to 0° C., and washed successively with ice-cold 1M potassium hydrogen sulfate (3×700 mL), water (1000 mL) and saturated aqueous sodium chloride (1000 mL). The organics were dried over anhydrous magnesium sulfate, filtered and concentrated under reduced pressure to a yellow residue. The residue is dissolved in a 1:1 mixture of methylene chloride/ether (300 mL), diluted with hexanes (150 mL), and then concentrated under reduced pressure to a thick slurry. The resulting solid is collected by filtration, rinsed with ethyl ether (100 mL) and dried to constant weight in vacuo to afford 120.0 g (94% yield) of the desired compound which is used without further purification.

Preparation of [1-R-(4-benzyloxy-benzyl)-3-(2,2-dimethyl-4,6-dioxo-[1,3]dioxan-5-yl)-propyl]-carbamic acid tert-butyl ester (46): To a cooled (0° C.) solution of [1-S-(4-benzyloxy-benzyl)-3-(2,2-dimethyl-4,6-dioxo-[1,3]dioxan-5-yl)-3-oxo-propyl]-carbamic acid tert-butyl ester, 45, (120.9 g, 236.3 mmol) in methylene chloride (2300 mL) is added acetic acid (150 mL, 2620 mmol) and sodium borohydride (35.9 g, 949 mmol) in portions over forty-five minutes. After the addition is complete the mixture is stirred at 0° C. for ninety minutes and then allowed to warm to room temperature overnight. The reaction is quenched by the slow addition of water (1000 mL) and then the aqueous layer is removed and extracted with methylene chloride (2×750 mL). The combined organics are washed successively with water (2×1000 mL) and saturated aqueous sodium chloride (3×1000 mL), dried over anhydrous magnesium sulfate filtered, and then concentrated under reduced pressure. The crude product is purified by chromatography on silica gel (methylene chloride-methylene chloride:ethyl acetate, 3:1–2:1). The pure fractions are collected and concentrated under reduced pressure to a residue. The residue is triturated with methylene chloride (400 mL) and then concentrated at 0° C. to a thick slurry. The solid is collected by filtration, washed with 1:1 ethyl ether:hexanes (2×75 mL) and then dried to constant weight in vacuo to give 46.8 g (50% yield of the desired compound.

Preparation of 2-R-(4-benzyloxy-benzyl)-6-oxo-piperidine-1-carboxylic acid tert-butyl ester (47): To a suspension of [1-R-(4-benzyloxy-benzyl)-3-(2,2-dimethyl-4,6-dioxo-[1,3]dioxan-5-yl)-propyl]-carbamic acid tert-butyl ester, 46, (38.5 g, 77.4 mmol) in xylenes (750 mL) was heated to reflux for two hours until the solid was completely in solution and was then cooled to 60° C. Di-tert-butyl dicarbonate (11.5 g, 52.7 mmol) and 4-(dimethyl-amino)pyridine (4.0 g, 33 mmol) were added and the resulting solution was stirred at 60° C. for two hours and then cooled to 3° C. The solution was washed successively with ice-cold 1M potassium hydrogen sulfate (230 mL), water (200 mL), saturated aqueous sodium bicarbonate (200 mL) and saturated aqueous sodium chloride (100 mL). The organics were dried over anhydrous sodoium sulfate, filtered and then concentrated under reduced pressure to a pale yellow residue. The crude product was purified by chromatography on silica gel (methylene chloride:ethyl acetate 4:1–3:1) and the pure fractions were collected and concentrated under reduced pressure. The residue was dissolved in ethyl ether (200 mL) and the resulting solution was diluted with hexanes (100 mL) and then concentrated at 0° C. in vacuo to a thick slurry. The solid was collected by filtration and rinsed with 5% ethyl ether in hexanes (100 mL) and then dried to constant weight in vacuo to give 26.5 g (87% yield) of the desired compound. $^1$H NMR (500 MHz) 1.52 (s, 9H), 1.65–1.80 (m, 3H), 1.90–2.05 (m, 1H), 2.45– 2.58 (m, 2H), 2.60–2.70 (m, 1H), 3.00–3.08 (m, 1H), 4.35–4.40 (m, 1H), 5.05 (s, 2H), 6.93 (d, 2H), 7.13 (d, 2H), 7.28–7.35 (m, 1H), 7.35–7.50 (m, 4H). $^{13}$C NMR (125 MHz) 17.11, 24.69, 28.19, 34.53, 39.14, 57.40, 70.23, 83.06, 115.18, 127.56, 128.07, 128.70, 130.29, 130.40, 137.20, 152.98, 157.80, 171.62. MS (ESI) m/z 418 (M+Na$^+$). Anal Calcd. for $C_{24}H_{29}NO_4$: C, 72.89; H, 7.39; N, 3.54. Found: C, 72.97; H, 7.44; 3.53.

Preparation of 6-R-(4-Benzyloxy-benzyl)-3-R-(4-fluoro-benzyl)-2-oxo-piperidine-1-carboxylic acid tert-butyl ester (48): To a cooled (−70° C.) solution of 2-R-(4-benzyloxy-benzyl)-6-oxo-piperidine-1-carboxylic acid tert-butyl ester, 47, (12.0 g, 30.3 mmol), in THF (240 mL) and ethylene glycol dimethyl ether (240 mL) is added sodium bis(trimethylsilyl)-amide (33 mL, 1M solution in THF, 33 mmol). The resulting solution is warmed to 0° C. for thirty minutes and then cooled to −70° C. and 4-fluorobenzyl bromide (5.2 g, 27.5 mmol) is added. The resulting solution is stirred at −70° C. for forty minutes and then quenched with saturated aqueous ammonium chloride (200 mL). The organic solvents are removed under reduced pressure and the remaining aqueous layer is extracted with ethyl acetate (1000 mL). The organic layer is separated and washed with water (200 mL) and saturated aqueous sodium chloride (200 mL). The organics are dried over anhydrous magnesium sulfate, filtered and concentrated under reduced pressure. The crude product is purified over silica to afford 11.5 g (38%) of the title compound as a colorless solid. $^1$HNMR (CDCl$_3$ 300 MHz) δ 1.35–1.93 (m, 4H), 1.63 (s, 9H), 2.35–3.10 (m, 4H), 3.25–3.35 (m, 1H), 4.25–4.35 (m, 1H), 5.08 (s, 2H), 6.85–7.50 (m, 13H).

Preparation of 2-R-benzyl-6-(4-benzyloxy-phenyl)-5-R-tert-butoxy-carbonylamino-hexanoic acid (49): To a cooled (−3° C.) solution of 6-R-(4-benzyloxy-benzyl)-3-R-(4-fluoro-benzyl)-2-oxo-piperidine-1-carboxylic acid tert-butyl ester, 48, (11.5 g, 22.9 mmol), in THF (150 mL) is slowly added lithium hydroxide monohydrate (3.7 g, 88 mmol) so as to maintain the reaction temperature between −3° C. and +3° C. The resulting reaction mixture is stirred at 0° C. for five minutes and then 30% aqueous hydrogen peroxide solution (12 mL) is added over five minutes. The resulting solution was stirred at room temperature for one hour and then allowed to stir for eighteen hours. The organics solvent was removed under reduced pressure and the remaining residue partitioned between methylene chloride (1000 mL) and water (400 mL). Potassium hydrogen sulfate (200 mL, 1M solution), was then added and the organics separated and washed with 10% aqueous sodium hydrogen sulfate (2×500 mL), water (500 mL) and saturated aqueous sodium chloride (500 mL). The organics are separated, dried over anhydrous magnesium sulfate filtered, and concentrated under reduced pressure to afford 10.8 g (91%) of the title compound as a colorless solid. $^1$H NMR (DMSO 300 MHz) δ 1.10–1.75 (m, 3H), 1.37 (s, 9H), 2.42–2.90 (m, 5H), 3.30–3.70 (m, 2H), 5.08 (s, 2H), 6.68 (d, 1H), 6.90–7.55 (m, 13H). $^{13}$C NMR (DMSO 75 MHz) ppm 28.65, 28.95, 32.51, 37.68, 47.27, 52.12, 69.84, 77.96, 128.29, 128.42, 129.09, 130.73, 131.17, 131.28, 132.13, 136.40, 137.98, 156.04, 157.36, 159.91, 163.12, 176.84. MS (ESI) m/z 522 (M+H$^+$)

Preparation of [1-S-(4-benzyloxy-benzyl)-5-(4-cyclohexyl-4-[1,2,4]triazol-1-ylmethyl-piperidin-1-yl)-4-R-(4-fluoro-benzyl)-5-oxo-pentyl]-carbamic acid tert-butyl ester (50): To a solution of 6-(4-benzyloxy-phenyl)-5-S-tert-butoxycarbonylamino-2-R-(4-fluoro-benzyl)-hexanoic acid, 49, (110 mg, 0.21 mmol), 4-cyclohexyl-4-[1,2,4]triazol-1-ylmethyl-piperidine, 18, (50 mg, 0.20 mmol), 1-hydroxybenzotriazole (54 mg, 0.40 mmol), 4-methylmorpholine (88 □l, 0.80 mmol) in N,N-dimethylformamide (7 mL) is added 1-(3-dimethylaminopropyl)-3-ethylcarbodiimide (50 mg, 0.26 mmol). The reaction mixture is stirred overnight and then aqueous ammonium chloride is added. The reaction is extracted with ethyl acetate, and the organics are separated dried over sodium sulfate, filtered and concentrated under reduced pressure. The crude product is purified by preparative HPLC to afford 111 mg (74% yield) of the desired compound. MS (ESI) m/z 752, (M+H$^+$).

Preparation of 5-S-amino-6-(4-benzyloxy-phenyl)-1-(4-cyclohexyl-4-[1,2,4]triazol-1-ylmethyl-piperidin-1-yl)-2-R-(4-fluoro-benzyl)-hexan-1-one (51): A ready-to-use solution of trifluoroacetic acid:methylene chloride:water (1:1:0.1, 6 mL) is added to [1-S-(4-benzyloxy-benzyl)-5-(4-cyclohexyl-4-[1,2,4]triazol-1-ylmethyl-piperidin-1-yl)-4-R-(4-fluoro-benzyl)-5-oxo-pentyl]-carbamic acid tert-butyl ester (100 mg, 0.13 mmol), and the reaction mixture is stirred for 0.5–1.0 hour. The mixture is concentrated under reduced pressure and then partitioned between ethyl acetate and aqueous sodium bicarbonate. The organic layer is separated and concentrated under reduced pressure. The crude material is used without further purification.

Preparation of N-[1-S-(4-benzyloxy-benzyl)-5-(4-cyclohexyl-4-[1,2,4]triazol-1-ylmethyl-piperidin-1-yl)-4-R-(4-fluoro-benzyl)-5-oxo-pentyl]-acetamide (52): To a chilled (0° C.) solution of the 5-S-amino-6-(4-benzyloxy-phenyl)-1-(4-cyclohexyl-4-[1,2,4]triazol-1-ylmethyl-piperidin-1-yl)-2-R-(4-fluoro-benzyl)-hexan-1-one, 51, and triethylamine (54 μL, 0.39 mmol) in methanol (5 mL) is added acetic anhydride (39 μL, 0.41 mmol) dropwise. The mixture is stirred for one hour at room temperature. The excess triethylamine, acetic anhydride and solvent are removed under reduced pressure. The crude product is used directly in the next step. MS (ESI) m/z 694, (M+H$^+$).

Preparation of N-[5-(4-cyclohexyl-4-[1,2,4]triazol-1-yl-methyl-piperidin-1-yl)-4-R-(4-fluoro-benzyl)-1-S-(4-hydroxy-benzyl)-5-oxo-pentyl]-acetamide (53): To a solution of N-[1-S-(4-benzyloxy-benzyl)-5-(4-cyclohexyl-4-[1,2,4]triazol-1-ylmethyl-piperidin-1-yl)-4-R-(4-fluoro-benzyl)-5-oxo-pentyl]-acetamide, 52, (100 mg) in ethanol (4 mL) was added 10% palladium on carbon (120 mg) under argon. The mixture is purged with a hydrogen and then stirred for two hours under a hydrogen atmosphere at atmospheric pressure. The reaction mixture was then filtered through a short pad of Celite and the filtrate is concentrated under reduced pressure. The crude product is purified by preparative HPLC to give 170 mg of the desired compound as the trifluoroacetic acid salt. MS (ESI) m/z 604, (M+H$^+$).

The second aspect of Category II relates to compounds having the formula:

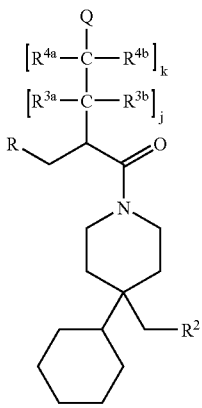

wherein either $R^{3a}$ and $R^{3b}$ or $R^{4a}$ and $R^{4b}$ are taken together to form a carbonyl unit. The following are non-limiting examples which particularly point out examples of compounds comprising the second aspect of Category II analogs.

Compounds wherein $R^{3a}$ and $R^{3b}$ are each hydrogen, j is equal to 1; k is equal to 0 said compounds having the formula:

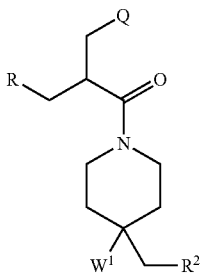

wherein R, $R^2$ and Q are defined herein below in Table V.

TABLE V

| No. | R | $R^2$ | $W^1$ | Q |
|---|---|---|---|---|
| 261 | 4-chlorophenyl | [1,2,4]triazol-1-yl | cyclohexyl | —CO$_2$H |
| 262 | 4-chlorophenyl | [1,2,4]triazol-1-yl | cyclohexyl | —CONH$_2$ |
| 263 | 4-chlorophenyl | [1,2,4]triazol-1-yl | cyclohexyl | —CONHCH$_3$ |
| 264 | 4-chlorophenyl | [1,2,4]triazol-1-yl | cyclohexyl | —CONH(CH$_3$)$_2$ |
| 265 | 4-chlorophenyl | [1,2,4]triazol-1-yl | cyclohexyl | —CONHSO$_2$CH$_3$ |
| 266 | 4-chlorophenyl | 2H-tetrazol-5-yl | cyclohexyl | —CO$_2$H |
| 267 | 4-chlorophenyl | 2H-tetrazol-5-yl | cyclohexyl | —CONH$_2$ |
| 268 | 4-chlorophenyl | 2H-tetrazol-5-yl | cyclohexyl | —CONHCH$_3$ |
| 269 | 4-chlorophenyl | 2H-tetrazol-5-yl | cyclohexyl | —CONH(CH$_3$)$_2$ |
| 270 | 4-chlorophenyl | 2H-tetrazol-5-yl | cyclohexyl | —CONHSO$_2$CH$_3$ |
| 271 | 4-chlorophenyl | imdazol-1-yl | cyclohexyl | —CO$_2$H |
| 272 | 4-chlorophenyl | imdazol-1-yl | cyclohexyl | —CONH$_2$ |
| 273 | 4-chlorophenyl | imdazol-1-yl | cyclohexyl | —CONHCH$_3$ |
| 274 | 4-chlorophenyl | imdazol-1-yl | cyclohexyl | —CONH(CH$_3$)$_2$ |
| 275 | 4-chlorophenyl | imdazol-1-yl | cyclohexyl | —CONHSO$_2$CH$_3$ |
| 276 | 4-fluorophenyl | [1,2,4]triazol-1-yl | cyclohexyl | —CO$_2$H |
| 277 | 4-fluorophenyl | [1,2,4]triazol-1-yl | cyclohexyl | —CONH$_2$ |
| 278 | 4-fluorophenyl | [1,2,4]triazol-1-yl | cyclohexyl | —CONHCH$_3$ |
| 279 | 4-fluorophenyl | [1,2,4]triazol-1-yl | cyclohexyl | —CONH(CH$_3$)$_2$ |
| 280 | 4-fluorophenyl | [1,2,4]triazol-1-yl | cyclohexyl | —CONHSO$_2$CH$_3$ |
| 281 | 4-fluorophenyl | 2H-tetrazol-5-yl | cyclohexyl | —CO$_2$H |
| 282 | 4-fluorophenyl | 2H-tetrazol-5-yl | cyclohexyl | —CONH$_2$ |
| 283 | 4-fluorophenyl | 2H-tetrazol-5-yl | cyclohexyl | —CONHCH$_3$ |
| 284 | 4-fluorophenyl | 2H-tetrazol-5-yl | cyclohexyl | —CONH(CH$_3$)$_2$ |
| 285 | 4-fluorophenyl | 2H-tetrazol-5-yl | cyclohexyl | —CONHSO$_2$CH$_3$ |
| 286 | 4-fluorophenyl | imdazol-1-yl | cyclohexyl | —CO$_2$H |
| 287 | 4-fluorophenyl | imdazol-1-yl | cyclohexyl | —CONH$_2$ |
| 288 | 4-fluorophenyl | imdazol-1-yl | cyclohexyl | —CONHCH$_3$ |
| 289 | 4-fluorophenyl | imdazol-1-yl | cyclohexyl | —CONH(CH$_3$)$_2$ |
| 290 | 4-fluorophenyl | imdazol-1-yl | cyclohexyl | —CONHSO$_2$CH$_3$ |
| 291 | 4-chlorophenyl | [1,2,4]triazol-1-yl | piperidin-4-yl | —CO$_2$H |
| 292 | 4-chlorophenyl | [1,2,4]triazol-1-yl | piperidin-4-yl | —CONH$_2$ |
| 293 | 4-chlorophenyl | [1,2,4]triazol-1-yl | piperidin-4-yl | —CONHCH$_3$ |
| 294 | 4-chlorophenyl | [1,2,4]triazol-1-yl | piperidin-4-yl | —CONH(CH$_3$)$_2$ |
| 295 | 4-chlorophenyl | [1,2,4]triazol-1-yl | piperidin-4-yl | —CONHSO$_2$CH$_3$ |
| 296 | 4-chlorophenyl | 2H-tetrazol-5-yl | piperidin-4-yl | —CO$_2$H |
| 297 | 4-chlorophenyl | 2H-tetrazol-5-yl | piperidin-4-yl | —CONH$_2$ |
| 298 | 4-chlorophenyl | 2H-tetrazol-5-yl | piperidin-4-yl | —CONHCH$_3$ |
| 299 | 4-chlorophenyl | 2H-tetrazol-5-yl | piperidin-4-yl | —CONH(CH$_3$)$_2$ |
| 300 | 4-chlorophenyl | 2H-tetrazol-5-yl | piperidin-4-yl | —CONHSO$_2$CH$_3$ |
| 301 | 4-chlorophenyl | imdazol-1-yl | piperidin-4-yl | —CO$_2$H |
| 302 | 4-chlorophenyl | imdazol-1-yl | piperidin-4-yl | —CONH$_2$ |
| 303 | 4-chlorophenyl | imdazol-1-yl | piperidin-4-yl | —CONHCH$_3$ |
| 304 | 4-chlorophenyl | imdazol-1-yl | piperidin-4-yl | —CONH(CH$_3$)$_2$ |
| 305 | 4-chlorophenyl | imdazol-1-yl | piperidin-4-yl | —CONHSO$_2$CH$_3$ |
| 306 | 4-fluorophenyl | [1,2,4]triazol-1-yl | piperidin-4-yl | —CO$_2$H |
| 307 | 4-fluorophenyl | [1,2,4]triazol-1-yl | piperidin-4-yl | —CONH$_2$ |
| 308 | 4-fluorophenyl | [1,2,4]triazol-1-yl | piperidin-4-yl | —CONHCH$_3$ |
| 309 | 4-fluorophenyl | [1,2,4]triazol-1-yl | piperidin-4-yl | —CONH(CH$_3$)$_2$ |
| 310 | 4-fluorophenyl | [1,2,4]triazol-1-yl | piperidin-4-yl | —CONHSO$_2$CH$_3$ |
| 311 | 4-fluorophenyl | 2H-tetrazol-5-yl | piperidin-4-yl | —CO$_2$H |
| 312 | 4-fluorophenyl | 2H-tetrazol-5-yl | piperidin-4-yl | —CONH$_2$ |
| 313 | 4-fluorophenyl | 2H-tetrazol-5-yl | piperidin-4-yl | —CONHCH$_3$ |
| 314 | 4-fluorophenyl | 2H-tetrazol-5-yl | piperidin-4-yl | —CONH(CH$_3$)$_2$ |
| 315 | 4-fluorophenyl | 2H-tertazol-5-yl | piperidin-4-yl | —CONHSO$_2$CH$_3$ |

TABLE V-continued

| No. | R | R² | W¹ | Q |
|---|---|---|---|---|
| 316 | 4-fluorophenyl | imdazol-1-yl | piperidin-4-yl | —CO₂H |
| 317 | 4-fluorophenyl | imdazol-1-yl | piperidin-4-yl | —CONH₂ |
| 318 | 4-fluorophenyl | imdazol-1-yl | piperidin-4-yl | —CONHCH₃ |
| 319 | 4-fluorophenyl | imdazol-1-yl | piperidin-4-yl | —CONH(CH₃)₂ |
| 320 | 4-fluorophenyl | imdazol-1-yl | piperidin-4-yl | —CONHSO₂CH₃ |

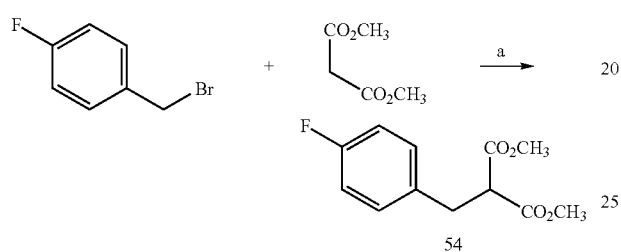

54

Reagents and conditions: (a) Na, MeO; reflux 2 hr.

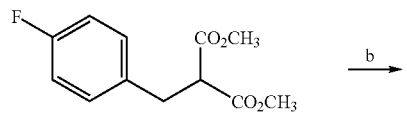

55

Reagents and conditions: (b) lypozyme, benzyl alcohol; 40° C. 18 hr.

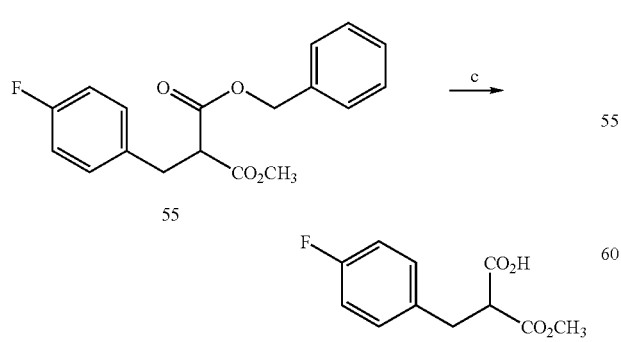

56

Reagents and conditions: (c) 5% Pd/C, hexane/toluene; rt.

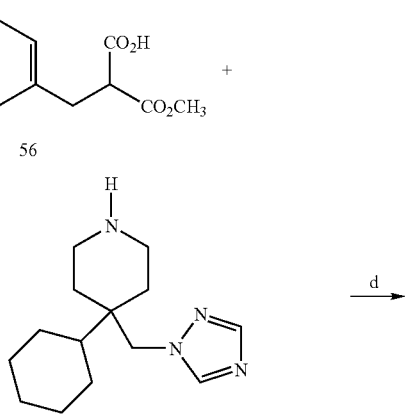

18

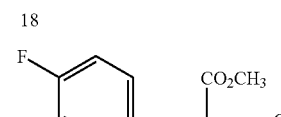

56

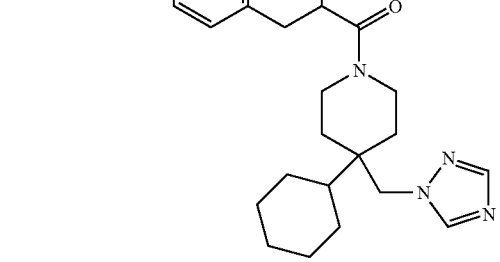

57

Reagents and conditions: (d) HOBt, NMM, EDCI; rt 18 hr.

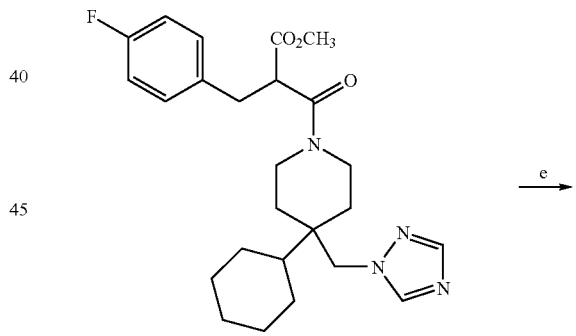

57

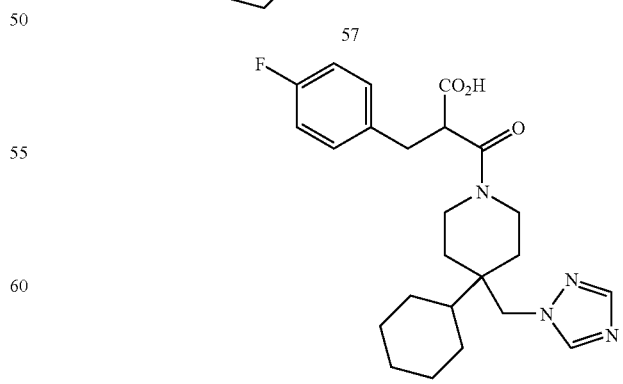

58

Reagents and conditions: (e) LiOH, THF/H₂O; rt 18 rt.

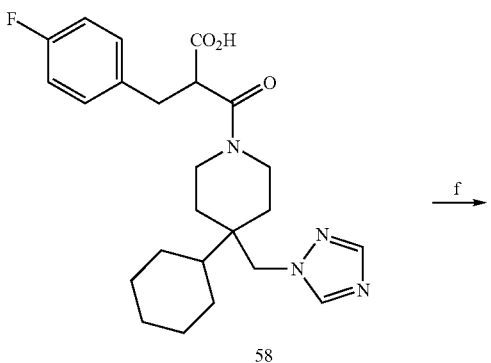

58

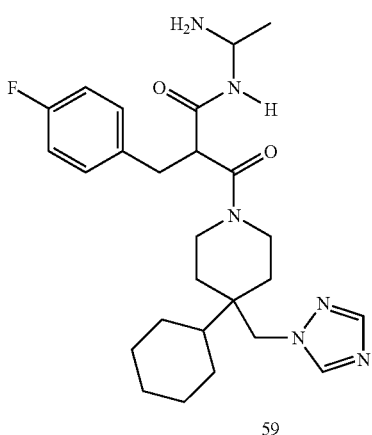

59

Reagents and conditions: (f) ethane, 1,1-diamine, EDCI, NMM, HOBt; rt 12 hr.

EXAMPLE 5

N-(1-Aminoethyl)-3-(4-cyclohexyl-4-[1,2,4]triazol-1-ylmethyl-piperidin-1-yl-2-(4-fluorobenzyl)-3-oxo-propionamide (59)

Preparation of 2-(4-fluorobenzyl)-malonic acid dimethyl ester (54): To a solution of anhydrous methanol (250 mL) is added sodium metal (2.875 g, 0.125 mol) piecewise until the evolution of gas has deceased. Dimethyl malonate (16.5 g, 0.125 mol) is added dropwise and the mixture is stirred for 30 minutes. 4-Fluoro benzyl bromide (23.8 g, 0.126 mol) is added dropwise, and the reaction is refluxed for 2 hour. The majority of the solvent is removed under vacuum, and aqueous HCl is added. The solution is extracted with $CHCl_3$, dried, and the solvent removed in vacuo. Distillation of the crude material under reduced pressure provides the desired compound which is used without further purification.

Preparation of 2-(4-fluorobenxyl)-malonic acid benzyl ester methyl ester (55): Lipozyme (4.0 g) is added to a solution of 2-(4-fluorobenzyl)-malonic acid dimethyl ester, 54, (1.0, 4.7 mmol) and benzyl alcohol (2.9 mL) in hexane (30 mL). The suspension is shaken at 40° C. and 200 rpm. After 18 hours the reaction is filtered, the solvent is removed in vacuo and the crude product purified over silica to afford the desired product which is used without further purification.

Preparation of 2-(4-fluorobenzyl)-malonic acid monomethyl ester (56): 5% Pd/C (64 mg) is added to a solution of 2-(4-fluorobenxyl)-malonic acid benzyl ester methyl ester, 55, (126 mg, 0.4 mmol) in 1:1 hexane/toluene (20 mL). Hydrogenation is carried out at RT until starting material is consumed. The catalyst is removed by filtration, and the solvent removed in vacuo to afford the desired product which is used without further purification.

Preparation of 3-(4-cylcohexyl-4-[1,2,4]triazol-1-ylmethyl-piperidin-1-yl)-2-(4-fluorobenzyl)-3-oxo-propionic acid methyl ester (57): To a solution of 2-(4-fluoro-benzyl)-malonic acid monomethyl ester, 56, (47.5 mg, 0.21 mmol), 4-cyclohexyl-4-[1,2,4]triazol-1-ylmethyl-piperidine, 18, (50 mg, 0.20 mmol), 1-hydroxybenzotriazole (54 mg, 0.40 mmol), 4-methylmorpholine (88 □l, 0.80 mmol) in N,N-dimethylformamide (7 mL) is added 1-(3-dimethylaminopropyl)-3-ethylcarbodiimide (50 mg, 0.26 mmol). The reaction mixture is stirred overnight and then aqueous ammonium chloride is added. The reaction is extracted with ethyl acetate, and the organics are separated dried over sodium sulfate, filtered and concentrated under reduced pressure. The crude product is purified by preparative HPLC to afford the desired compound.

Preparation of 3-(4-cylcohexyl-4-[1,2,4]triazol-1-ylmethyl-piperidin-1-yl)-2-(4-fluorobenzyl)-3-oxo-propionic acid (58): To a solution of 3-(4-cylcohexyl-4-[1,2,4]triazol-1-ylmethyl-piperidin-1-yl)-2-(4-fluorobenzyl)-3-oxo-propionic acid methyl ester, 57, (456 mg, 1 mmol) in THF/$H_2O$ (2:1) at RT is added LiOH (1.5 equiv.). The reaction is stirred at RT until the starting material is consumed. The solvent is removed in vacuo, and the residue is purified by reverse phase HPLC to provide the desired product.

Preparation of N-(1-Aminoethyl)-3-(4-cyclohexyl-4-[1,2,4]triazol-1-ylmethyl-piperidin-1-yl-2-(4-fluorobenzyl)-3-oxo-propionamide (59): To a mixture of 3-(4-cylcohexyl-4-[1,2,4]triazol-1-ylmethyl-piperidin-1-yl)-2-(4-fluorobenzyl)-3-oxo-propionic acid, 58, (442 mg, 1 mmol) and ethane 1,1-diamine (60 mg, 1 mmol) is added 1-hydroxy-benzotriazole (48.5 mg, 1.1 mmol), 4-methylmorpholine (176 □L, 1.6 mmol) in N,N-dimethylformamide (10 mL). 1-(3-Dimethylaminopropyl)-3-ethylcarbodiimide (200 mg, 1.04 mmol) is then added and the reaction is stirred at room temperature for 12 hours then poured into a mixture of water/$CH_2Cl_2$. The organic layer is separated, dried and concentrated to afford a crude product which is purified by reverse phase HPLC to provide the desired product.

For Category II compounds, other suitable $R^2$ units include —NHC(=NH)$NH_2$, —NHC(O)$NH_2$, —NHC(=NCH$_3$)$NH_2$, or —NHC(=NCN)NHNO$_2$. Other suitable Q units include quinolinyl, isoquinolinyl, indolyl, tetrahydroquinolinyl, tetrahydrodisoquinolinyl, imidazolyl, and triazolyl. For the first aspect of Category II the index j can be 0, 1, or 2.

FORMULATIONS

The present invention also relates to compositions or formulations which comprise the melanocortin receptor ligands according to the present invention. In general, the compositions of the present invention comprise:

a) an effective amount of one or more melanocortin receptor ligands according to the present invention; and b) one or more pharmaceutically acceptable excipients.

The compositions of this invention are typically provided in unit dosage form. For the purposes of the present invention the term "unit dosage form" is defined herein as comprising an effective amount of one or more melanocortin receptor ligands. The compositions of the present invention contain in one embodiment from about 1 mg to about 750 mg of one or more melanocortin receptor ligands, while in other embodiments the compositions comprise from about 3 mg to about 500 mg, or from about 5 mg to about 300 mg respectively.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of substances which can serve as pharmaceutically-acceptable excipients or components thereof are sugars, inter alia, lactose, glucose and sucrose, sorbitol, mannitol; starches, inter alia, corn starch and potato starch; cellulose and its derivatives, inter alia, sodium carboxymethyl cellulose, ethyl cellulose, and methyl cellulose; powdered tragacanth; malt; gelatin; talc; solid lubricants, such as stearic acid and magnesium stearate; vegetable oils, propylene glycol, glycerin, and polyethylene glycol; agar; alginic acid; wetting agents and lubricants, inter alia, sodium lauryl sulfate; coloring agents; flavoring agents; tableting agents, stabilizers; antioxidants; preservatives; pyrogen-free water; isotonic saline; and buffers.

Standard pharmaceutical formulation techniques are disclosed in *Remington's Pharmaceutical Sciences,* Mack Publishing Company, Easton, Pa., latest edition and *Peptide and Protein Drug Delivery,* Marcel Dekker, NY, 1991. Dosage forms useful for making the compositions of the present invention or which are compatible with the methods of use as described herein below are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor or "pro-drug" forms of the analogs of the present invention. It may be desirable to formulate the compounds of the present invention as a chemical species which itself is not a melanocortin receptor ligand as described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. Or alternatively, said "pro-drug" form may cross the blood/brain barrier before undergoing a change which releases the melanocortin receptor ligand in its active form. The term "pro-drug" relates to these species which are converted in vivo to the active pharmaceutical.

METHOD OF USE

The present invention also relates to a method for controlling one or more melanocortin receptor, MC-3 or MC-4, mediated or melanocortin receptor modulated mammalian diseases or conditions, said method comprising the step of administering to a human or higher mammal an effective amount of a composition comprising one or more of the melanocortin receptor ligands according to the present invention.

Because the melanocortin receptor ligands of the present invention can be delivered in a manner wherein more than one site of control can be achieved, more than one disease state can be modulated at the same time. Non-limiting examples of diseases which are affected by an antagonist or agonist which stimulates the MC-3 or MC-4 receptor, obesity and other body weight disorders, inter alia, anorexia and cachexia. Utilizing the melanocortin receptor ligands of the present invention will therefore affect a variety of diseases, disease states, conditions, or syndromes resulting from body weight disorders, inter alia, insulin resistance, glucose intolerance, Type-2 diabetes mellitus, coronary artery disease, elevated blood pressure, hypertension, dyslipidaemia, cancer (e.g., endometrial, cervical, ovarian, breast, prostate, gallbladder, colon), menstrual irregularities, hirsutism, infertility, gallbladder disease, restrictive lung disease, sleep apnea, gout, osteoarthritis, and thromboembolic disease.

MC-3 and MC-4 receptor ligands are also effective in treating disorders relating to behavior, memory (including learning), cardiovascular function, inflammation, sepsis, cardiogenic and hypovolemic shock, sexual dysfunction, penile erection, muscle atrophy, nerve growth and repair, intrauterine fetal growth, and the like.

Although the melanocortin receptor ligands of the present invention are discrete chemical entities, the method of delivery or the method of use may be coupled with other suitable drug delivery systems. For example, a drug delivery technique useful for the compounds of the present invention is the conjugation of the compound to an active molecule capable of being transported through a biological barrier (see e.g. Zlokovic, B. V., *Pharmaceutical Research,* Vol. 12, pp. 1395–1406 (1995)). A specific example constitutes the coupling of the compound of the invention to fragments of insulin to achieve transport across the blood brain barrier (Fukuta, M., et al. *Pharmaceutical Res.,* Vol. 11, pp. 1681–1688 (1994)). For general reviews of technologies for drug delivery suitable for the compounds of the invention see Zlokovic, B. V., *Pharmaceutical Res.,* Vol. 12, pp. 1395–1406 (1995) and Pardridge, W M, *Pharmacol. Toxicol.,* Vol. 71, pp. 3–10 (1992).

PROCEDURES

The compounds of the present invention can be evaluated for efficacy, for example, measurements or melanocortin receptor ligand constants, $K_i$, and $IC_{50}$ values can be obtained by any method chosen by the formulator.

Non-limiting examples of suitable assays include:
i) UV-visible substrate enzyme assay as described by L. Al Reiter, *Int. J. Peptide Protein Res.*, 43, 87–96 (1994).
ii) Fluorescent substrate enzyme assay as described by Thornberry et al., *Nature*, 356, 768–774 (1992).
iii) PBMC Cell assay as described in U.S. Pat. No. 6,204,261 B1 Batchelor et al., issued Mar. 20, 2001.
iv) accumulation of second messenger elements such as cAMP described by Chen et al., *Anal Biochem.* 226, 349–54, (1995).

Each of the above citations is included herein by reference.

Functional activity (in vitro pre-screening) can be evaluated using various methods known in the art. For example, measurement of the second messenger, cAMP, as described in citation (iv) above, evaluation by Cytosensor Microphysiometer techniques (Boyfield et al. 1996), or by using the compounds of the invention alone, or in combination with natural or synthetic MSH-peptides.

The compounds of the present invention will interact preferentially (i.e., selectively) to MC-4 and/or MC-3, relative to the other melanocortin receptors. Selectivity is particularly important when the compounds are administered to humans or other animals, to minimize the number of side effects associated with their administration. MC-3/MC-4 selectivity of a compound is defined herein as the ratio of the $EC_{50}$ of the compound for an MC-1 receptor ("$EC_{50}$–MC-1") over the $EC_{50}$ of the compound for the MC-3 ($EC_{50}$–MC-3)/MC-4 ($EC_{50}$–MC-4) receptor, the $EC_{50}$ values being measured as described above. The formulas are as follows:

MC-3 selectivity=[$EC_{50}$–MC-1]/[$EC_{50}$–MC-3]

MC-4 selectivity=[$EC_{50}$–MC-1]/[$EC_{50}$–MC-4]

For the purposes of the present invention a receptor ligand (analog) is defined herein as being "selective for the MC-3 receptor" when the above-mentioned ratio "MC-3-selectivity" is at least about 10. In other treatments, methods, or compositions this value is at least about 100, while for yet other embodiments of the present invention the selectivity is at least about 500.

A compound is defined herein as being "selective for the MC-4 receptor" when the above-mentioned ratio "MC-4-selectivity" is at least about 10. In other treatments methods, or compositions this value is at least about 100, while for yet other embodiments of the present invention the selectivity is at least about 500.

While particular aspects of the present invention and embodiments thereof have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A compound, including all enatiomeric and diasteriomeric forms and pharmaceutically acceptable salts thereof, said compound having the formula:

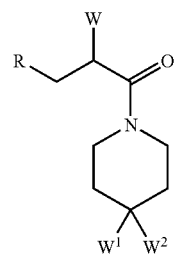

wherein R is a substituted or unsubstituted phenyl;
W is a pendant unit having the formula:

-L-Q wherein Q is substituted or unsubstituted unit selected from:
i) $C_1$–$C_{22}$ linear or branched alkyl;
ii) $C_2$–$C_{22}$ linear or branched alkenyl;
iii) $C_2$–$C_{22}$ linear or branched alkynyl;
iv) $C_3$–$C_8$ non-aromatic carbocyclic rings; and
v) $C_6$–$C_{14}$ aromatic carbocyclic rings;
L is a linking group having the formula:
i) —NHS(O)$_2$—; or
ii) —S(O)$_2$NH—;
$W^1$ is cyclohexyl; and
$W^2$ is 1,2,4-triazoylmethyl.

2. A compound according to claim 1 wherein R is selected from the group consisting of phenyl, 4-fluorophenyl, 4-chlorophenyl, 4-hydroxyphenyl, and 4-methylphenyl.

3. A compound according to claim 2 wherein R is 4-chlorophenyl.

4. A compound according to claim 1 wherein R is a substituted phenyl ring having as said substituent at least one $C_1$–$C_4$ linear, branched or cyclic alkyl unit.

5. A compound according to claim 1 wherein Q is selected from the group consisting of methyl, ethyl, propyl, iso-propyl, butyl, iso-butyl, tert-butyl, phenyl, and naphthalen-2-yl.

6. A compound including all enatiomeric and diasteriomeric forms and pharmaceutically acceptable salts thereof, having the formula:

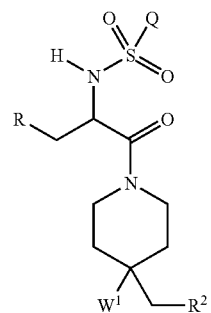

wherein R is 4-fluorophenyl or 4-chlorophenyl; $R^2$ is [1,2,4]triazol-1-yl: Q is methyl, trifluoromethyl, ethyl, propyl, iso-propyl, butyl, iso-butyl, tert-butyl, phenyl, or naphthalen-2-yl.

7. A compound and the salts thereof selected from the group consisting of

N-[1-(R)-(4-chlorobenzyl)-2-(4-cyclohexyl-4-[1,2,4]triazol-1-ylmethyl-piperidin-1-yl)-2-oxo-ethyl]-methanesulfonamide;
N-[1-(R)-(4-fluorobenzyl)-2-(4-cyclohexyl-4-[1,2,4]triazol-1-ylmethyl-piperidin-1-yl)-2-oxo-ethyl]-methanesulfonamide;
N-[1-(S)-(4-chlorobenzyl)-2-(4-cyclohexyl-4-[1,2,4]triazol-1-ylmethyl-piperidin-1-yl)-2-oxo-ethyl]-methanesulfonamide;
N-[1-(S)-(4-fluorobenzyl)-2-(4-cyclohexyl-4-[1,2,4]triazol-1-ylmethyl-piperidin-1-yl)-2-oxo-ethyl]-methanesulfonamide;
N-[1-(R)-(4-chlorobenzyl)-2-(4-cyclohexyl-4-[1,2,4]triazol-1-ylmethyl-piperidin-1-yl)-2-oxo-ethyl]-methanesulfonamide;
N-[1-(R)-(4-fluorobenzyl)-2-(4-cyclohexyl-4-[1,2,4]triazol-1-ylmethyl-piperidin-1-yl)-2-oxo-ethyl]-ethanesulfonamide;
N-[1-(S)-(4-chlorobenzyl)-2-(4-cyclohexyl-4-[1,2,4]triazol-1-ylmethyl-piperidin-1-yl)-2-oxo-ethyl]-ethanesulfonamide
N-[1-(S)-(4-fluorobenzyl)-2-(4-cyclohexyl-4-[1,2,4]triazol-1-ylmethyl-piperidin-1-yl)-2-oxo-ethyl]-ethanesulfonamide;
N-[1-(R)-(4-chlorobenzyl)-2-(4-cyclohexyl-4-[1,2,4]triazol-1-ylmethyl-piperidin-1-yl)-2-oxo-ethyl]-propanesulfonamide;
N-[1-(R)-(4-fluorobenzyl)-2-(4-cyclohexyl-4-[1,2,4]triazol-1-ylmethyl-piperidin-1-yl)-2-oxo-ethyl]-propanesulfonamide;
N-[1-(S)-(4-chlorobenzyl)-2-(4-cyclohexyl-4-[1,2,4]triazol-1-ylmethyl-piperidin-1-yl)-2-oxo-ethyl]-propanesulfonamide;
N-[1-(S)-(4-fluorobenzyl)-2-(4-cyclohexyl-4-[1,2,4]triazol-1-ylmethyl-piperidin-1-yl)-2-oxo-ethyl]-propanesulfonzmide;
N-[1-(R)-(4-chlorobenzyl)-2-(4-cyclohexyl-4-[1,2,4]triazol-1-ylmethyl-piperidin-1-yl)-2-oxo-ethyl]-isopropanesulfonamide;
N-[1-(R)-(4-fluorobenzyl)-2-(4-cyclohexyl-4-[1,2,4]triazol-1-ylmethyl-piperidin-1-yl)-2-oxo-ethyl]-isopropanesulfonamide;
N-[1-(S)-(4-chlorobenzyl)-2-(4-cyclohexyl-4-[1,2,4]triazol-1-ylmethyl-piperidin-1-yl)-2-oxo-ethyl]-isopropanesulfonamide;
N-[1-(S)-(4-fluorobenzyl)-2-(4-cyclohexyl-4-[1,2,4]triazol-1-ylmethyl-piperidin-1-yl)-2-oxo-ethyl]-isopropanesulfonamide;
N-[1-(R)-(4-chlorobenzyl)-2-(4-cyclohexyl-4-[1,2,4]triazol-1-ylmethyl-piperidin-1-yl)-2-oxo-ethyl]-trifluoromethanesulfonamide;
N-[1-(R)-(4-fluorobenzyl)-2-(4-cyclohexyl-4-[1,2,4]triazol-1-ylmethyl-piperidin-1-yl)-2-oxo-ethyl]-trifluoromethanesulfonamide;
N-[1-(S)-(4-chlorobenzyl)-2-(4-cyclohexyl-4-[1,2,4]triazol-1-ylmethyl-piperidin-1-yl)-2-oxo-ethyl]-trifluoromethansulfonamide; and
N-[1-(S)-(4-fluorobenzyl)-2-(4-cyclohexyl-4-[1,2,4]triazol-1-ylmethyl-piperidin-1-yl)-2-oxo-ethyl]-trifluoromethanesulfonamide.

8. A composition comprising:
A) an effective amount of one or more melanocortin receptor ligands, said ligands having all enatiomeric and diasteriomeric forms and their pharmaceutically acceptable salts, said ligands having the formula:

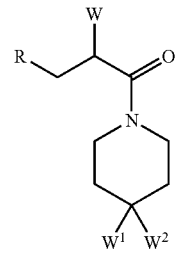

wherein R is a substituted or unsubstituted phenyl;
W is a pendant unit having the formula:

-L-Q wherein Q is a substituted or unsubstituted unit selected from:
i) $C_1$–$C_{22}$ linear or branched alkyl;
ii) $C_2$–$C_{22}$ linear or branched alkenyl;
iii) $C_2$–$C_{22}$ linear or branched alkynyl;
iv) $C_3$–$C_x$ non-aromatic carbocyclic rings; and
v) $C_6$–$C_{14}$ aromatic carbocyclic rings;
L is a linking group having the formula:
i) —NHS(O)$_2$—; or
ii) —S(O)$_2$NH—;
$W^1$ is cyclohexyl; and
$W^2$ is 1,2,4-triazoylmethyl; and
B) one or more pharmaceutically acceptable excipients.

9. A method for controlling weight gain in a human or higher mammal, said method comprising the step of administering to said human or higher mammal an effective amount of one or more melanocortin receptor ligands, said ligands having all enatiomeric and diasteriomeric forms and their pharmaceutically acceptable salts, said ligands having the formula:

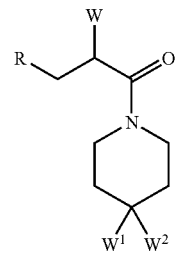

wherein R is a substituted or unsubstituted phenyl;
W is a pendant unit having the formula:

-L-Q wherein Q is substituted or unsubstituted unit selected from:
i) $C_1$–$C_{22}$ linear or branched alkyl;
ii) $C_2$–$C_{22}$ linear or branched alkenyl;
iii) $C_2$–$C_{22}$ linear or branched alkynyl;
iv) $C_3$–$C_8$ non-aromatic carbocyclic rings; and
v) $C_6$–$C_{14}$ aromatic carbocyclic rings;
L is a linking group having the formula:
i) —NHS(O)$_2$—; or
ii) —S(O)$_2$NH—;
$W^1$ is cyclohexyl; and
$W^2$ is 1,2,4-triazoylmethyl.

* * * * *